United States Patent
Bath et al.

(10) Patent No.: US 11,311,696 B2
(45) Date of Patent: Apr. 26, 2022

(54) HUMIDIFIER RESERVOIR

(71) Applicant: ResMed Pty Ltd, Bella Vista (AU)

(72) Inventors: Andrew Roderick Bath, Sydney (AU); Mark Bertinetti, Sydney (AU); Justin John Formica, Sydney (AU); Matthew Rolf Harrington, Gosford (AU); Saad Nasr, Sydney (AU); Joseph Samuel Ormrod, Sydney (AU); Jose Ignacio Romagnoli, Sydney (AU); Nathan John Row, Sydney (AU); Luke Andrew Stanislas, Sydney (AU); Hargopal Verma, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/481,860

(22) Filed: Sep. 22, 2021

(65) Prior Publication Data

US 2022/0008682 A1    Jan. 13, 2022

Related U.S. Application Data

(63) Continuation of application No. 16/432,120, filed on Jun. 5, 2019, which is a continuation of application
(Continued)

(30) Foreign Application Priority Data

| Mar. 15, 2013 | (AU) | ................................ 2013900901 |
| May 31, 2013 | (AU) | ................................ 2013901965 |

(Continued)

(51) Int. Cl.
*A61M 16/16*    (2006.01)
*A61M 16/00*    (2006.01)
(Continued)

(52) U.S. Cl.
CPC .......... *A61M 16/16* (2013.01); *A61M 16/024* (2017.08); *A61M 16/0066* (2013.01);
(Continued)

(58) Field of Classification Search
CPC ............ A61M 16/16–168; A61M 16/108–109
See application file for complete search history.

(56) References Cited

U.S. PATENT DOCUMENTS

| 141,175 A | 7/1873 | Shaw |
| 366,022 A | 7/1887 | Palmer |

(Continued)

FOREIGN PATENT DOCUMENTS

| AU | 2003265025 B2 | 4/2004 |
| CA | 2151992 | 6/1996 |

(Continued)

OTHER PUBLICATIONS

U.S. Appl. No. 17/471,856, filed Sep. 10, 2021, of Bath et al., entitled "Humidifier Reservoir,".
(Continued)

*Primary Examiner* — Michael J Tsai
(74) *Attorney, Agent, or Firm* — Nixon & Vanderhye P.C.

(57) ABSTRACT

A water reservoir for an apparatus for humidifying a flow of air for delivery to an entrance of the airways of a patient for respiratory therapy includes a reservoir base configured to hold a volume of water, a reservoir lid comprising an inlet and an outlet, a hinge joint to pivotally couple the reservoir lid to the reservoir base for pivotal movement between an open position and a closed position, wherein the reservoir lid and the reservoir base cooperate to form a sealed internal volume at the closed position, and a rotation stop, wherein the rotation stop is arranged between the reservoir lid and the reservoir base at the open position, and wherein the rotation stop is configured and arranged to disconnect the reservoir
(Continued)

lid from the reservoir base at the hinge joint when the reservoir lid is over-pivoted beyond the open position.

30 Claims, 55 Drawing Sheets

Related U.S. Application Data

No. 14/777,266, filed as application No. PCT/AU2014/000264 on Mar. 14, 2014, now Pat. No. 10,342,950.

(30) Foreign Application Priority Data

Jul. 15, 2013 (AU) ................................ 2013902601
Dec. 17, 2013 (AU) ................................ 2013904923

(51) Int. Cl.
   *A61M 16/10* (2006.01)
   *F24F 6/00* (2006.01)

(52) U.S. Cl.
   CPC ..... *A61M 16/0072* (2013.01); *A61M 16/0075* (2013.01); *A61M 16/1055* (2013.01); *A61M 16/1065* (2014.02); *A61M 16/161* (2014.02); *A61M 2016/0027* (2013.01); *A61M 2016/0033* (2013.01); *A61M 2205/21* (2013.01); *A61M 2205/3368* (2013.01); *A61M 2205/3382* (2013.01); *A61M 2205/3584* (2013.01); *A61M 2205/3653* (2013.01); *A61M 2205/505* (2013.01); *F24F 2006/008* (2013.01)

(56) References Cited

U.S. PATENT DOCUMENTS

| | | |
|---|---|---|
| 1,192,357 A | 7/1916 | Thatcher |
| 2,023,324 A | 12/1935 | Johnson |
| 2,139,429 A | 12/1938 | Wilson |
| 2,266,705 A | 12/1941 | Coghlan |
| 3,414,117 A | 12/1968 | Leeds |
| 3,479,801 A | 11/1969 | Shohachiro |
| 3,617,698 A | 11/1971 | Duncanson |
| 4,203,027 A | 5/1980 | O'Hare et al. |
| 4,782,831 A | 11/1988 | Trimble et al. |
| 4,836,401 A | 6/1989 | Ingemann |
| 4,921,642 A | 5/1990 | LaTorraca |
| 4,944,310 A | 7/1990 | Sullivan |
| 5,065,753 A | 11/1991 | Kalishman |
| 5,215,685 A | 6/1993 | Marino |
| 5,514,303 A | 5/1996 | Chiu |
| 5,529,060 A | 6/1996 | Salmon et al. |
| 5,564,415 A | 10/1996 | Dobson et al. |
| 5,701,950 A | 12/1997 | Imamura et al. |
| 5,704,345 A | 1/1998 | Berthon-Jones |
| 6,202,991 B1 | 3/2001 | Coniglio |
| 6,244,576 B1 | 6/2001 | Tsai |
| 6,256,454 B1 | 7/2001 | Dykes |
| 6,398,197 B1 | 6/2002 | Dickinson et al. |
| 6,532,959 B1 | 3/2003 | Berthon-Jones |
| 6,918,389 B2 | 7/2005 | Seakins et al. |
| 6,935,337 B2 | 8/2005 | Virr et al. |
| 7,111,624 B2 | 9/2006 | Thudor et al. |
| 7,413,173 B2 | 8/2008 | DiMatteo et al. |
| 7,677,246 B2 | 3/2010 | Kepler et al. |
| 7,849,852 B2 | 12/2010 | Bremner |
| 7,866,944 B2 | 1/2011 | Kenyon et al. |
| 8,006,691 B2 | 8/2011 | Kenyon et al. |
| 8,631,789 B2 | 1/2014 | Virr et al. |
| 8,636,479 B2 | 1/2014 | Kenyon et al. |
| 8,638,014 B2 | 1/2014 | Sears et al. |
| 8,677,993 B2 | 3/2014 | Cortez, Jr. |
| 8,739,780 B2 | 6/2014 | Tang et al. |
| 8,770,432 B2 | 7/2014 | Rueckheim |
| 9,227,035 B2 | 1/2016 | Crumblin et al. |
| 9,707,370 B2 | 7/2017 | Smith et al. |
| 10,342,950 B2 | 7/2019 | Bath et al. |
| 10,688,271 B2 | 6/2020 | Bath et al. |
| 2001/0017134 A1 | 8/2001 | Bahr |
| 2001/0050080 A1 | 12/2001 | Seakins et al. |
| 2005/0284475 A1 | 12/2005 | Loescher |
| 2007/0079826 A1 | 4/2007 | Kramer et al. |
| 2007/0132117 A1 | 6/2007 | Pujol |
| 2007/0169776 A1* | 7/2007 | Kepler et al. ...... A61M 16/0003 128/200.23 |
| 2007/0230927 A1 | 10/2007 | Kramer |
| 2008/0251071 A1 | 10/2008 | Armitstead et al. |
| 2008/0302361 A1 | 12/2008 | Snow et al. |
| 2009/0000620 A1 | 1/2009 | Virr |
| 2009/0044808 A1 | 2/2009 | Guney et al. |
| 2009/0050156 A1 | 2/2009 | Ng et al. |
| 2009/0194106 A1 | 8/2009 | Smith et al. |
| 2010/0000534 A1 | 1/2010 | Kooij et al. |
| 2010/0154796 A1 | 6/2010 | Smith et al. |
| 2011/0017212 A1 | 1/2011 | Kenyon |
| 2011/0023874 A1 | 2/2011 | Bath et al. |
| 2011/0155132 A1 | 6/2011 | Virr et al. |
| 2011/0162649 A1 | 7/2011 | Potharaju et al. |
| 2011/0180068 A1 | 7/2011 | Kenyon et al. |
| 2011/0248082 A1 | 10/2011 | Treacy |
| 2013/0008440 A1 | 1/2013 | Maurer et al. |
| 2014/0264975 A1 | 9/2014 | Bath et al. |
| 2015/0202402 A1* | 7/2015 | Kat ....................... A61M 16/16 128/203.27 |

FOREIGN PATENT DOCUMENTS

| | | |
|---|---|---|
| CN | 101537221 A | 9/2009 |
| CN | 101583395 A | 11/2009 |
| CN | 101678190 A | 3/2010 |
| CN | 101947343 A | 1/2011 |
| CN | 201768243 U | 3/2011 |
| CN | 102133447 A | 7/2011 |
| CN | 201954697 U | 8/2011 |
| CN | 202538099 U | 11/2012 |
| DE | 2431427 A1 | 1/1976 |
| EP | 2 540 335 A1 | 1/2013 |
| EP | 2 703 034 A2 | 3/2014 |
| GB | 1 401 399 | 7/1975 |
| GB | 1 450 097 | 9/1976 |
| GB | 2 010 097 A | 6/1979 |
| JP | 48-23271 U | 7/1973 |
| JP | 59-55316 U | 4/1984 |
| JP | 5-312363 A | 11/1993 |
| JP | 7-55210 A | 3/1995 |
| JP | 10-76008 A | 3/1998 |
| JP | 10-137339 A | 5/1998 |
| JP | 2000-337670 A | 12/2000 |
| JP | 2004-188121 | 7/2004 |
| JP | 2005-538802 A | 12/2005 |
| JP | 2009-504278 A | 2/2009 |
| JP | 2009-508647 A | 3/2009 |
| JP | 2010-203626 A | 9/2010 |
| JP | 2012-502698 A | 2/2012 |
| WO | WO 98/04310 | 2/1998 |
| WO | WO 98/04311 A1 | 2/1998 |
| WO | WO 98/34665 | 8/1998 |
| WO | WO 98/57691 A1 | 12/1998 |
| WO | WO 00/78381 | 12/2000 |
| WO | WO 01/10489 A2 | 2/2001 |
| WO | WO 02/066107 A1 | 8/2002 |
| WO | WO 2004/026382 A1 | 4/2004 |
| WO | WO 2004/073778 | 9/2004 |
| WO | WO 2004/112873 | 12/2004 |
| WO | WO 2005/063328 | 7/2005 |
| WO | WO 2006/074513 | 7/2006 |
| WO | WO 2006/130903 | 12/2006 |
| WO | WO 2007/019625 | 2/2007 |
| WO | WO 2007/019626 A1 | 2/2007 |
| WO | WO 2007/045017 A2 | 4/2007 |
| WO | WO 2008/056993 A2 | 5/2008 |
| WO | WO 2008/148146 A1 | 12/2008 |

(56) References Cited

FOREIGN PATENT DOCUMENTS

| WO | WO 2009/052560 | 4/2009 |
|----|----|----|
| WO | WO 2009/156921 | 12/2009 |
| WO | WO 2010/031126 | 3/2010 |
| WO | WO 2010/135785 | 12/2010 |
| WO | WO 2012/171072 | 12/2012 |
| WO | WO 2013/020167 | 2/2013 |
| WO | 2014/138804 | 9/2014 |

OTHER PUBLICATIONS

U.S. Appl. No. 17/509,380, filed Oct. 25, 2021, of Bath et al., entitled "Humidifier Reservoir,".
U.S. Appl. No. 17/509,151, filed Oct. 25, 2021, of Bath et al., entitled "Humidifier Reservoir,".
U.S. Appl. No. 17/480,286, filed Sep. 21, 2021, of Bath et al., entitled "Humidifier Reservoir,".
U.S. Appl. No. 17/481,466, filed Sep. 22, 2021, of Bath et al., entitled "Humidifier Reservoir,".
U.S. Appl. No. 17/482,838, filed Sep. 23, 2021, of Bath et al., entitled "Humidifier Reservoir,".
U.S. Appl. No. 17/485,625, filed Sep. 27, 2021, of Bath et al., entitled "Humidifier Reservoir,".
U.S. Appl. No. 17/505,761, filed Oct. 20, 2021, of Bath et al., entitled "Humidifier Reservoir,".
U.S. Appl. No. 17/488,849, filed Sep. 29, 2021, of Bath et al., entitled "Humidifier Reservoir,".
U.S. Appl. No. 17/489,000, filed Sep. 29, 2021, of Bath et al., entitled "Humidifier Reservoir,".
U.S. Appl. No. 17/508,018, filed Oct. 22, 2021, of Bath et al., entitled "Humidifier Reservoir,".
U.S. Appl. No. 17/509,546, filed Oct. 25, 2021, of Bath et al., entitled "Humidifier Reservoir,".
International Search Report issued in Application No. PCT/AU2014/000264, dated May 13, 2014, 8 pages.
Written Opinion of the International Searching Authority issued in Application No. PCT/AU2014/000264, dated May 13, 2014, 4 pages.
"Respiratory Physiology", by John B, West, Lippincott Williams & Wilkins, 9th edition published 2011, 8 pages.
"CPAP System XT Series", Apex Medical Corp., published Aug. 2007, 4 pages.
International Preliminary Report on Patentability issued in PCT Application No. PCT/AU2014/000264 dated Sep. 15, 2015.
First Examination Report issued in corresponding New Zealand Application No. 631374 dated Oct. 29, 2015.
Patent Examination Report No. 1 issued in corresponding Australian Appln. No. 2014231714 dated Mar. 23, 2016.
Non-Final Office Action issued in related U.S. Appl. No. 14/211,346 dated Aug. 31, 2015.
First Office Action issued in corresponding Chinese Patent Application No. 201480028533.9 dated Jun. 30, 2016 with English language translation thereof.
APEX XT-Auto Instruction Manual, USPTO to assume before Applicant's filing date.
APEX "Introducing a new member of our CPAP family" APEX XT-Auto, USPTO to assume before Applicant's filing date.
Final Office Action issued in related U.S. Appl. No. 14/211,346 dated May 26, 2016.
Extended European Search Report issued in a corresponding European Application No. 14763136.0 dated Sep. 7, 2016.
Patent Examination Report No. 2 dated Oct. 19, 2016 issued in Australian Application No. 2014231714 (4 pages).
Office Action dated Mar. 1, 2017 issued in related U.S. Appl. No. 14/211,346 (27 pages).
First Examination Report dated Apr. 4, 2017 issued in New Zealand Application No. 730481 (2 pages).
Communication dated May 30, 2017 issued in European Application No. 14 763 136.0 (7 pages).
Office Action dated Oct. 2, 2017 issued in Taiwanese Application No. 103109227 with English translation (11 pages).
Notice of Reasons for Rejection dated Jan. 5, 2018 issued in Japanese Application No. 2015-561828 with English translation (11 pages).
Communication dated Jul. 16, 2018 issued in European Application No. 14763136.0 (8 pages).
Notice of Reasons for Rejection dated Mar. 18, 2019 in Japanese Application No. 2018-111737, with English translation, 22 pages.
Bath et al., Parent U.S. Appl. No. 16/432,120, filed Jun. 5, 2019, for a "Humidifier Reservoir," .
Communication Pursuant to Article 94(3) EPC dated May 30, 2017 in European Application No. 14 763 136.0, 7 pages.
First Office Action dated Dec. 16, 2021 in Chinese Application No. 201911174296.8, with English translation, 17 pages.

* cited by examiner

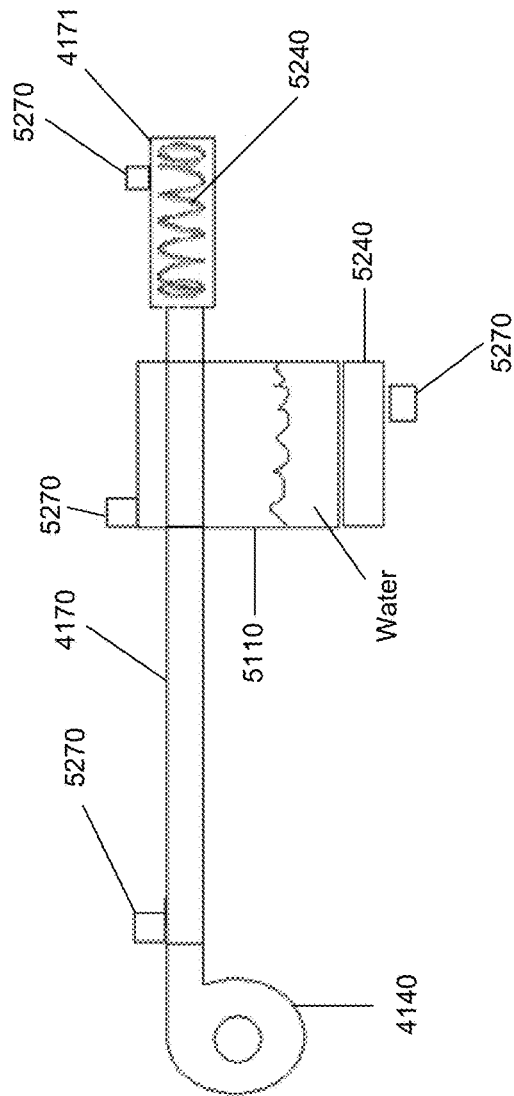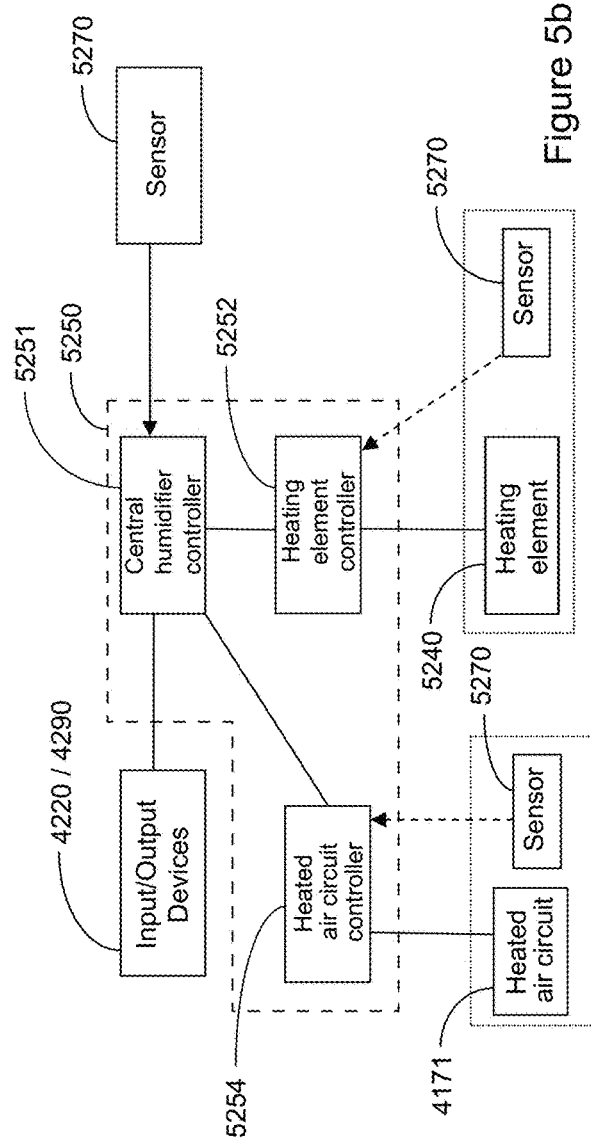
Figure 5a
Figure 5b

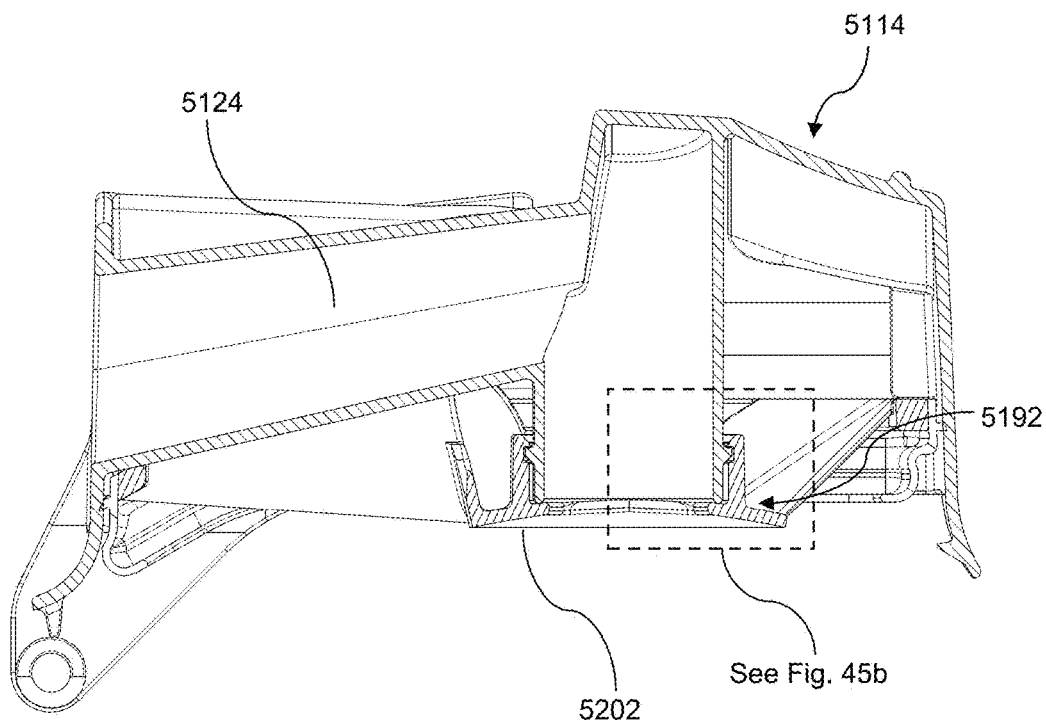
Figure 45a
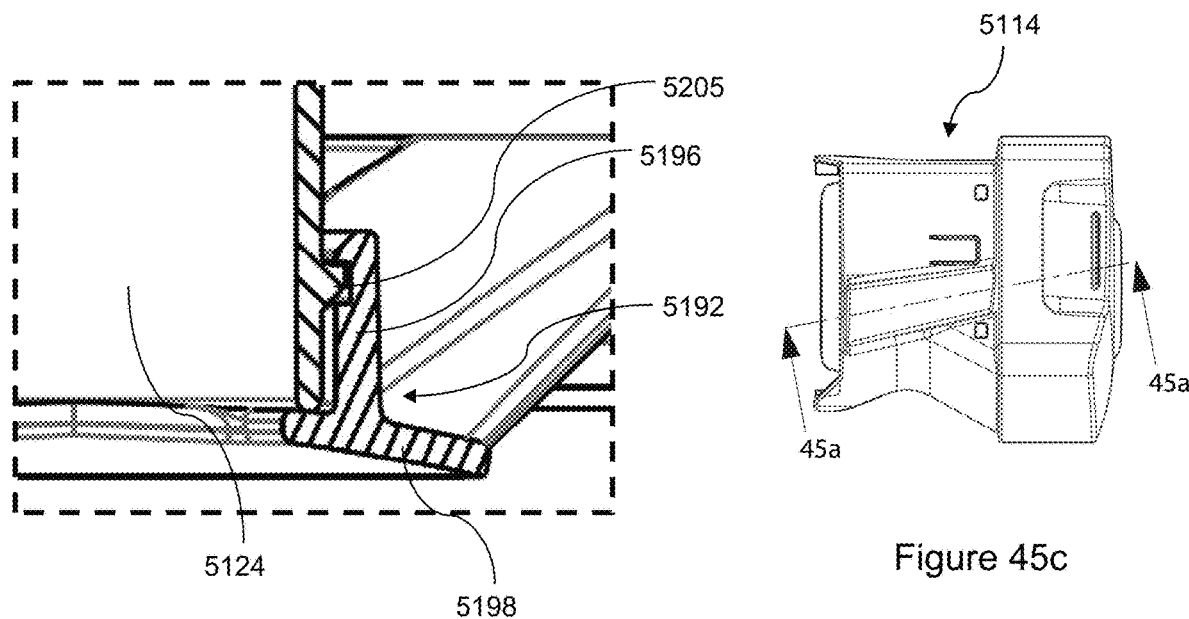
Figure 45b
Figure 45c

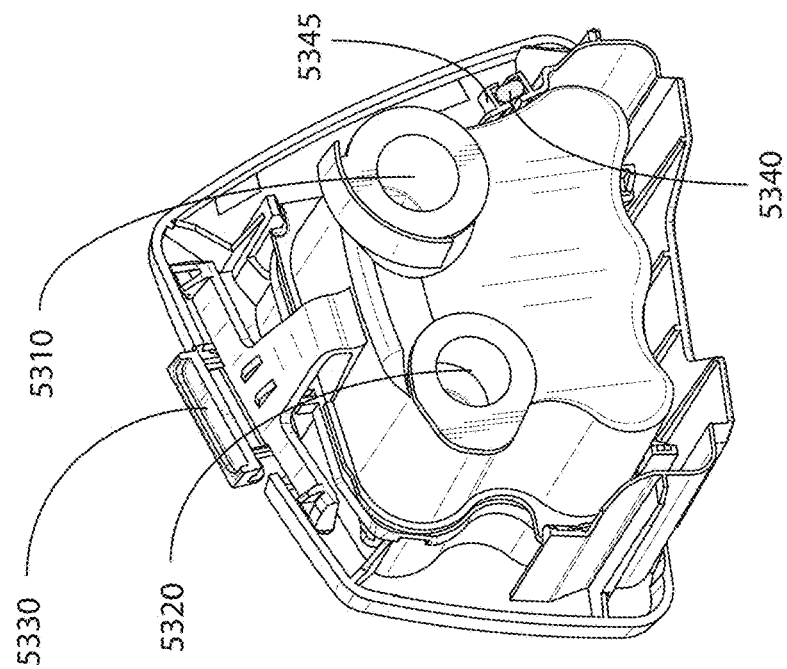
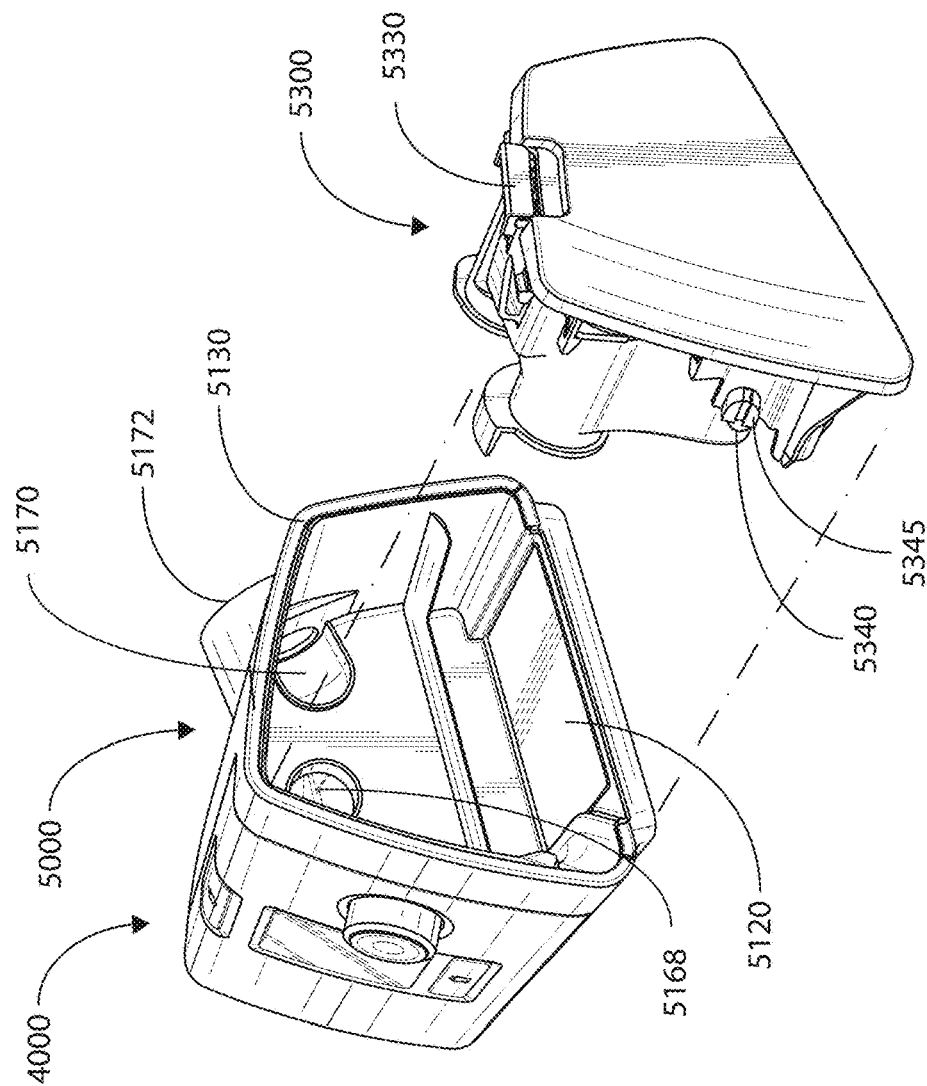
Figure 60
Figure 59

HUMIDIFIER RESERVOIR

1 CROSS-REFERENCE TO RELATED APPLICATIONS

This application is a continuation of U.S. application Ser. No. 16/432,120, filed Jun. 5, 2019, which is a continuation of U.S. application Ser. No. 14/777,266, filed Sep. 15, 2015, now U.S. Pat. No. 10,342,950, which is the U.S. national phase of International Application No. PCT/AU2014/000264 filed 14 Mar. 2014, which designated the U.S. and claims priority from Australian Provisional Patent Application 2013900901, filed 15 Mar. 2013, Australian Provisional Patent Application 2013901965, filed 31 May 2013, Australian Provisional Patent Application 2013902601, filed 15 Jul. 2013, and Australian Provisional Patent Application 2013904923, filed 17 Dec. 2013, the entire contents of each of these applications being incorporated herein by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use.

2.2 Description of the Related Art

Human Respiratory System

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.1 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient, and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.2 Systems

A treatment system may comprise a Respiratory Pressure Therapy Device (RPT device), an air circuit, a humidifier, a patient interface, and data management.

2.2.3 Patient Interface

A patient interface may be used to interface respiratory equipment to its user, for example by providing a flow of air. The flow of air may be provided via a mask to the nose and/or mouth, or via a tracheostomy tube to the trachea of the user. Depending upon the therapy to be applied, the patient interface may form a seal, e.g. with a face region of the patient, to facilitate the delivery of air at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of air at a positive pressure of about 10 cmH2O. Some masks suffer from being one or more of obtrusive, aesthetically undesirable, costly, poorly fitting, difficult to use, and uncomfortable especially when worn for long periods of time or when a patient is unfamiliar with a system. Masks designed solely for aviators as part of personal protection equipment or for the administration of anaesthetics may be tolerable for their original application, but nevertheless be undesirably uncomfortable to be worn for extended periods, for example, while sleeping or throughout the day.

2.2.4 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors and a microprocessor-based controller. A blower may include a servo-controlled motor, a volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

Table of noise output levels of prior RPT devices (one specimen only, measured using test method specified in ISO3744 in CPAP mode at 10cmH$_2$O).

| RPT Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

2.2.5 Humidifier

Delivery of a flow of air to a patient's airways without humidification may cause drying of the airways. Medical humidifiers are used to increase humidity and/or temperature of the flow of air in relation to ambient air when required, typically where the patient may be asleep or resting (e.g. at a hospital). As a result, a medical humidifier may be small for bedside placement, and may be configured to humidify and/or heat the flow of air delivered to the patient without humidifying and/or heating the patient's surroundings. Room-based systems (e.g. a sauna, an air conditioner, an evaporative cooler), for example, may also humidify and/or heat air that is breathed in by the patient, however they would do so by humidifying and/or heating the entire room, which may cause discomfort to the occupants.

The use of a humidifier with a RPT device and the patient interface produces humidified air that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to a RPT device via an air conduit, is integrated with the RPT device or configured to be directly coupled to the relevant RPT device. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, an air inlet to receive air from the RPT device, and an air outlet adapted to be connected to an air circuit that delivers the humidified air to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

Typically, the heating element is incorporated in a heater plate which sits under, and is in thermal contact with, the water tub. Thus, heat is transferred from the heater plate to the water reservoir primarily by conduction.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to apparatus for treating a respiratory disorder including a patient interface, an air circuit, and a source of air at positive pressure.

Another aspect of the present technology relates to methods used in the diagnosis, amelioration, treatment or prevention of a respiratory disorder.

One aspect of the present technology relates to an apparatus for humidifying a flow of air, comprising a heater plate, a chamber in fluid communication with the flow of air and a reservoir comprising a conductive portion in thermal engagement with the heater plate, the apparatus configured so that varying a first pressure of the flow of air in the chamber varies a level of thermal engagement between the conductive portion and the heater plate.

In one form, the reservoir further comprises an inlet and an outlet.

In one form, the thermal engagement is in a first direction that is substantially normal to a surface of the conductive portion.

In one form, the apparatus is further configured to vary a magnitude of a force between the conductive portion and the heater plate in the first direction as the first pressure is varied.

In one form, the chamber is part of the reservoir.

In one form, the chamber further comprises a compliant portion.

In one form, the apparatus further comprises a dock configured to receive the reservoir, and the dock comprises the heater plate.

In one form, the dock further comprises a cavity having a top portion and a bottom portion, the bottom portion having the heater plate located thereon, the cavity configured to retain at least a portion of the reservoir therein.

In one form, the compliant portion is compressed to enable insertion of the reservoir into the cavity of the dock.

In one form, the top portion of the cavity is moveable between an open and closed configuration to facilitate insertion of the reservoir into the cavity.

In one form, the compliant portion is configured to adjust in size as the first pressure is varied to vary the level of thermal engagement between the heater plate and the conductive portion.

In one form, the reservoir further includes a base and a lid, the base structured to hold a volume of liquid and including the conductive portion.

In one form, the base and lid are pivotably coupled together.

In one form, the compliant portion forms a seal between the base and lid.

In one form, the reservoir further includes a latch to secure the base and lid together.

In one form, the reservoir further comprises at least one handle to facilitate coupling of the reservoir to the dock.

In one form, the reservoir further includes a retaining clip adapted to engage with a recess on the dock to retain the reservoir in the cavity of the dock.

In one form, the reservoir is structured to prevent refilling of the reservoir when the reservoir is coupled to the dock.

In one form, at least a portion of the reservoir is prevented from being opened when the reservoir is coupled to the dock.

In one form, the reservoir includes a re-filling cap.

In one form, the apparatus further comprises an overfill protection element configured to prevent filling the reservoir above a predetermined maximum volume of water.

In one form, the overfill protection element comprises at least one orifice formed in a wall of the reservoir, the at least one orifice defines an egress path of water when the predetermined maximum volume of water is exceeded.

In one form, the overfill protection element comprises a sloped profile in the side profile of a wall of the reservoir, the sloped profile defines an egress path of water when the predetermined maximum volume of water is exceeded.

One aspect of the present technology relates to a method for varying thermal contact between a heater plate and a reservoir in a humidification system for humidifying a flow of air, the method comprising varying a pressure of the flow of air in the reservoir that is in fluid communication with the flow of air to vary a force between the heater plate and the reservoir.

Another aspect of the present technology relates to an apparatus for humidifying a flow of air, comprising a heater plate and a reservoir comprising an inlet to receive the flow of air, an outlet and a conductive portion in thermal contact with the heater plate, and wherein the apparatus is configured so that varying a pressure of the flow of air in the reservoir varies a force between the heater plate and the conductive portion in a direction of thermal contact.

In one form, the apparatus further comprises a dock connectable with the reservoir.

In one form, the dock is configured to constrain the reservoir from opening in the direction of thermal contact.

Another aspect of the present technology relates to a reservoir configured to contain a volume of liquid for humidifying a pressurised flow of air, comprising a base portion comprising a conductive portion, a lid portion comprising an inlet and an outlet and a compliant portion wherein the base portion and the lid portion are pivotably engaged and configurable in an open configuration and a closed configuration while pivotably engaged, and the seal sealingly engages the base portion and the lid portion when the reservoir is in the closed configuration.

In one form, the compliant portion comprises an outlet tube, and a baffle, the baffle being configured to connect to the inlet tube.

Another aspect of the present technology relates to an apparatus for humidifying a flow of air, comprising a heater plate and a reservoir comprising an inlet, an outlet, a compliant portion and a conductive portion in thermal contact with the heater plate, wherein the apparatus is configured so that varying a height of the compliant portion varies a level of thermal engagement between the conductive portion and the heater plate.

In one form, the apparatus is configured so that the thermal engagement is in a first direction that is substantially normal to a surface of the conductive portion.

Another aspect of the present technology relates to a method of varying a level of thermal engagement in a humidifier apparatus, the method comprising (i) thermally engaging a heater plate with a conductive portion of a reservoir and (ii) varying a height of a compliant portion of the reservoir to vary a level of thermal engagement between the conductive portion and the heater plate.

Another aspect of the present technology relates to a water reservoir for an apparatus for humidifying a flow of air, including a base portion configured to hold a predetermined maximum volume of water, the base portion including an overfill protection element configured and arranged to prevent filling the base portion above the maximum volume of water.

In one form, the water reservoir further comprises a lid portion movably connected to the base portion to allow the water reservoir to be convertible between an open configuration and a closed configuration.

In one form, the overfill protection element is configured and arranged to prevent filling the base portion above the maximum volume of water when the water reservoir is in the open configuration and/or the closed configuration.

In one form, the water reservoir further comprises a compliant portion configured to sealingly engage the lid portion and the base portion when the reservoir is in the closed configuration.

In one form, the compliant portion is configured to block or seal the overfill protection element to prevent fluid communication into and out of the reservoir.

In one form, the overfill protection element is configured so that excess water above the maximum volume of water will spill out via the overfill protection element when the maximum volume of water is exceeded and the base portion is in its normal, working orientation.

In one form, the overfill protection element comprises at least one orifice that defines an egress path of water when the maximum volume of water is exceeded.

In one form, the overfill protection element is configured such that water only spills out through the at least one orifice when the maximum volume of water is exceeded.

In one form, the at least one orifice is provided in one or more positions along a perimeter of the base portion.

In one form, the at least one orifice is provided through an upper lip or flange provided along a perimeter of the base portion.

In one form, the at least one orifice includes one or more apertures, holes, slits, or slots that allows fluid communication into and out of the reservoir.

In one form, the water reservoir further comprises a compliant portion configured to sealingly engage the base portion when the reservoir is in a closed configuration, wherein the compliant portion is configured to block or seal the at least one orifice to prevent fluid communication into and out of the reservoir.

In one form, the compliant portion sealing engages the base on an outside of the at least one orifice.

In one form, the overfill protection element comprises a sloped profile in a side profile of the base portion that defines an egress path of water when the maximum volume of water is exceeded.

In one form, the sloped profile extends in one or more directions.

In one form, the overfill protection element is configured such that water only spills out through the sloped profile when the maximum volume of water is exceeded.

In one form, the water reservoir further comprises a compliant portion configured to sealingly engage the base portion when the reservoir is in a closed configuration, wherein the compliant portion is configured to block or seal the sloped profile to prevent fluid communication into and out of the reservoir.

In one form, the compliant portion sealing engages the base on an outer edge of the sloped profile.

In one form, the overfill protection element is configured and arranged to prevent filling the base portion above the maximum volume of water when the water reservoir is in the open configuration.

In one form, the overfill protection element is configured and arranged to prevent filling the base portion above the maximum volume of water when the water reservoir is in the closed configuration.

In one form, the overfill protection element forms one or more air locks to prevent further ingress of water into the base portion when the maximum volume of water is reached.

In one form, the water reservoir further comprises a lid portion movably connected to the base portion to allow the water reservoir to be convertible between an open configuration and a closed configuration.

In one form, the overfill protection element is configured and arranged to form the one or more air locks when the water reservoir is in the closed configuration.

In one form, the water reservoir further comprises an inlet tube and an outlet tube in communication with the base portion, the inlet tube and the outlet tube being arranged such that, when the maximum volume of water is reached, air in the reservoir is prevented from escaping through the inlet tube and the outlet tube thereby preventing further ingress of water into the base portion.

Another aspect of the present technology relates to an apparatus for humidifying a flow of air, comprising a water reservoir dock and the water reservoir substantially described as above provided to the water reservoir dock.

In one form, the water reservoir dock forms a cavity to receive the water reservoir.

In one form, the water reservoir dock includes a heater plate adapted to thermally engage a conductive portion provided to the water reservoir.

Another aspect of the present technology relates to a method of preventing overfilling in a humidifier reservoir, the method comprising (i) incorporating an overfill protection element in a base portion of the humidifier reservoir and (ii) configuring the overfill protection element so that excess water above a predetermined maximum volume of water will spill out via the overfill protection element when the maximum volume of water is exceeded and the base portion is in its normal, working orientation.

In one form, the overfill protection element includes at least one orifice.

In one form, the overfill protection element includes a sloped profile.

In one form, the method of preventing overfilling in a humidifier reservoir further comprises configuring the overfill protection element such that water only spills via the overfill protection element when the maximum volume of water is exceeded.

Another aspect of the present technology relates to a reservoir configured to hold a predetermined maximum volume of water, comprising a plurality of walls forming a cavity structured to hold the predetermined maximum volume of water, an inlet tube configured to deliver a supply of air into the cavity, the inlet tube having an inlet interior end and an inlet exterior end and an outlet tube configured to deliver a humidified supply of air from the cavity, the outlet tube having an outlet interior end and an outlet exterior end, wherein the inlet interior end and the outlet interior end are located within the cavity and the inlet exterior end and the outlet exterior end are located in one of the plurality of walls of the cavity, a first axis defined by the inlet interior end and the inlet exterior end and a second axis defined by the outlet interior end and the outlet exterior end, wherein when the reservoir is tilted approximately 90° to normal working orientation the first axis is on a first angle such that the inlet interior end and the inlet exterior end are positioned at different heights, such that the predetermined maximum volume of water is below at least one of the inlet interior end or the inlet exterior end to prevent spillback of water through the inlet tube.

In one form, the reservoir is further configured so that when the reservoir is tilted approximately 90° to normal working orientation the second axis is on a second angle such that the outlet interior end and the outlet exterior end are positioned at different heights, such that the predetermined maximum volume of water is below at least one of the outlet interior end or the outlet exterior end to prevent spillback of water through the outlet tube.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

4.2 Therapy 4.2.1 Respiratory System

Figure 1A:
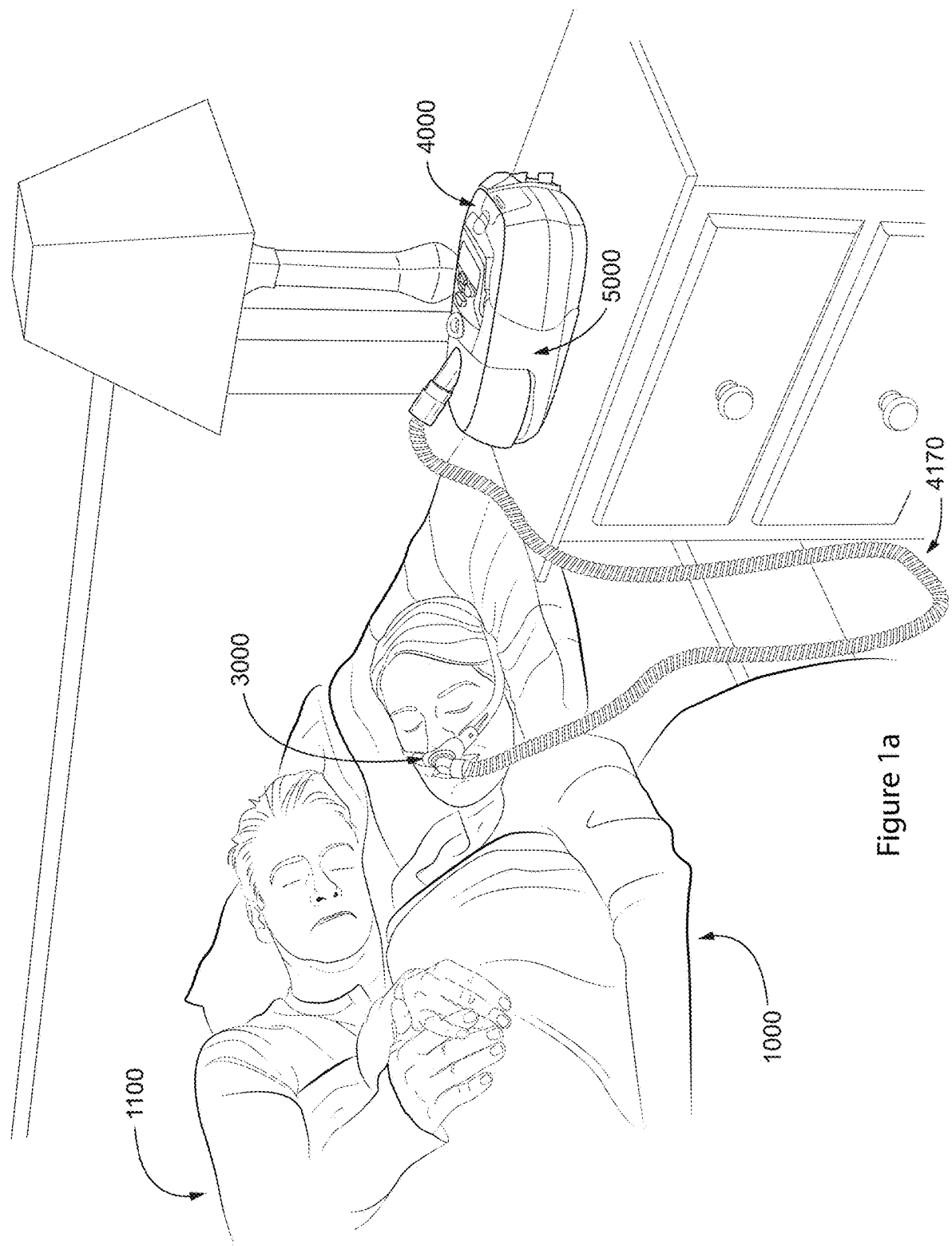
FIG. 1a shows a system including a patient 1000 wearing a patient interface 3000, in the form of nasal pillows, receives a supply of air at positive pressure from a RPT device 4000. Air from the RPT device is humidified in a humidifier 5000, and passes along an air circuit 4170 to the patient 1000.
Figure 1B:
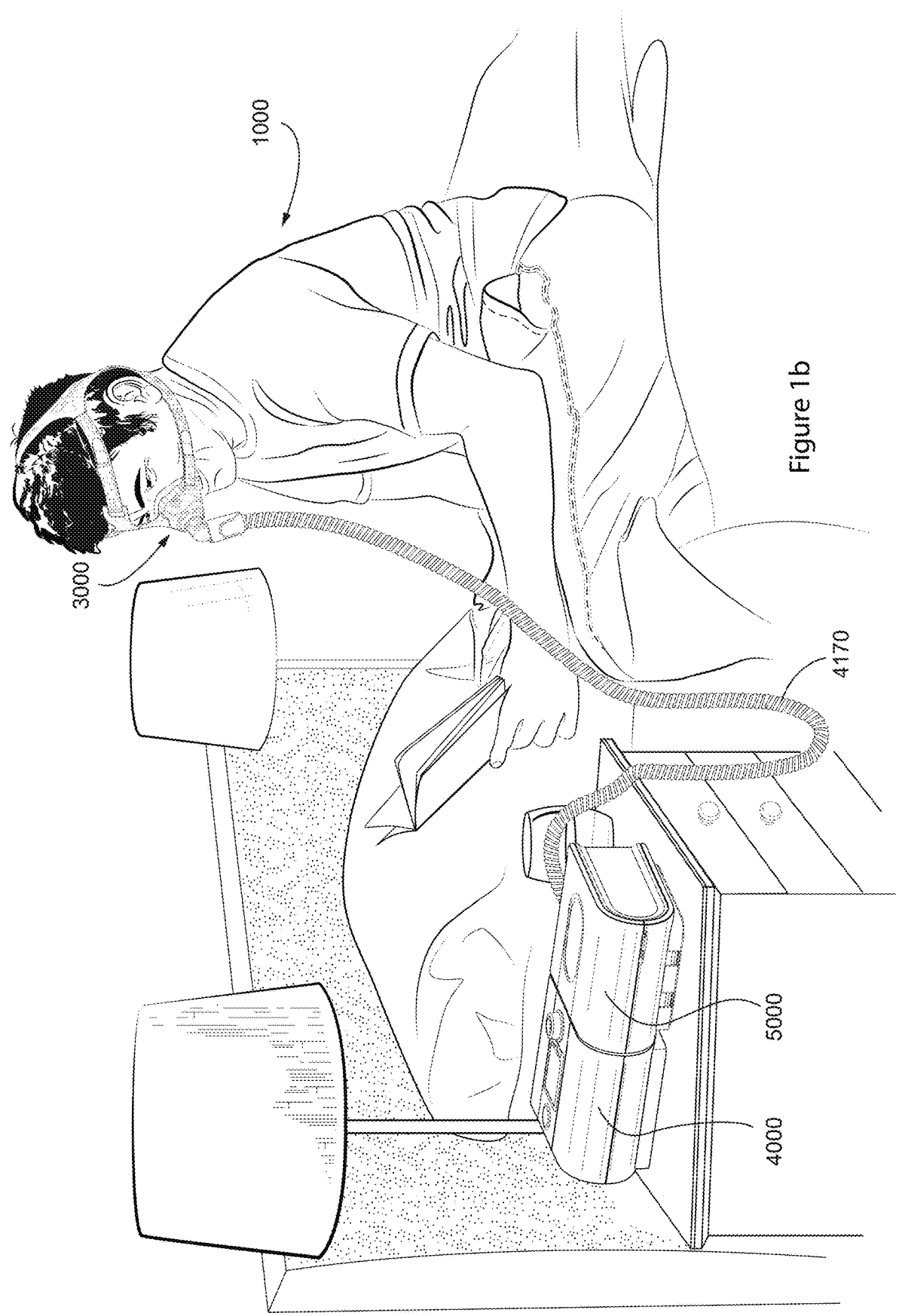
FIG. 1b shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
Figure 1C:
FIG. 1c shows a system including a patient 1000 wearing a patient interface 3000, in the form of a full-face mask, receives a supply of air at positive pressure from a RPT device. Air from the RPT device is humidified in a humidifier 5000, and passes along an air circuit 4170 to the patient 1000.
Figure 2A:
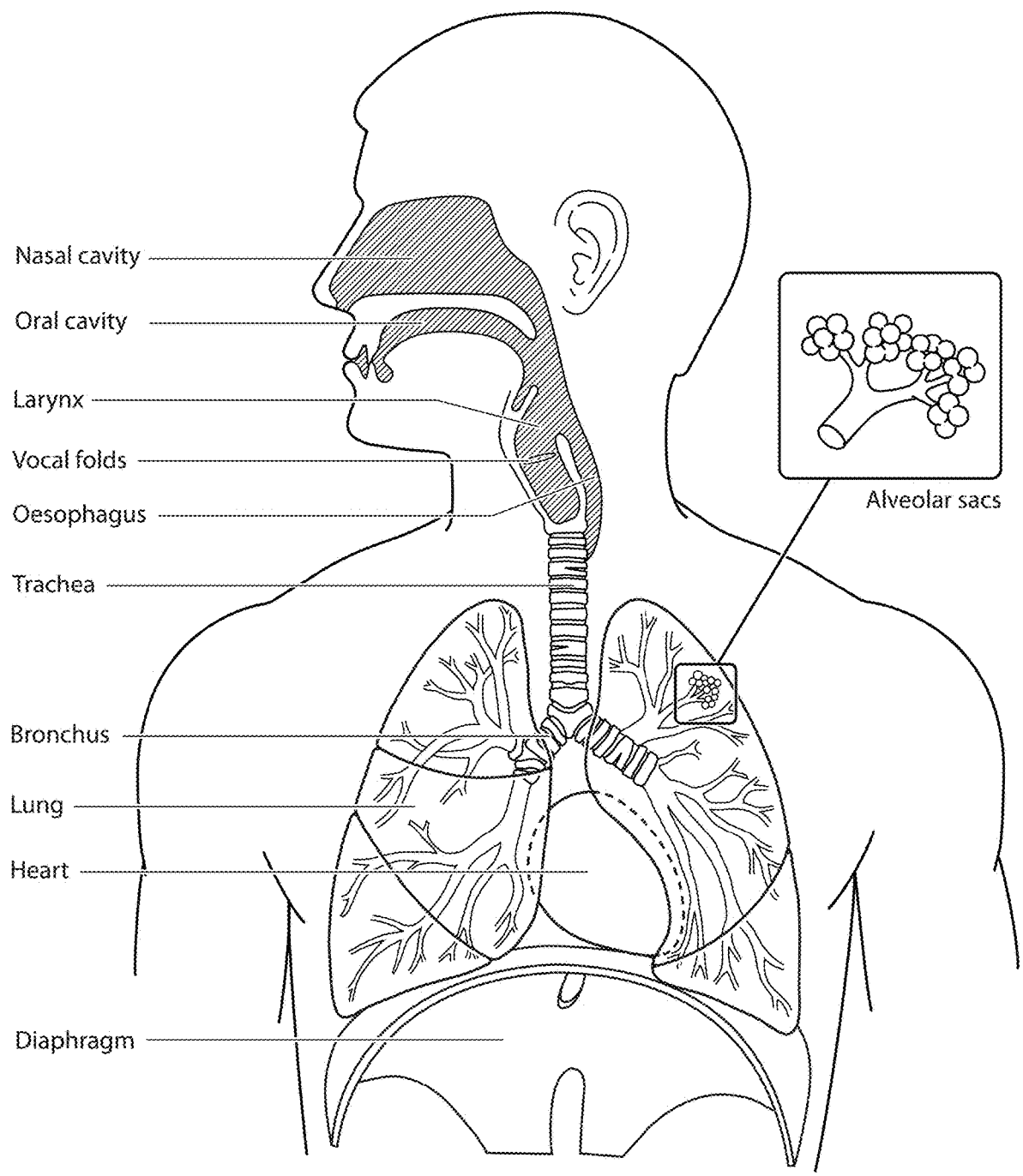

FIG. 2a shows an overview of a human respiratory system including the nasal and oral cavities, the larynx, vocal folds, oesophagus, trachea, bronchus, lung, alveolar sacs, heart and diaphragm.

Figure 2B:
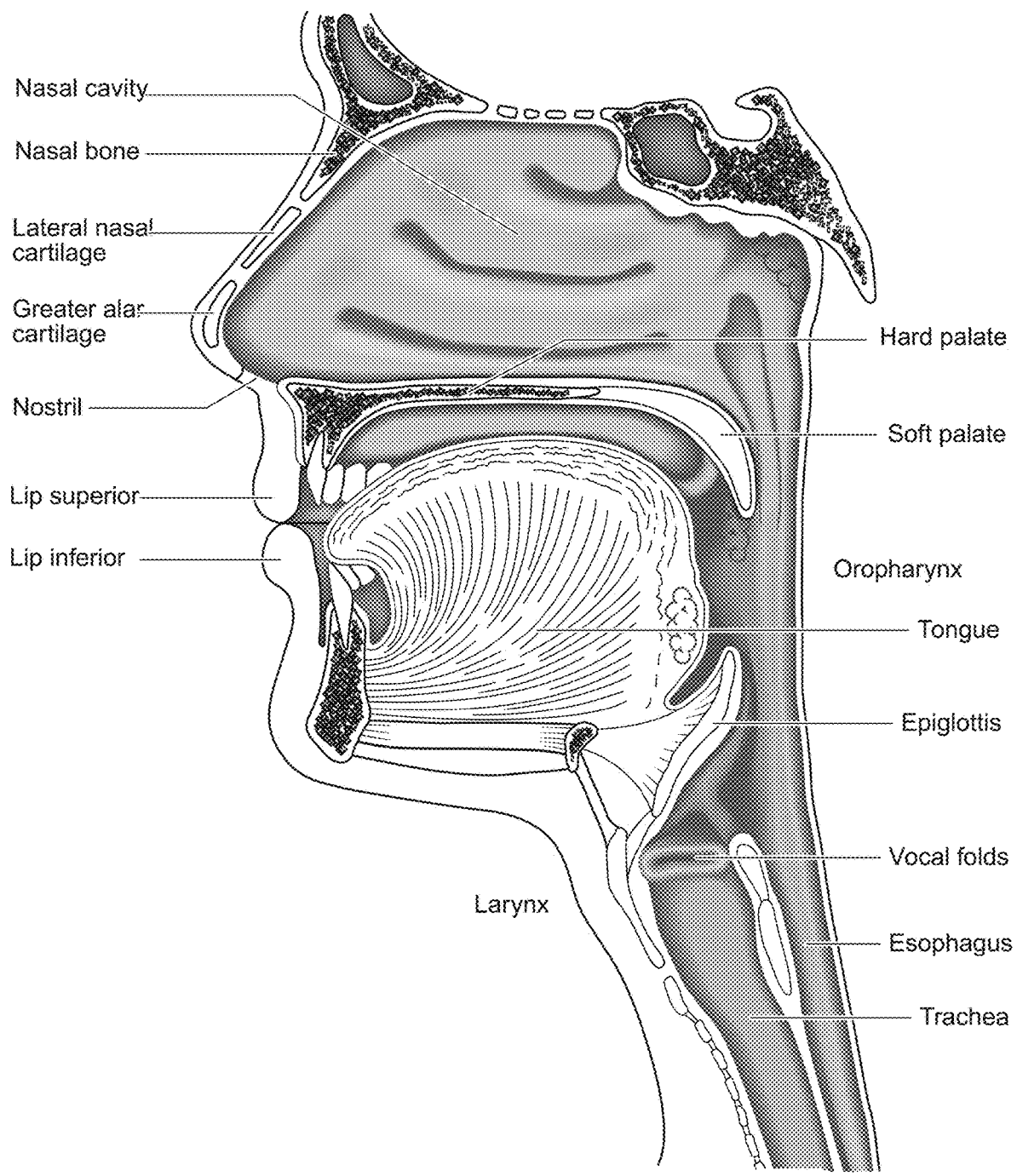

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3A:
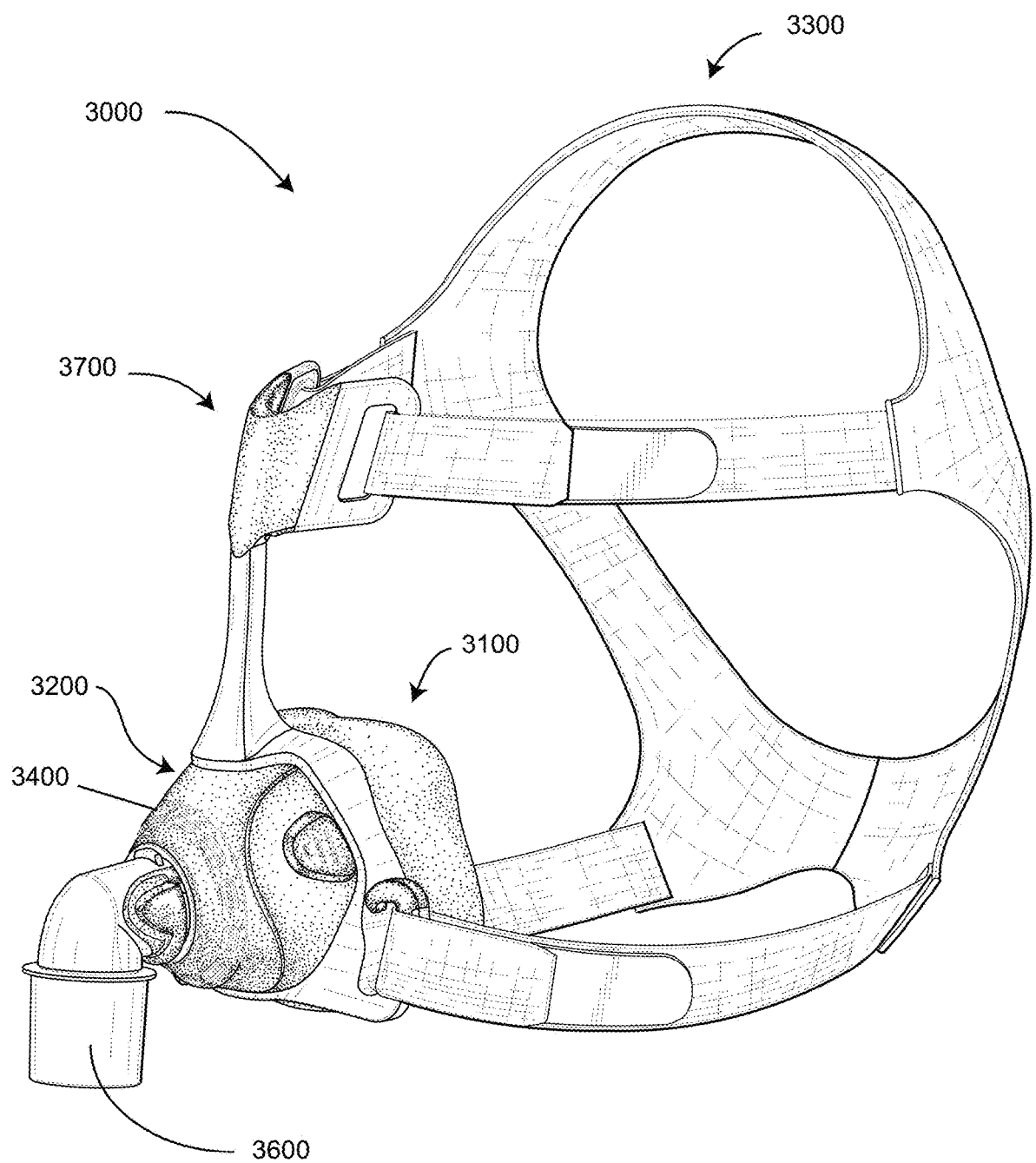

FIG. 3a shows a patient interface in accordance with one form of the present technology.

4.4 Respiratory Apparatus

Figure 4A:
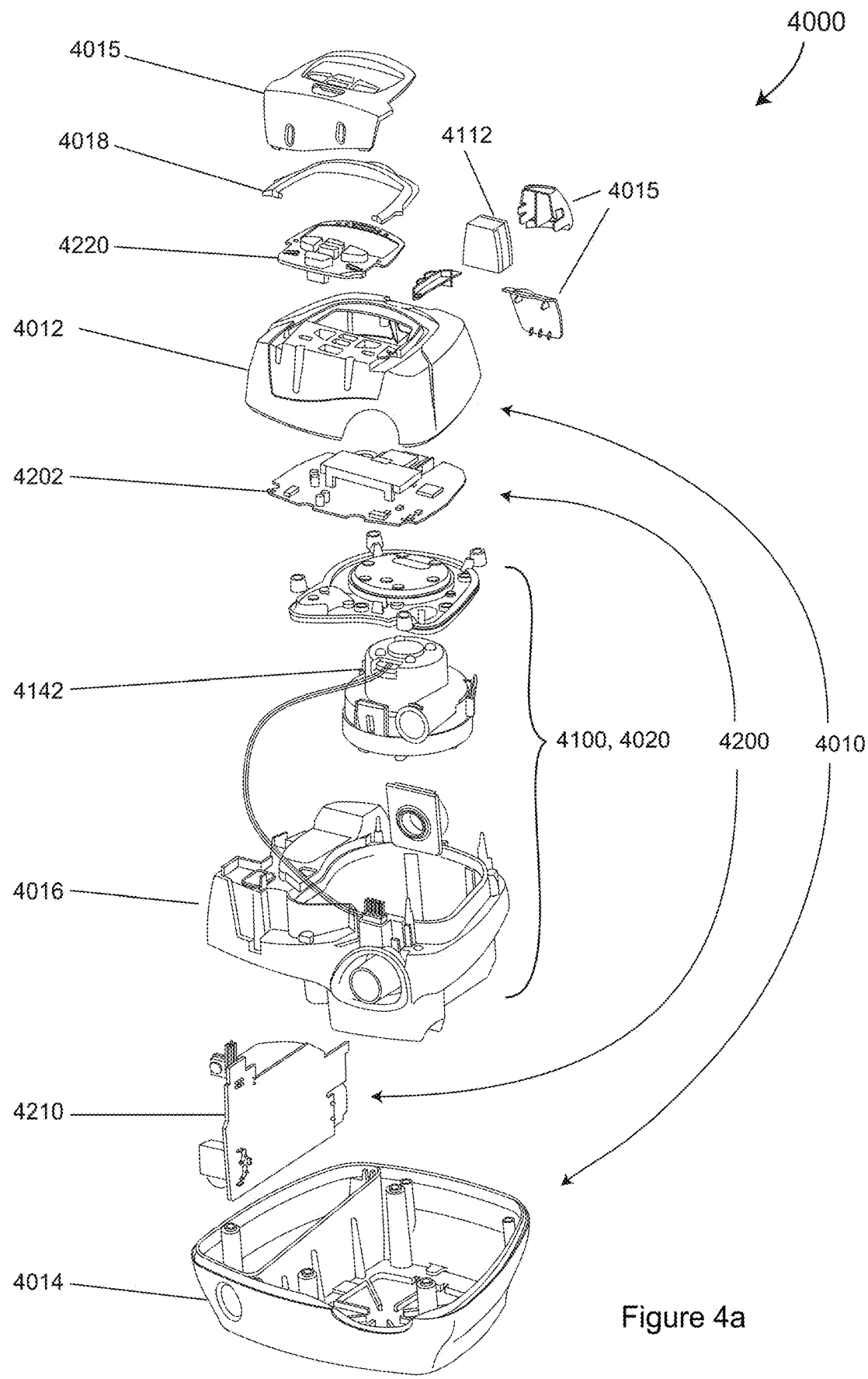

FIG. 4a shows a RPT device in accordance with one form of the present technology.

Figure 4B:
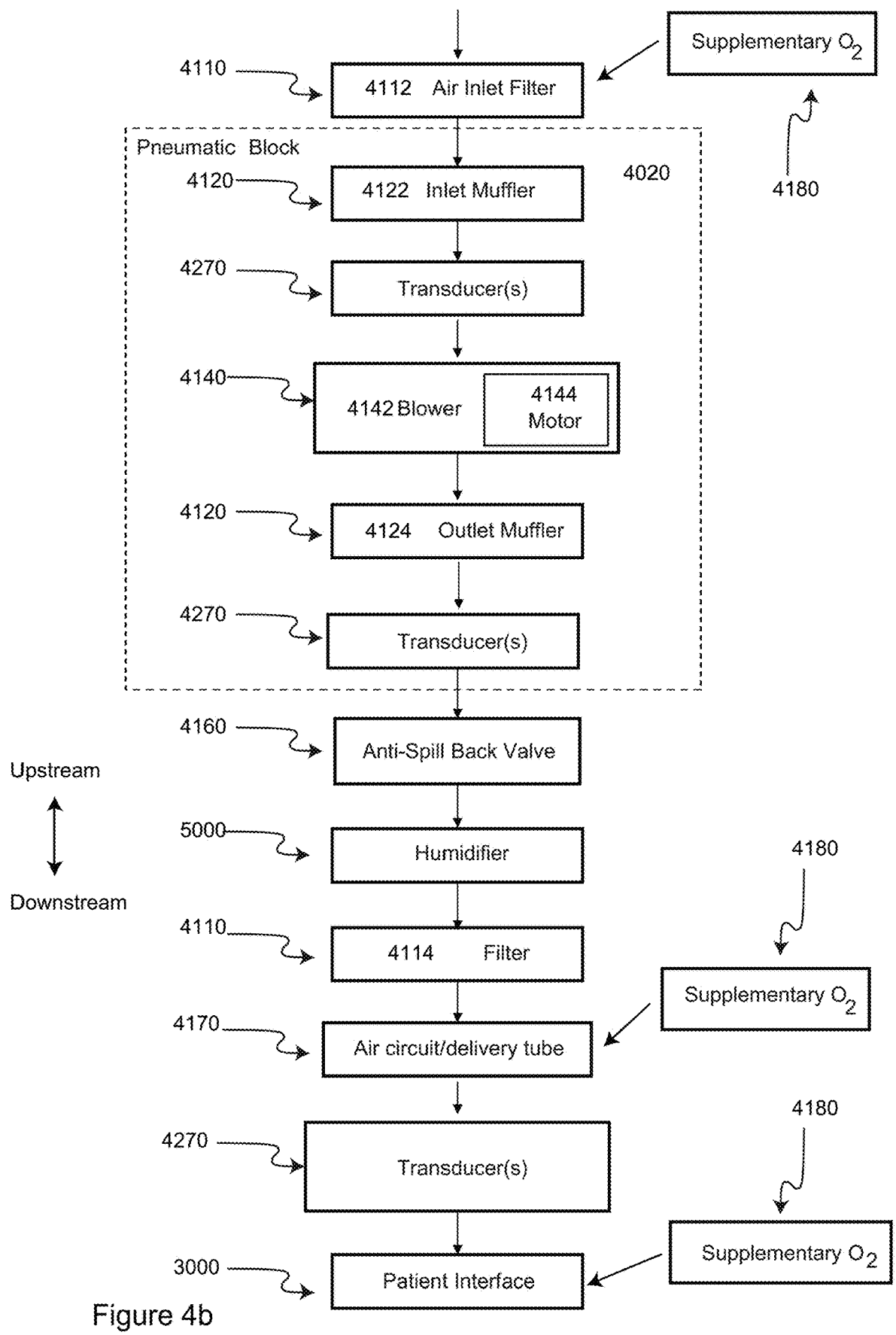

FIG. 4b shows a schematic diagram of the pneumatic circuit of a RPT device in accordance with one form of the present technology. The directions of upstream and downstream are indicated.

Figure 4C:
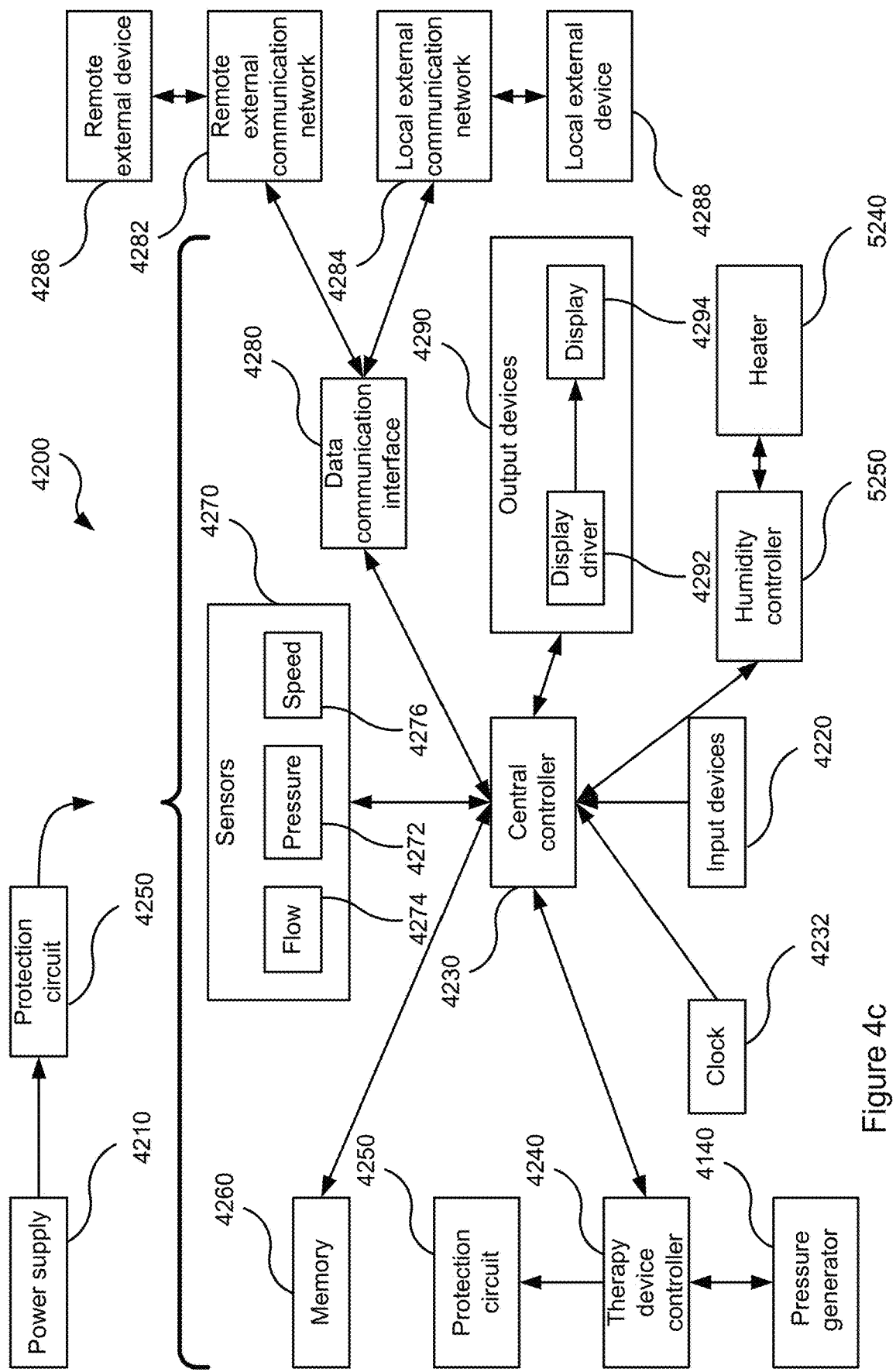

FIG. 4c shows a schematic diagram of the electrical components of a RPT device in accordance with one aspect of the present technology.

Figure 4D:
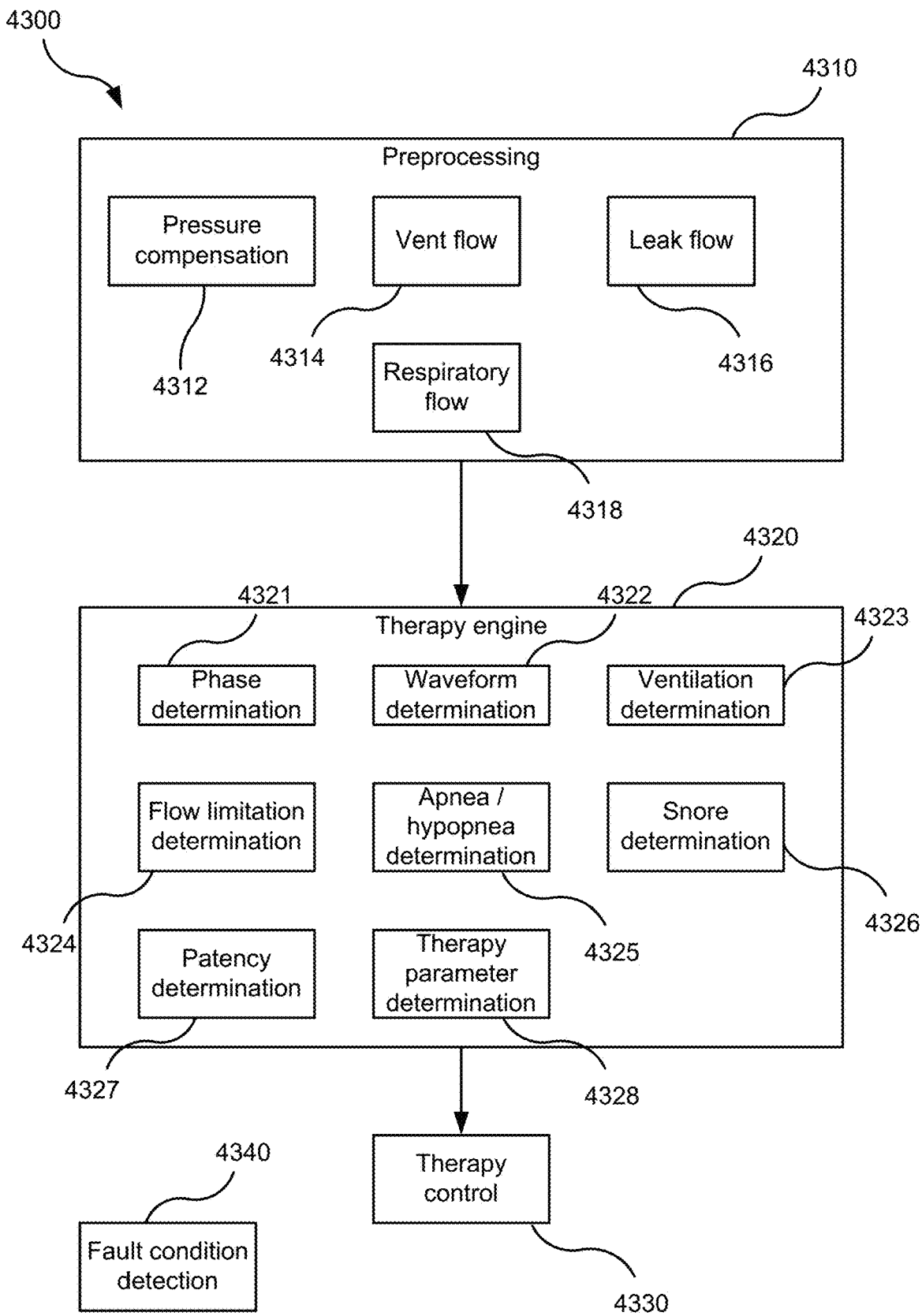

FIG. 4d shows a schematic diagram of the algorithms implemented in a RPT device in accordance with an aspect of the present technology. In this figure, arrows with solid lines indicate an actual flow of information, for example via an electronic signal.

Figure 4E:
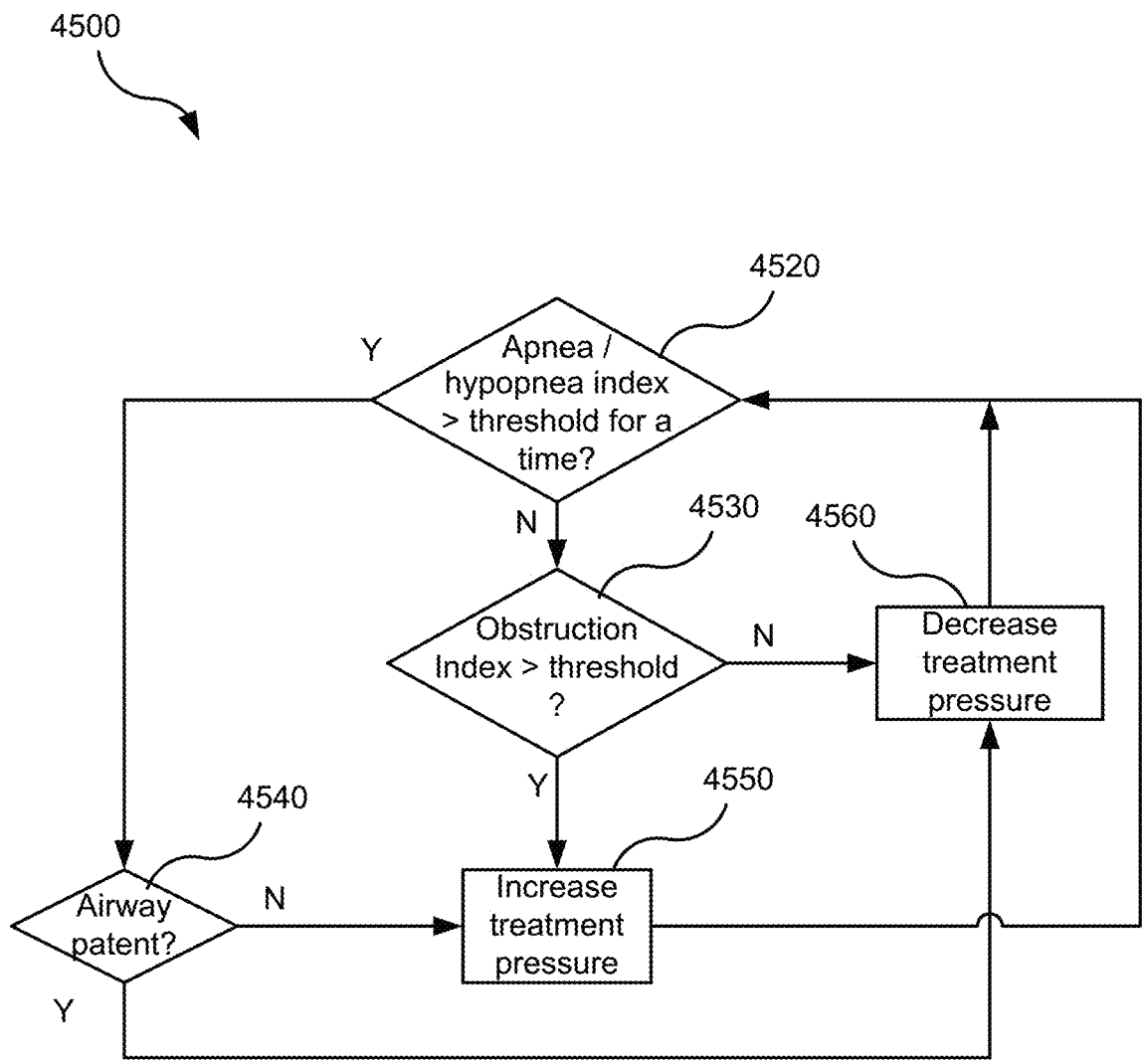

FIG. 4e is a flow chart illustrating a method carried out by the therapy engine of FIG. 4d in accordance with one aspect of the present technology.

4.5 Humidifier

FIG. 5a shows a simplified representation of a humidifier connected to a pressure generator 4140 via an air circuit 4170.

FIG. 5b shows a schematic of a humidifier.

4.6 Breathing Waveforms

Figure 6A:
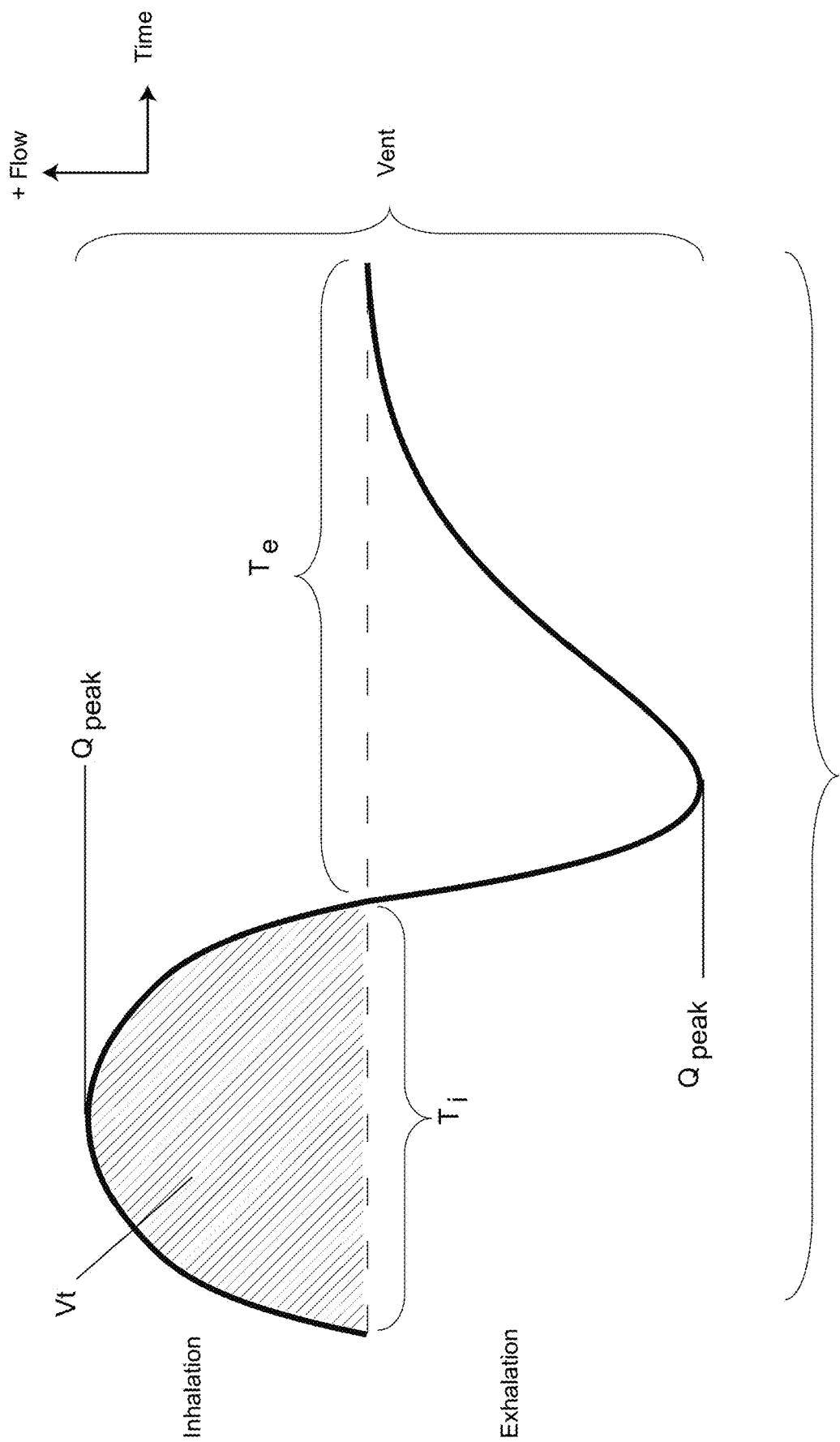

FIG. 6a shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

4.7 RPT Device with a Humidifier

Figure 7:
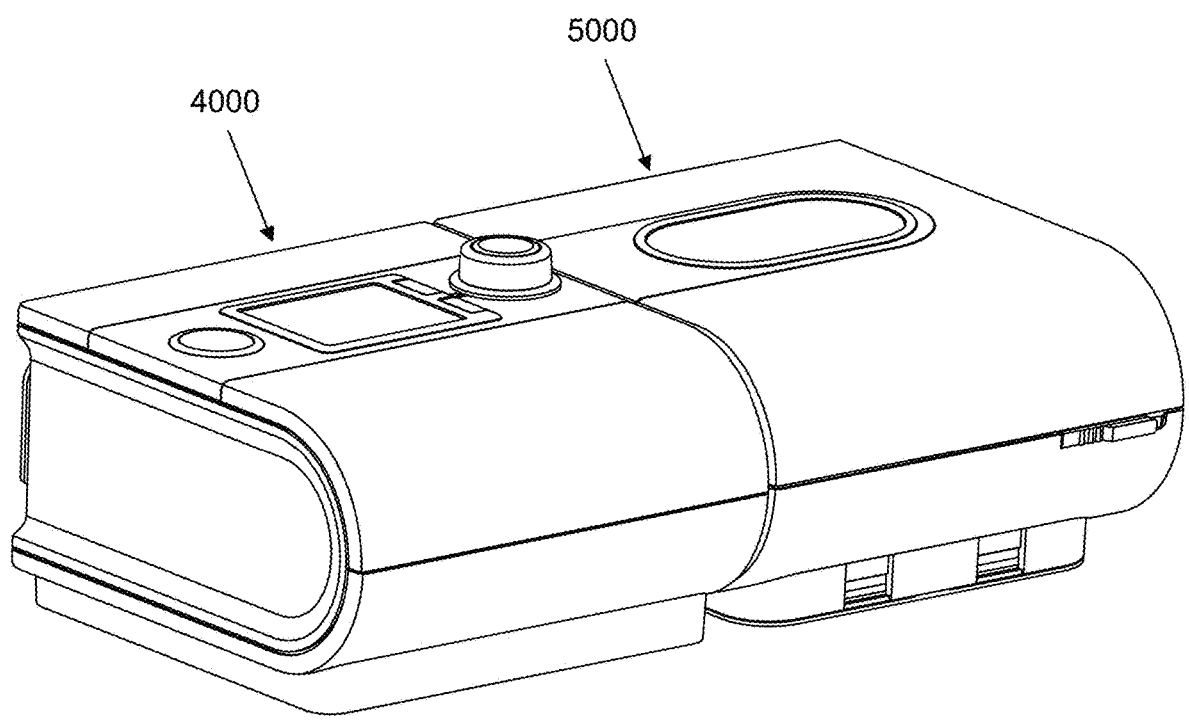

FIG. 7 shows a prior art example of a RPT device 4000 and a humidifier 5000.

Figure 8:
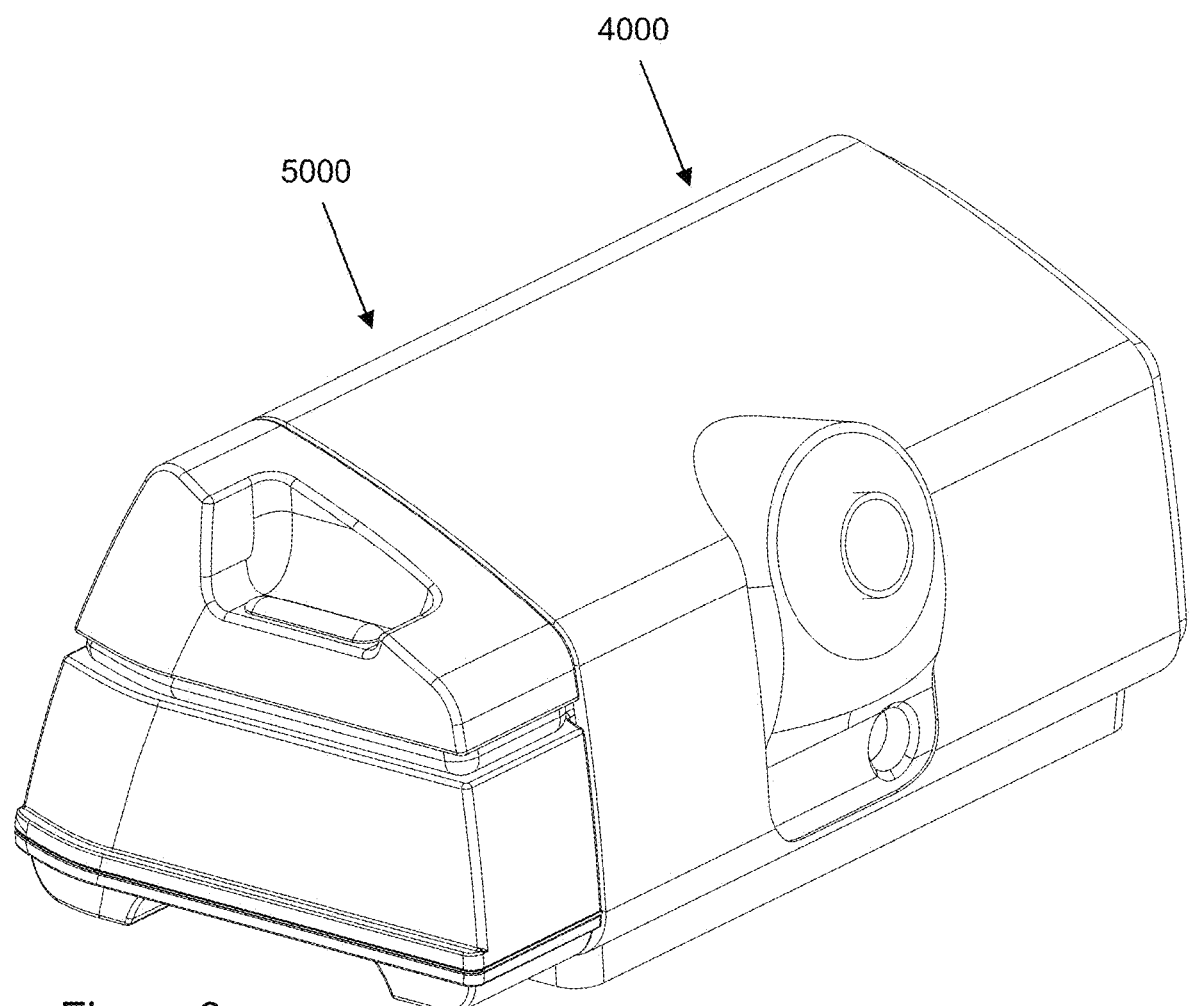

FIG. 8 shows a RPT device 4000 and an integrated humidifier 5000 according to an example of the present technology.

Figure 9:
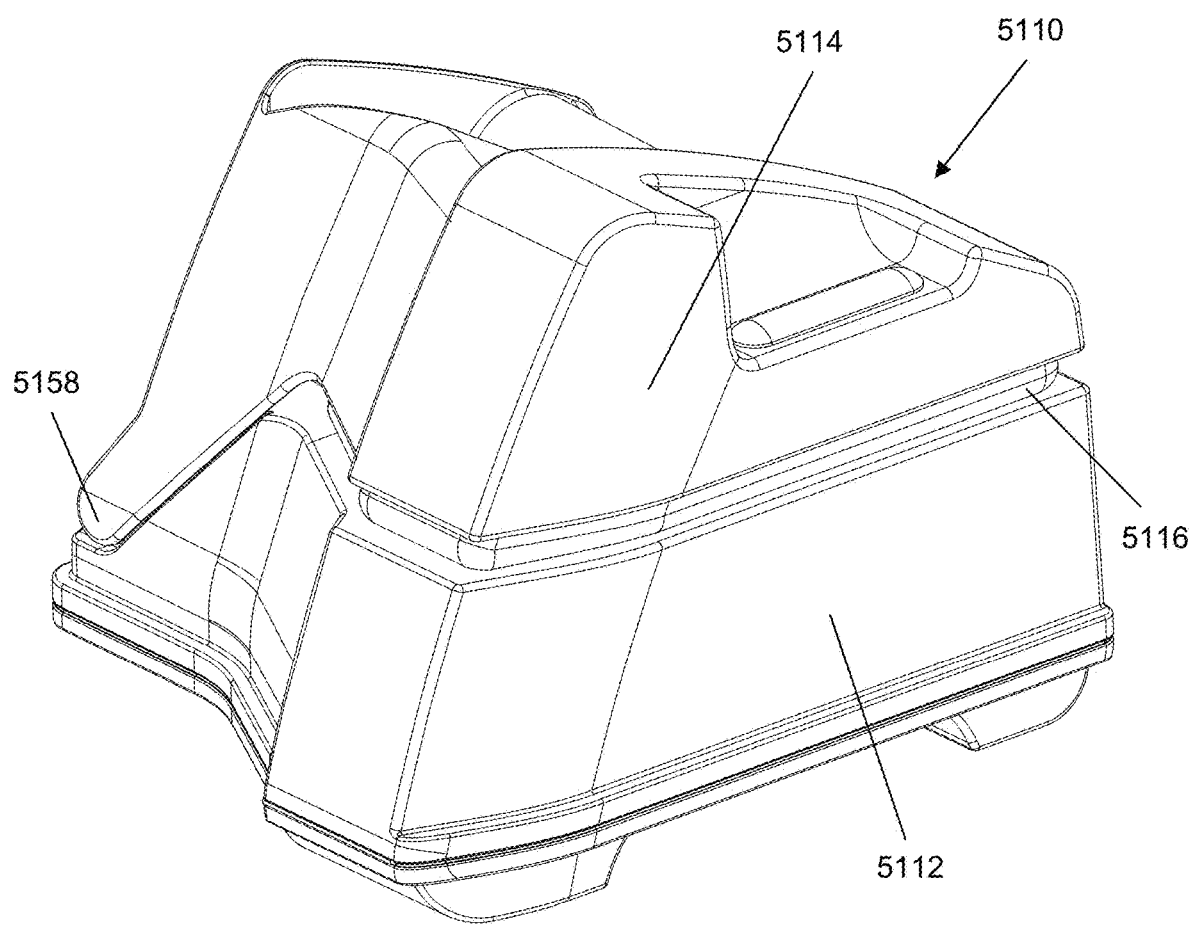
Figure 10:
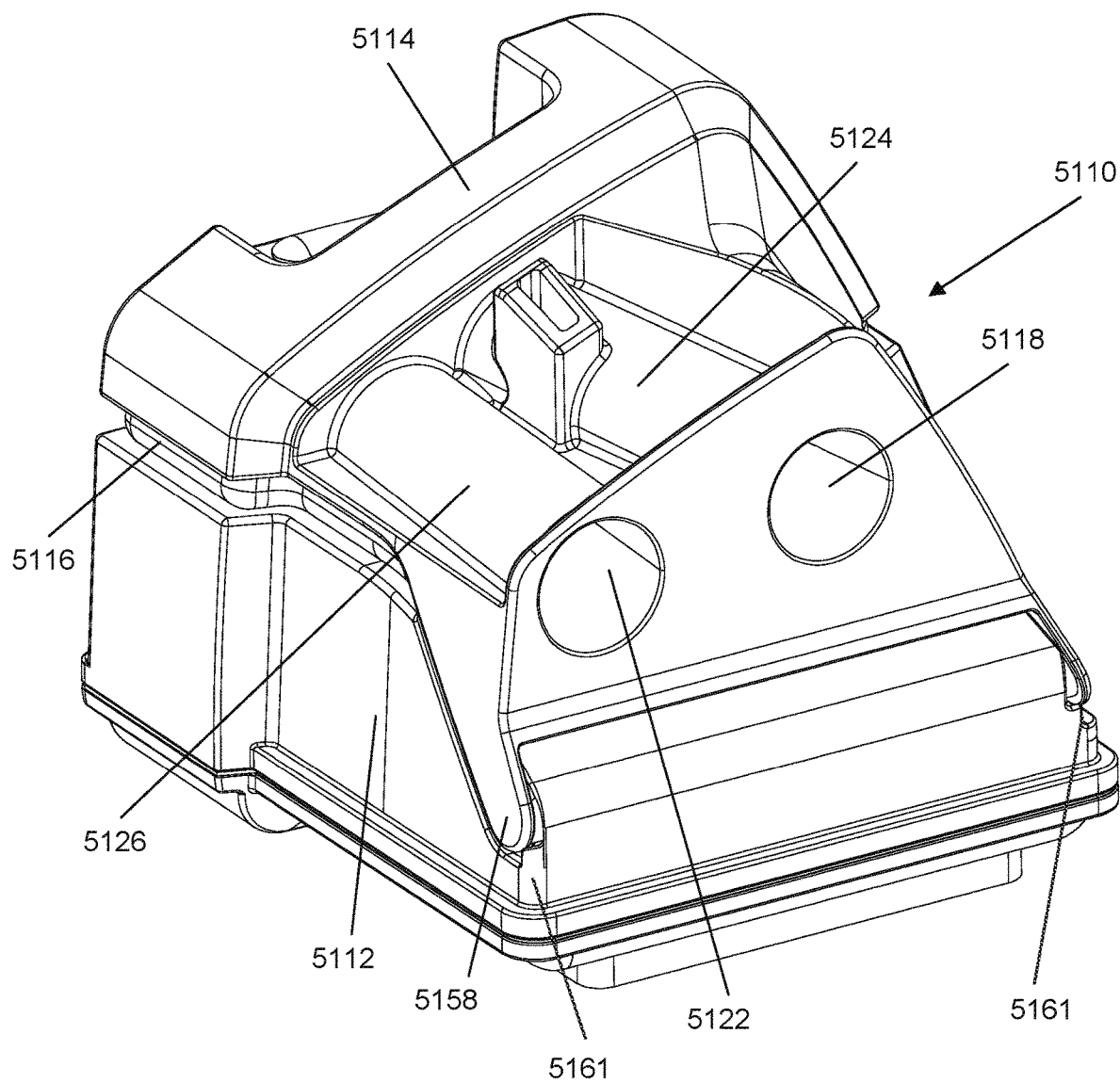
Figure 11:
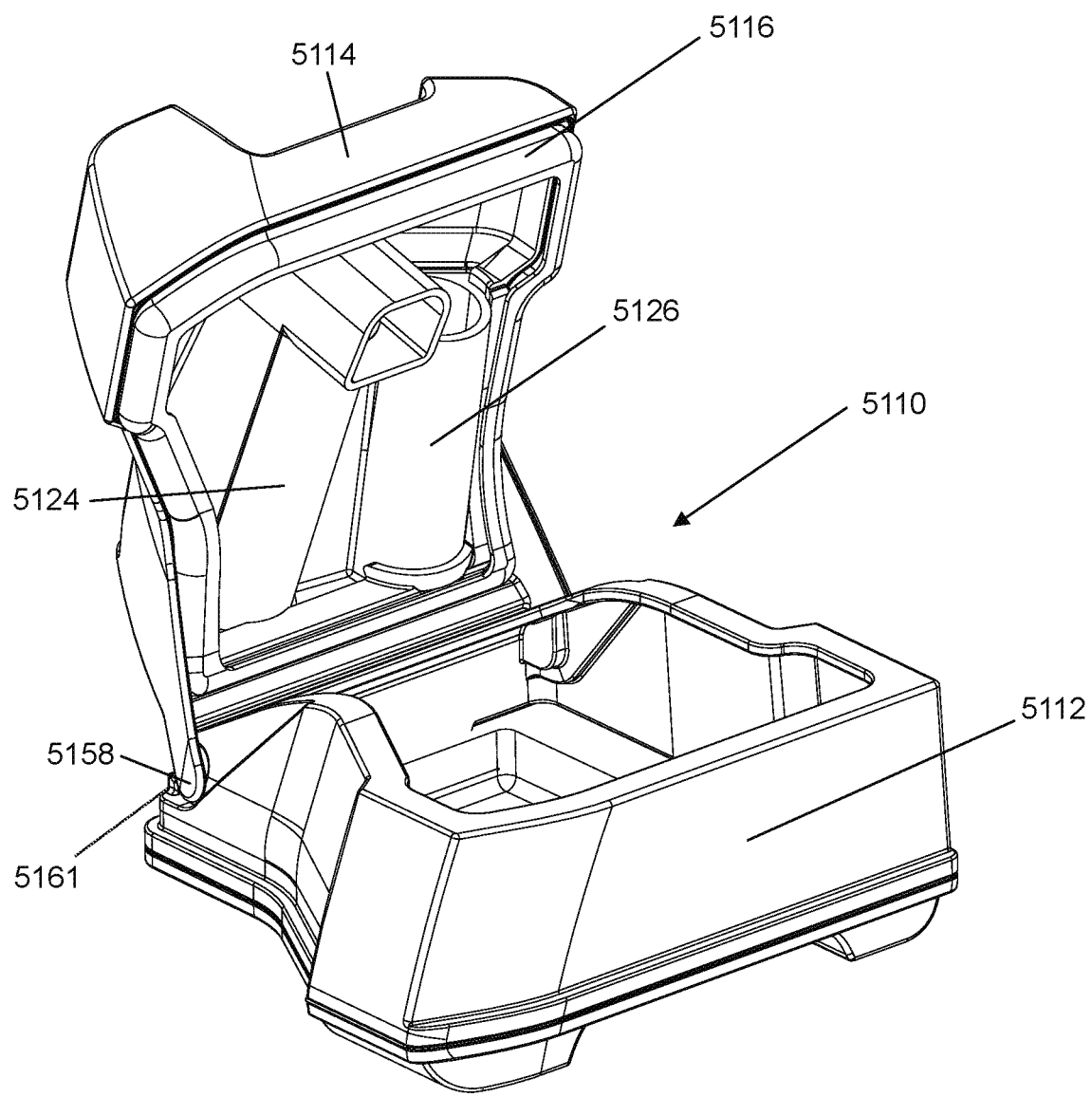
Figure 12:
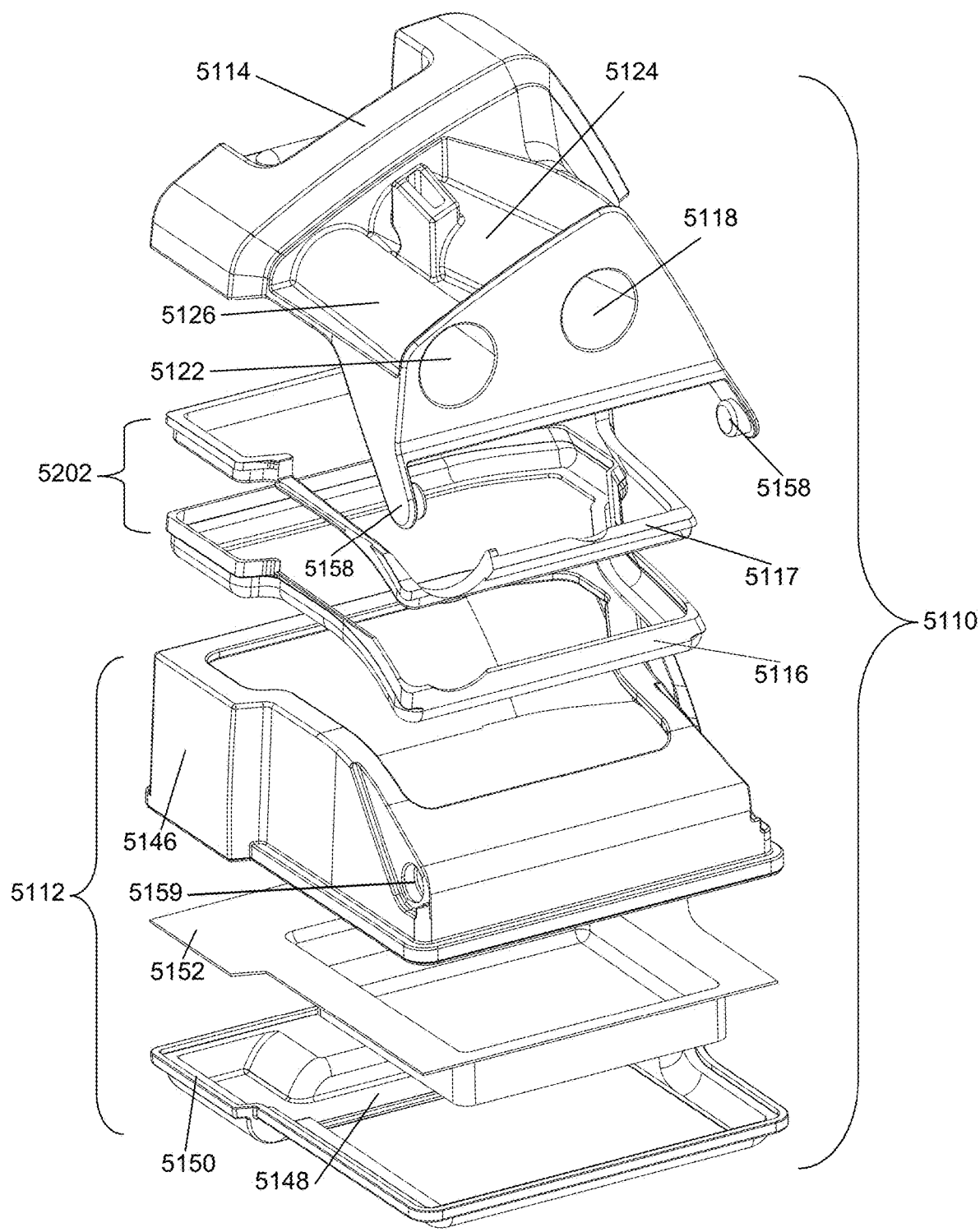

FIGS. 9 to 12 show various views of a humidifier reservoir 5110 in accordance with an example of present technology, wherein FIGS. 9 to 10 show the humidifier reservoir 5110 in a 'closed' configuration, FIG. 11 shows the humidifier reservoir 5110 in an 'open' configuration and FIG. 12 is an exploded view of the humidifier reservoir 5110.

FIGS. 13 to 16 show the humidifier 5000 from various perspectives, demonstrating the engagement of the humidifier reservoir 5110 with the reservoir dock 5130 and/or engagement of the humidifier 5000 with the air circuit 4170 according to an example of the present technology.

FIGS. 17a to 17c, 18a to 18c, and 19a to 19c show a time-lapse chart of an exemplary flow path of air as it enters the humidifier reservoir 5110 through the inlet 5118 (FIGS. 17a to 17c) and exits through the outlet 5122 (FIGS. 19a to 19c) after traversing through the inside of the humidifier reservoir 5110 (FIGS. 18a to 18c) according to an example of the present technology.

Figure 20:
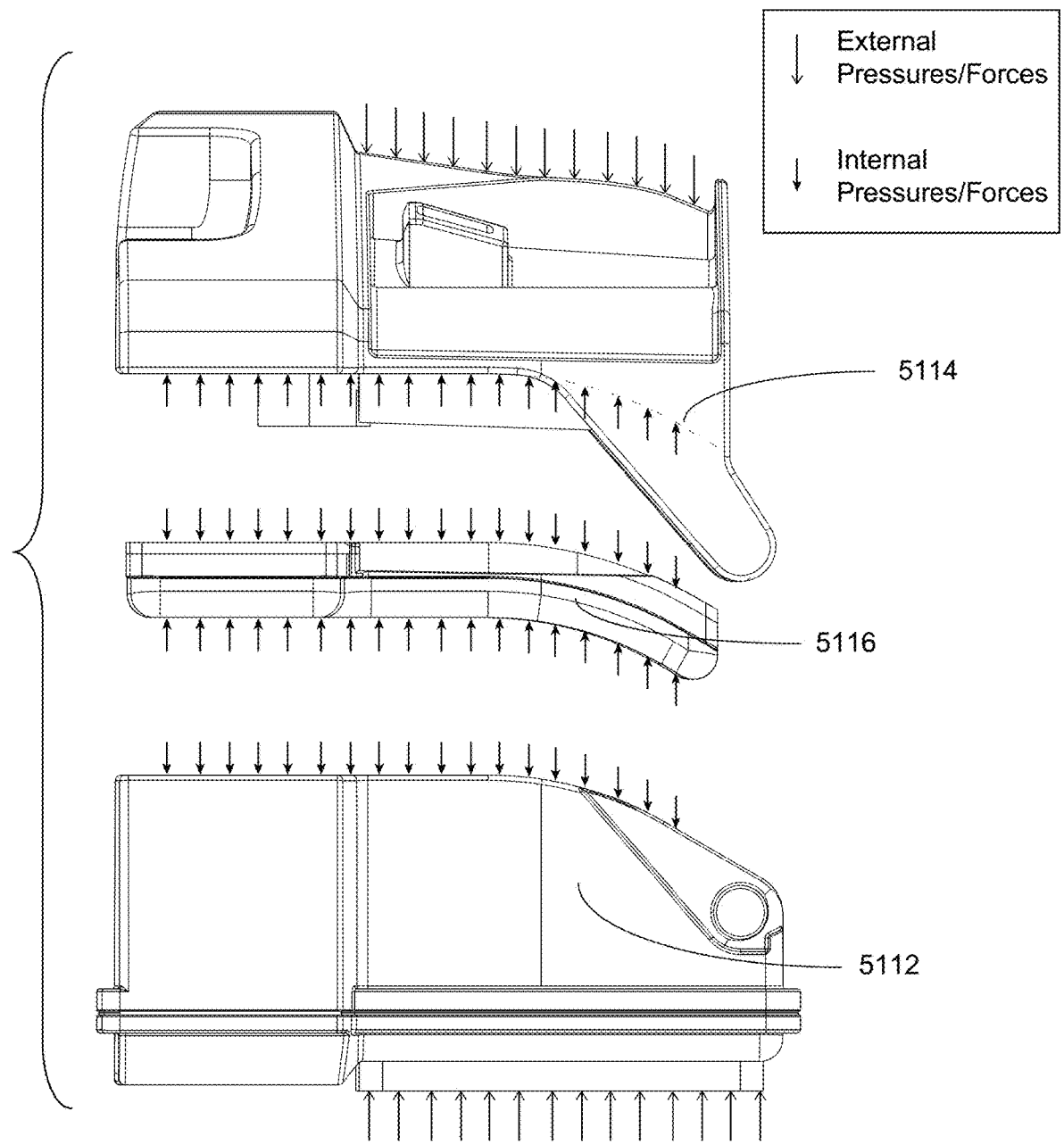
Figure 21:
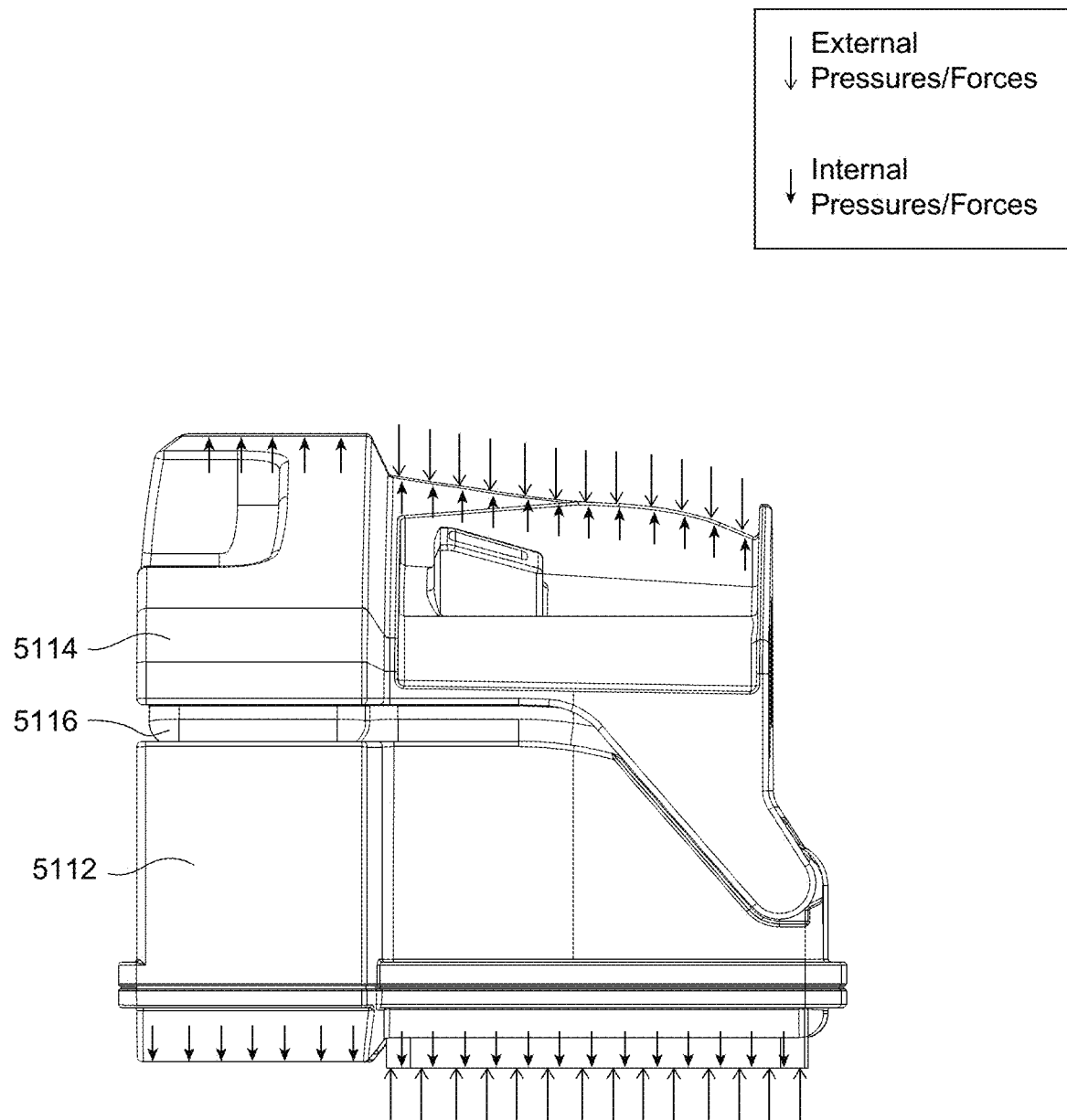

FIGS. 20 to 21 show exemplary distributions of pressure/force in the humidifier reservoir 5110 in various configurations according to an example of the present technology.

FIGS. 22 to 29 show varying configurations of the reservoir lid 5114, in particular variations in configurations of the inlet tube 5124 and the outlet tube 5126 according to examples of the present technology.

Figure 30A:
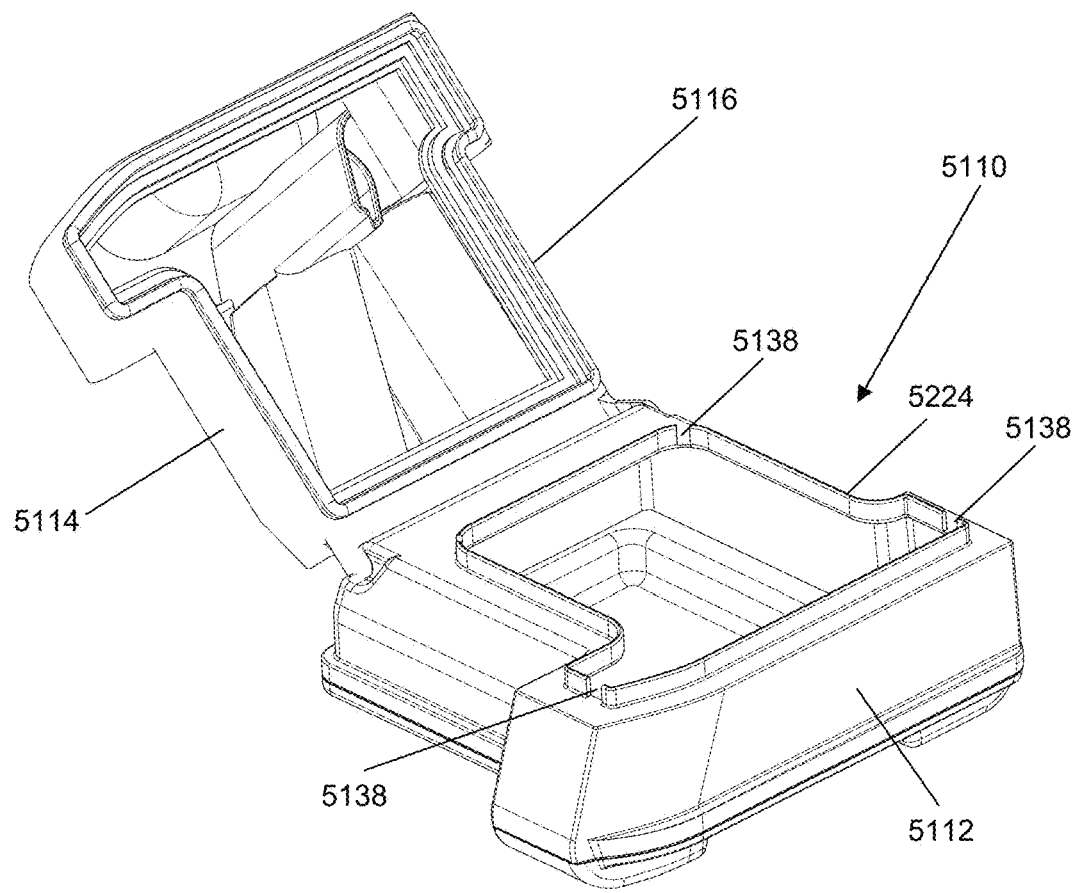
Figure 30B:
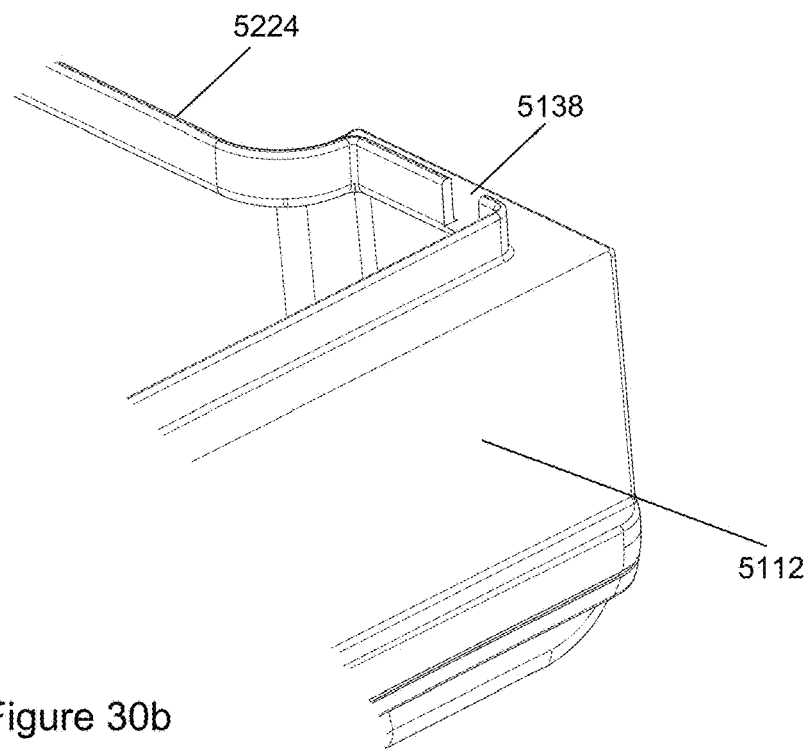

FIGS. 30a and 30b show the humidifier reservoir 5110 and in particular the orifices 5138 according to an example of the present technology.

Figure 30C:
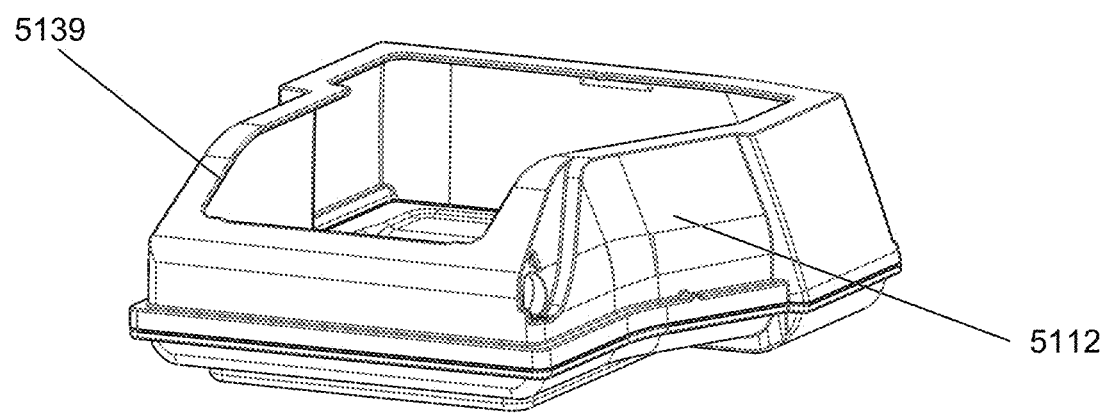
Figure 30D:
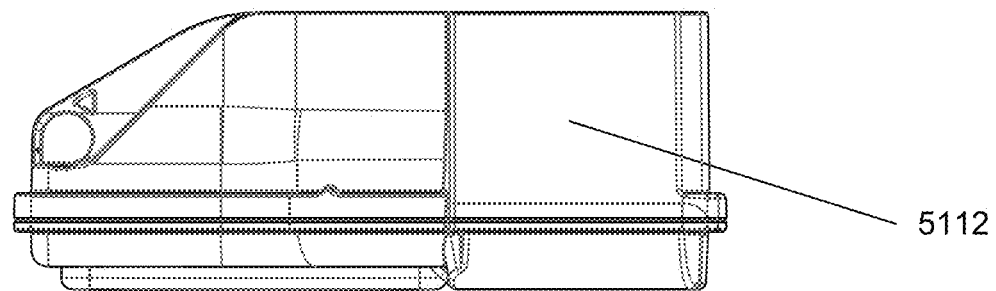

FIGS. 30c and 30d show the humidifier reservoir base 5112 and in particular the sloped profile 5139 according to an example of the present technology.

Figure 31A:
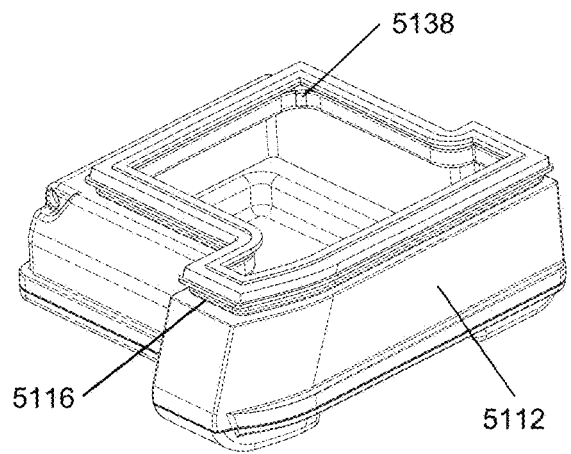

FIG. 31a shows the humidifier reservoir 5110 and in particular the orifice 5138 according to an example of the present technology.

Figure 31B:
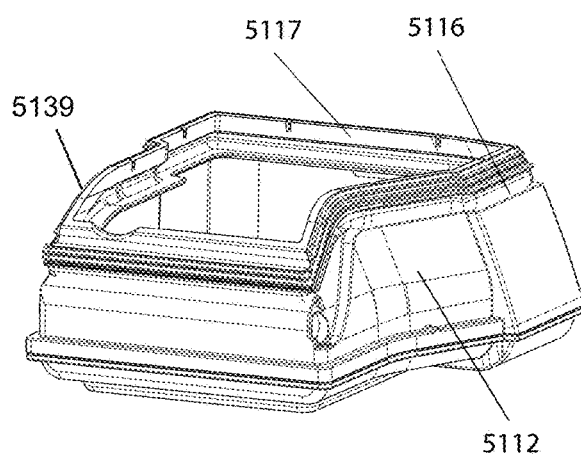

FIG. 31b shows the humidifier reservoir 5110 and in particular the sloped profile 5139 according to an example of the present technology.

Figure 32:
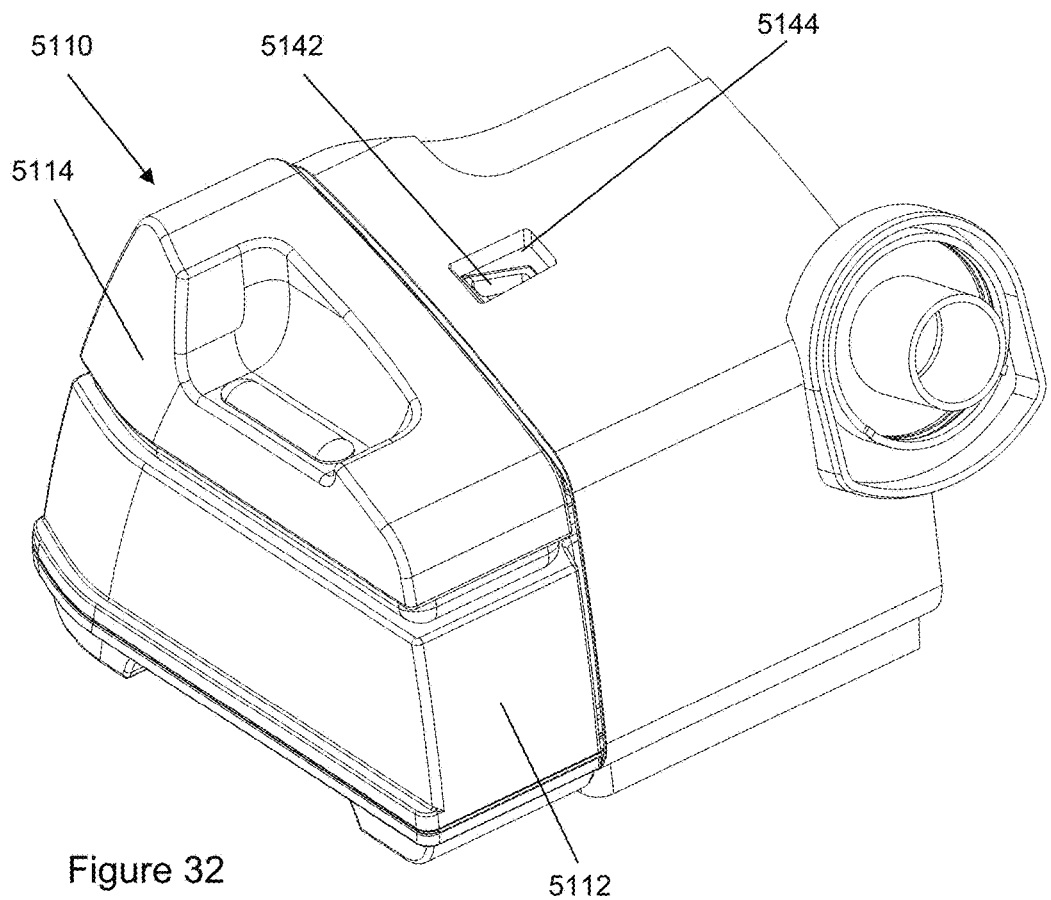
Figure 33:
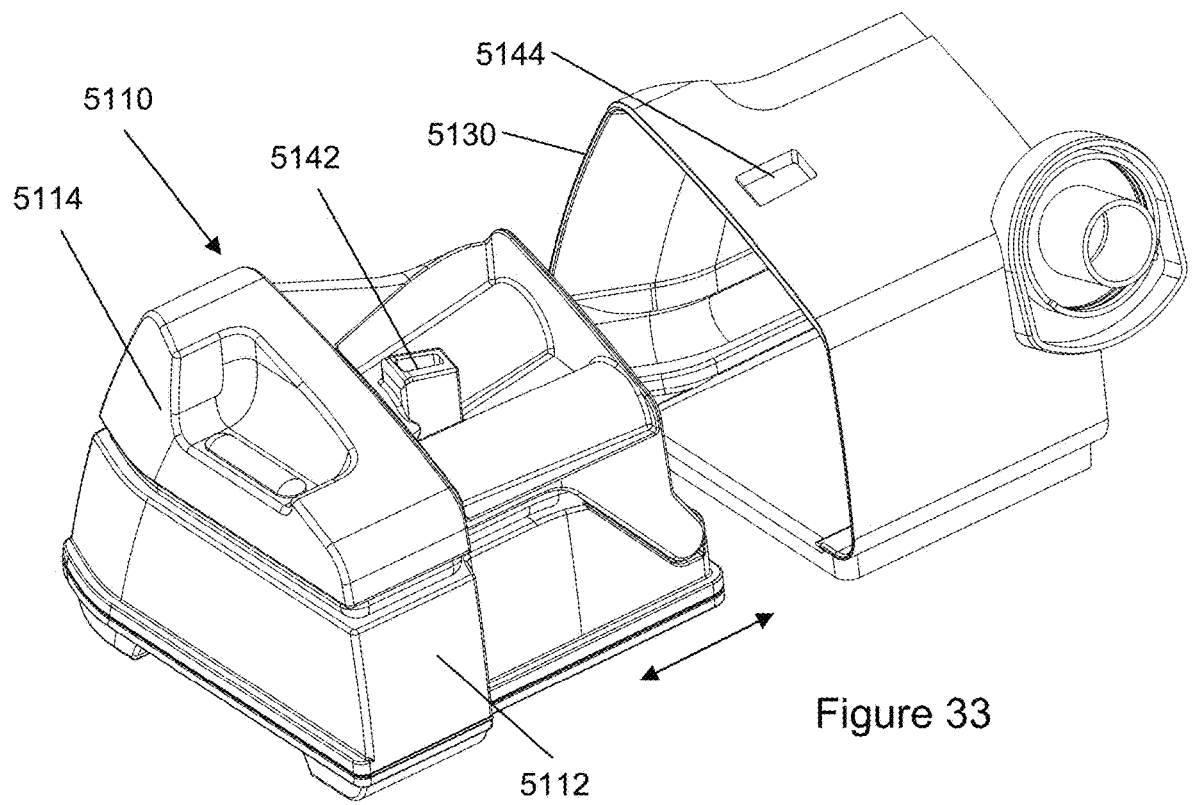

FIGS. 32 to 33 show the humidifier dock 5130 and the humidifier reservoir 5110, and in particular show the interaction between the lid retention protrusion 5142 and the dock locking recess 5144 according to an example of the present technology.

Figure 34:
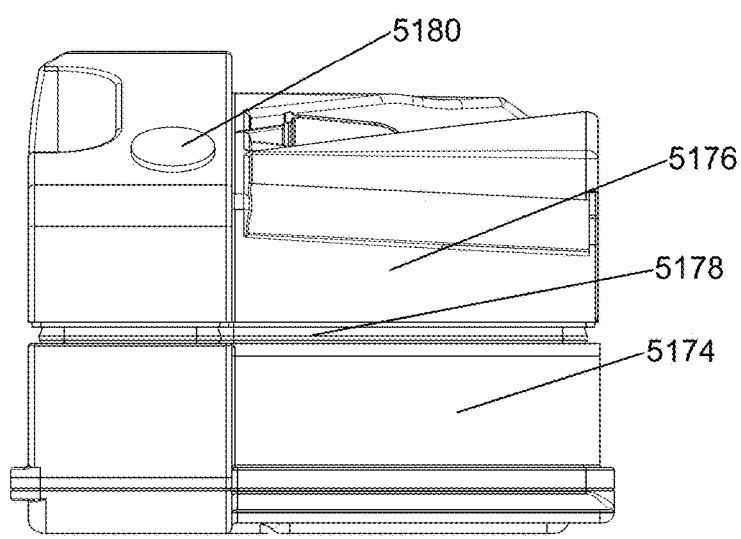

FIG. 34 shows the humidifier reservoir 5110 according to another example of the present technology, wherein it is configured with a re-filling cap 5180 and a base, top and compliant portion may be affixed together.

FIGS. 35 to 38 show other representations of a humidifier reservoir 5110 according to an example of the present technology, with particular regard to the arrangement of the inlet tube 5124 and the outlet tube 5126.

Figure 39:
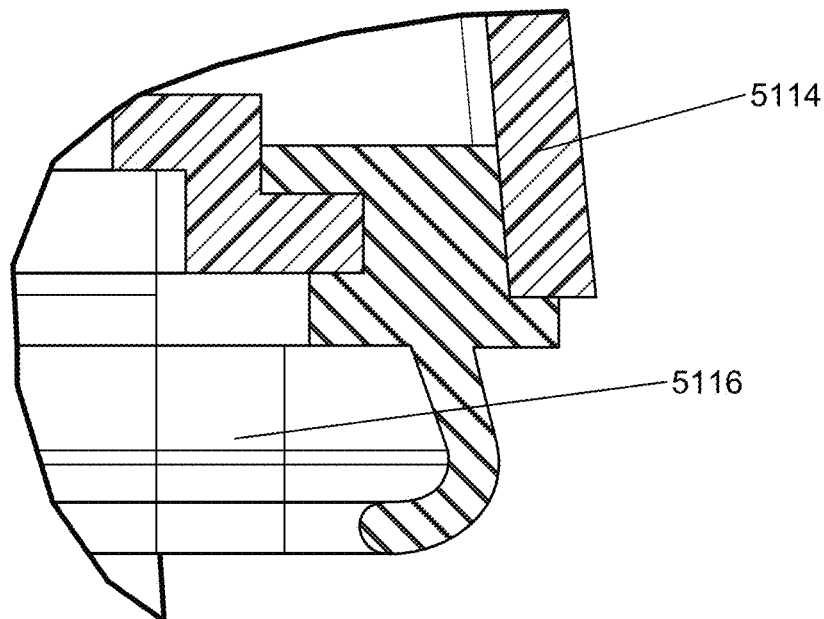

FIG. 39 shows a cross-sectional view of a reservoir lid 5114 and a compliant portion 5116 according to an example of the present technology.

Figure 40:
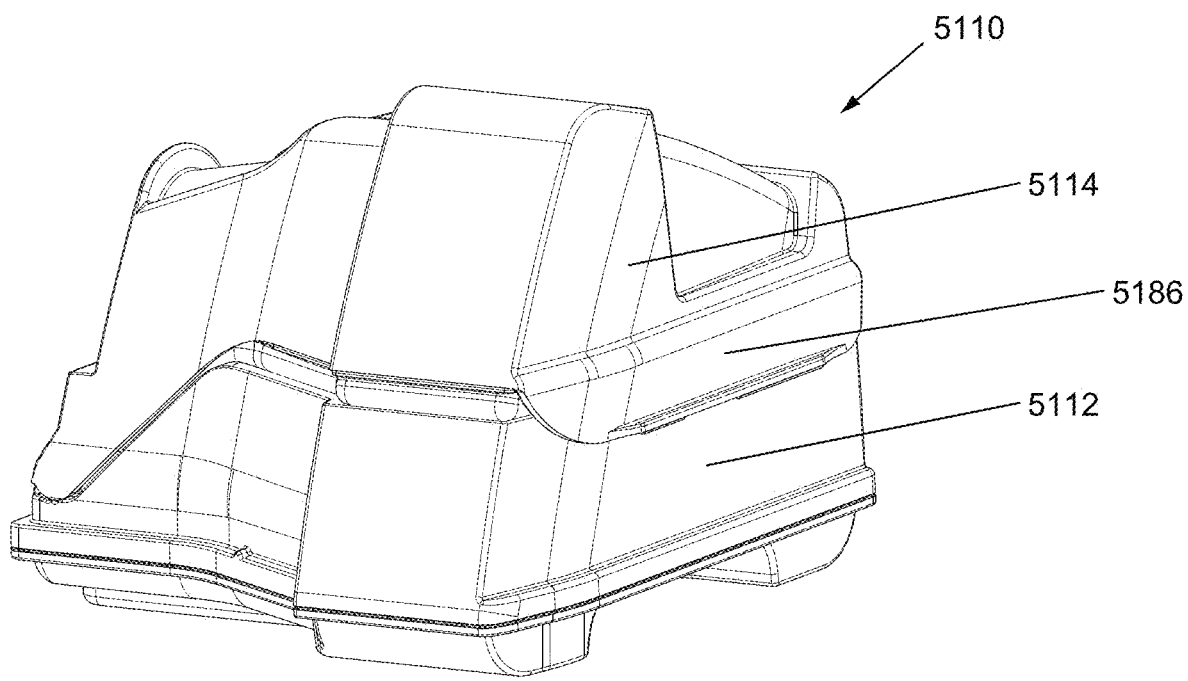

FIG. 40 shows an example of the humidifier reservoir 5110 according to another example of the present technology, wherein it is configured with a latch 5186.

Figure 41A:
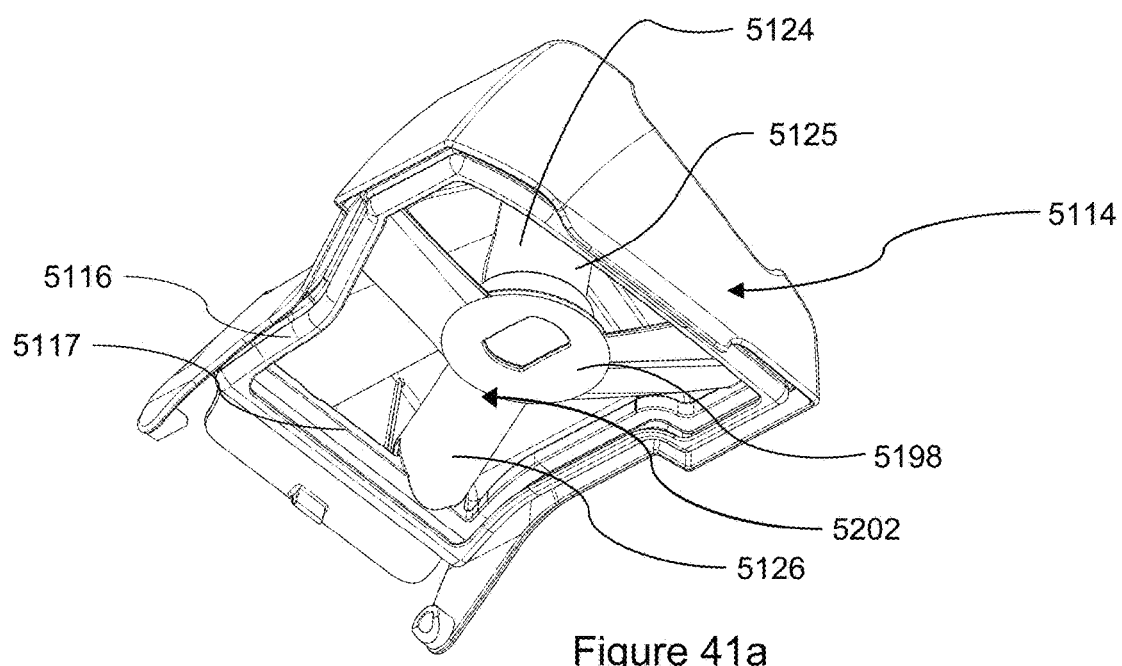
Figure 41B:
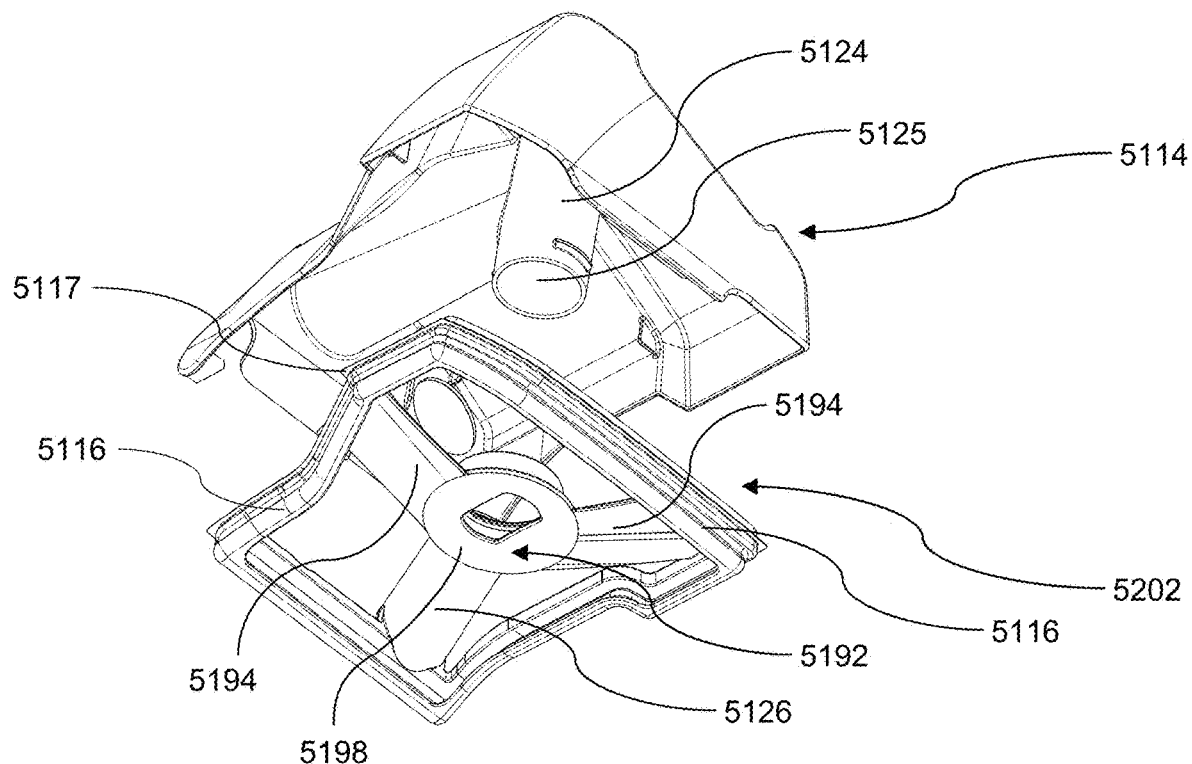
Figure 42:
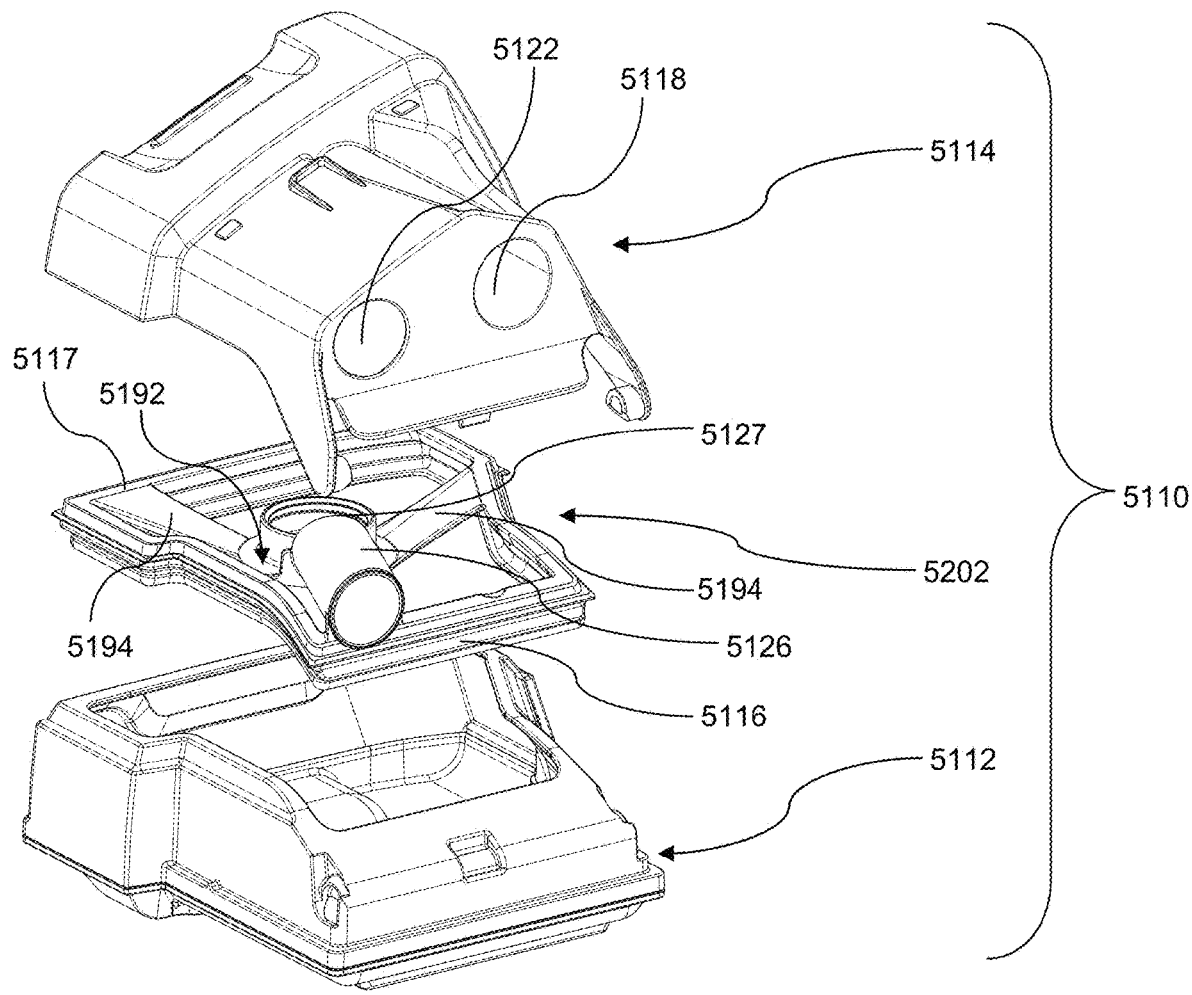

FIGS. 41a, 41b, and 42 show a humidifier reservoir 5110 according to another example of the present technology. In this configuration, the reservoir 5110 comprises a reservoir lid 5114 including an inlet tube 5124, a base portion 5112 (as seen in an exploded view shown in FIG. 42) and an intermediate portion 5202 which comprises an outlet tube 5126.

Figure 43A:
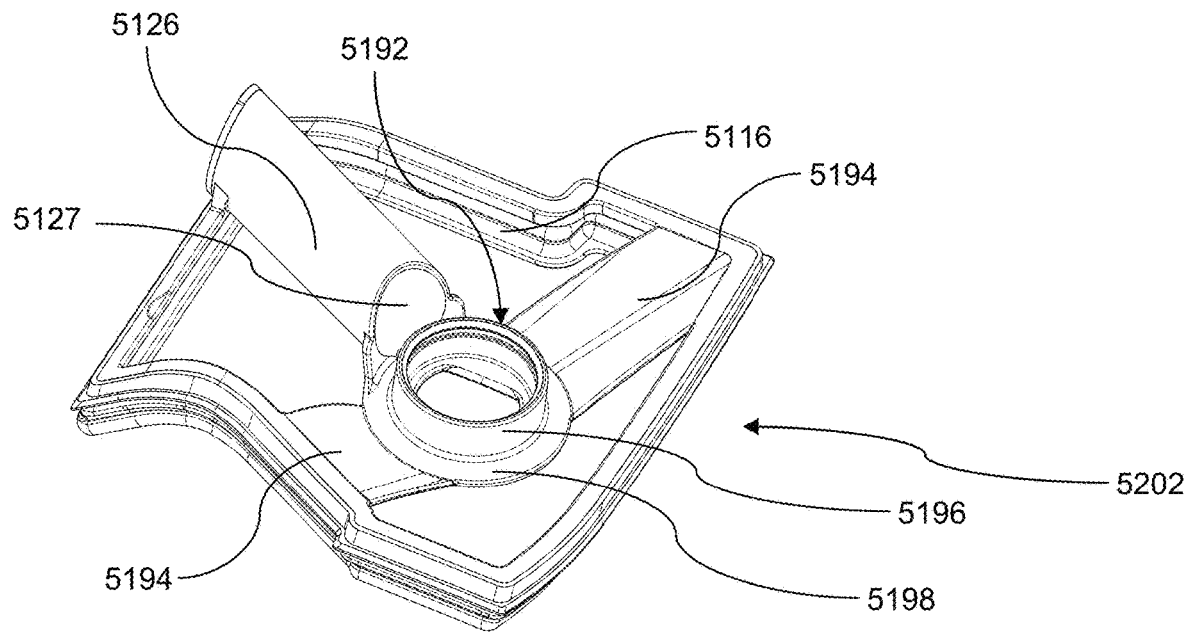
Figure 43B:
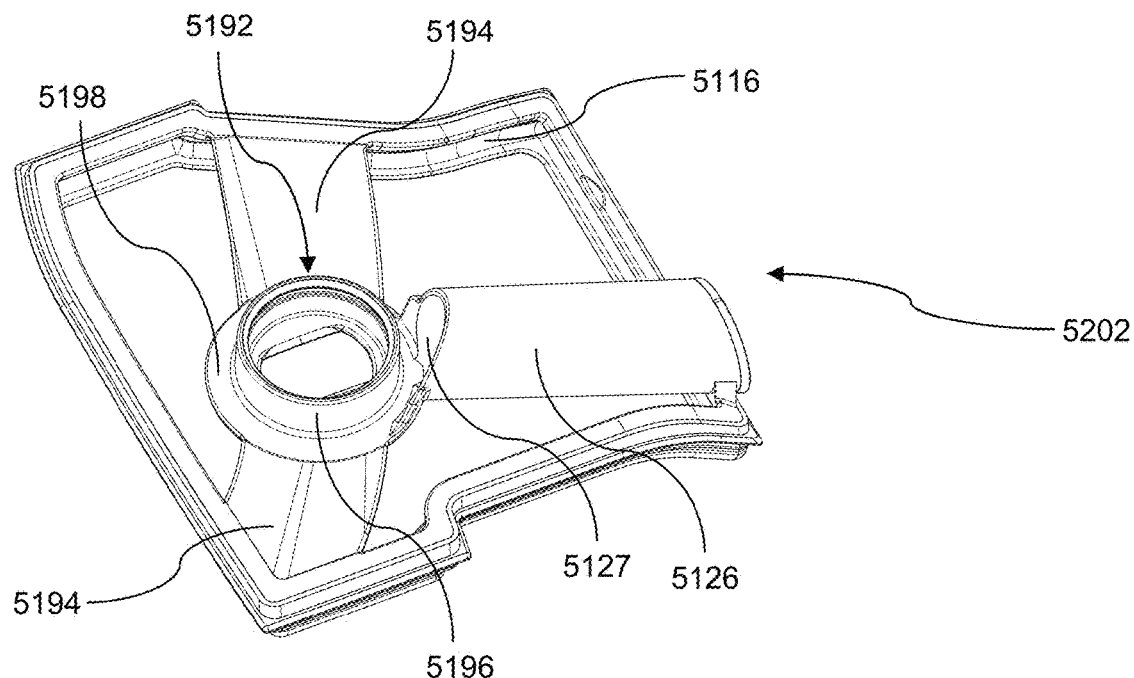

FIGS. 43a and 43b show the intermediate portion 5202 of the reservoir 5110 from various angles according to an example of the present technology. In particular they aim to show the baffle 5192, the outlet tube 5126 and the support spokes 5194.

Figure 44:
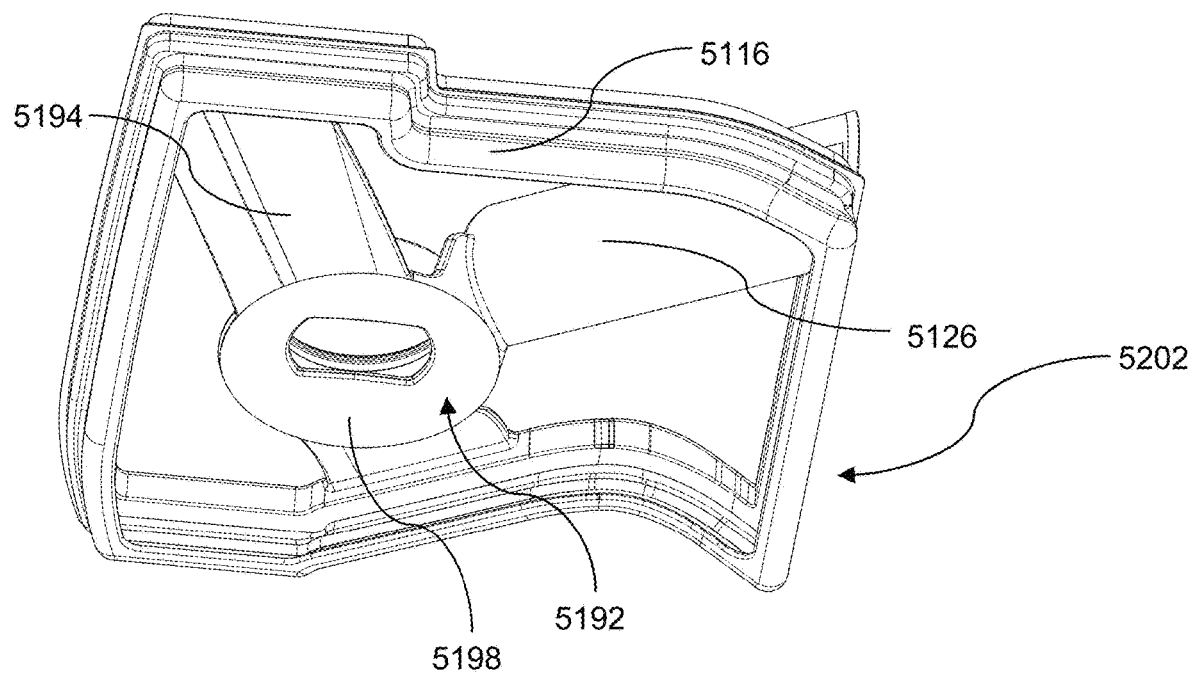

FIG. 44 shows a perspective bottom view of the intermediate portion 5202 of the reservoir 5110 according to an example of the present technology.

FIGS. 45a and 45b show a cross section of the reservoir lid 5114 and the intermediate portion 5202 connected together, and FIG. 45c shows the reservoir lid 5114 indicating a cross section shown in FIGS. 45a and 45b, according to an example of the present technology. FIG. 45b shows the cross section of the baffle 5192 in further detail, in particular the arrangement of the vertical portion of the inlet tube 5124, the locating portion 5196 of the baffle 5192 and the deflector portion 5198 of the baffle 5192.

Figure 46:
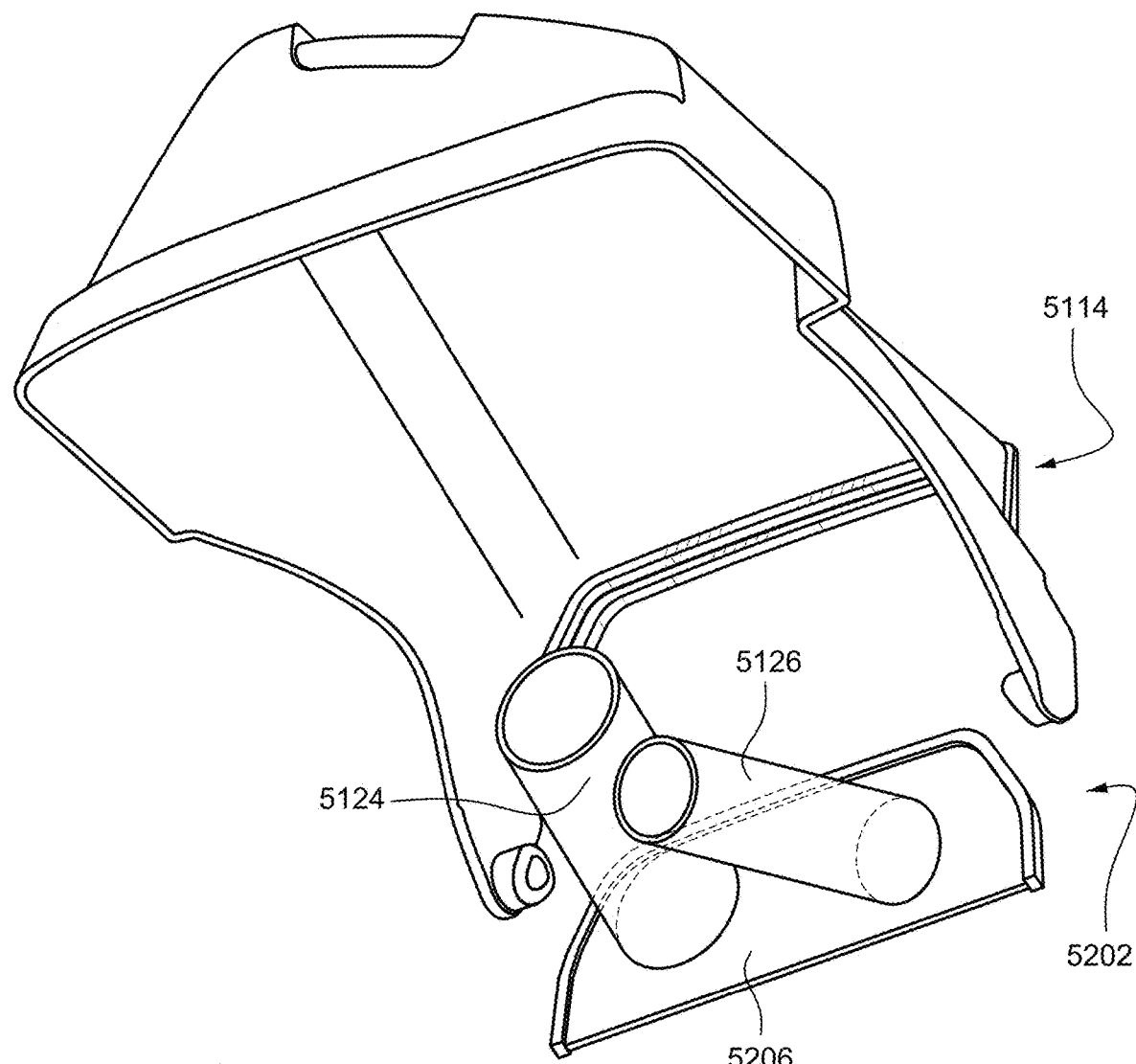

FIG. 46 shows an upper portion of the humidifier reservoir 5110 according to another example of the present technology. In this configuration, the reservoir 5110 comprises a reservoir lid portion 5114, a base portion (not shown), and an intermediate portion 5202 that comprises an outlet tube 5126, an inlet tube 5124 as well as a wall portion 5206.

Figure 47A:
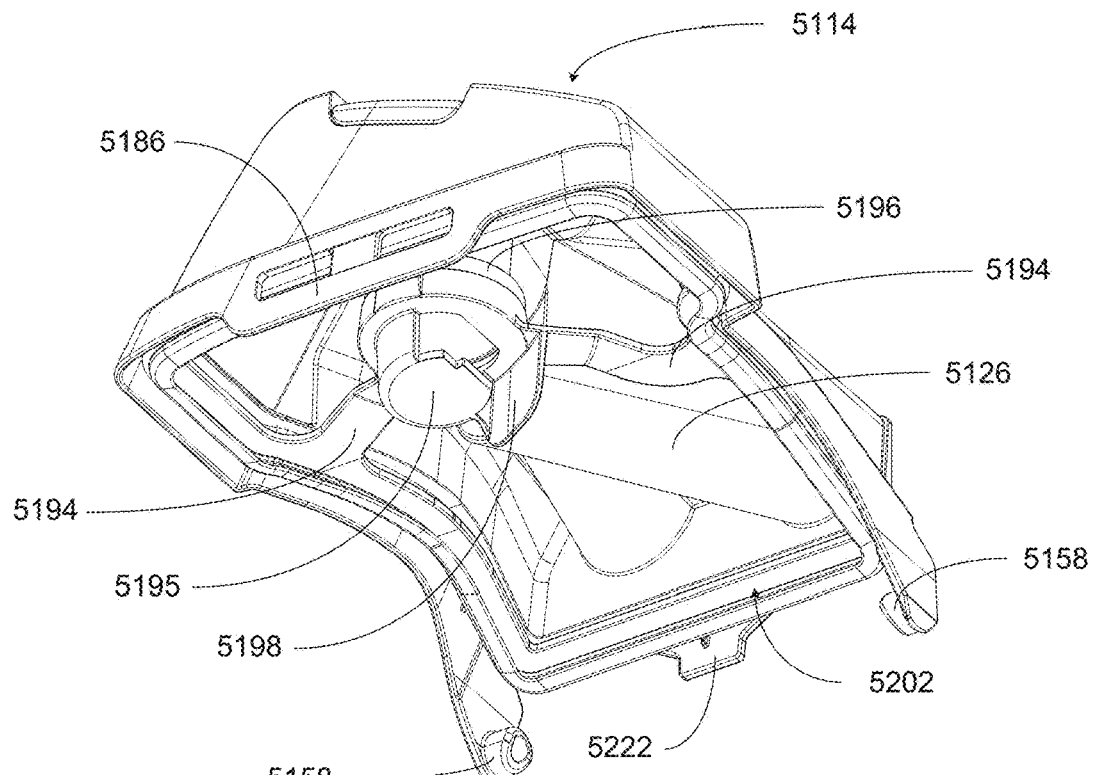
Figure 47B:
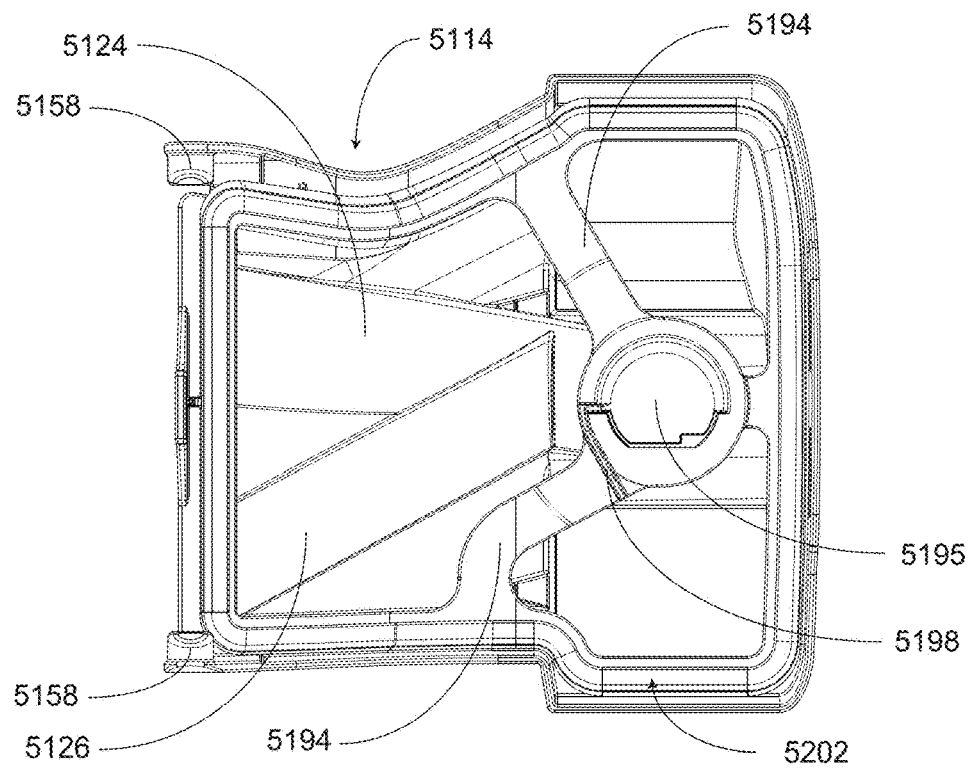

FIGS. 47a and 47b show a portion of the humidifier reservoir 5110 according to another example of the present technology. FIGS. 47a and 47b show the reservoir lid 5114 connected to the intermediate portion 5202, and in particular they aim to show the inlet tube 5124, the outlet tube 5126, the deflector portion 5198 and the flow director 5195.

Figure 48A:
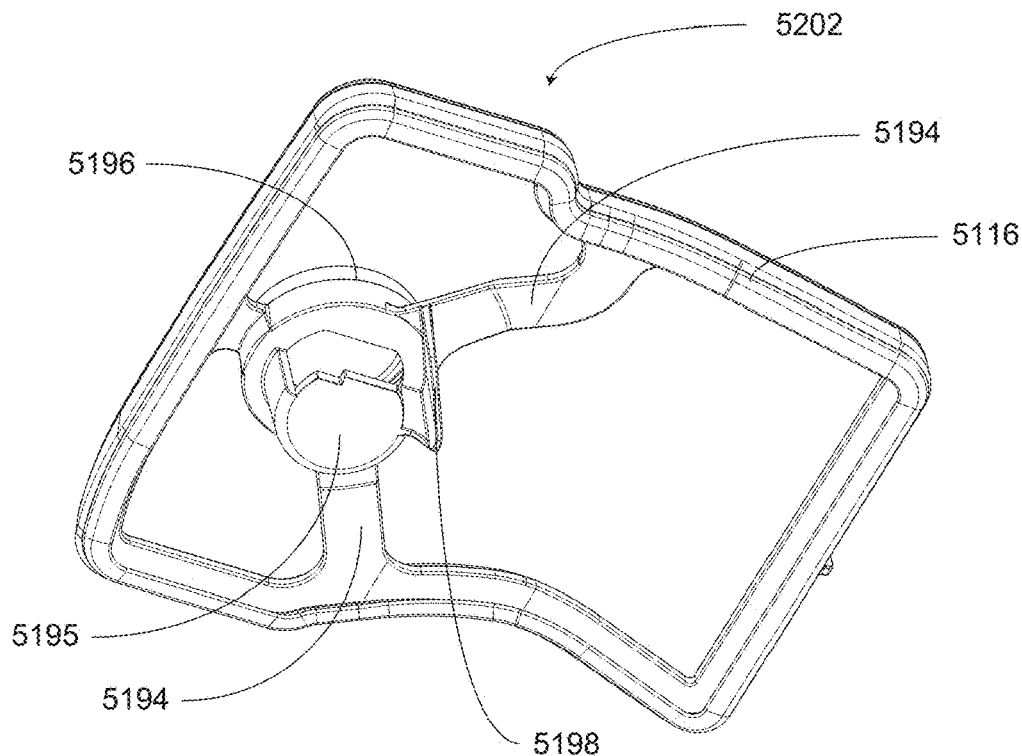
Figure 48B:
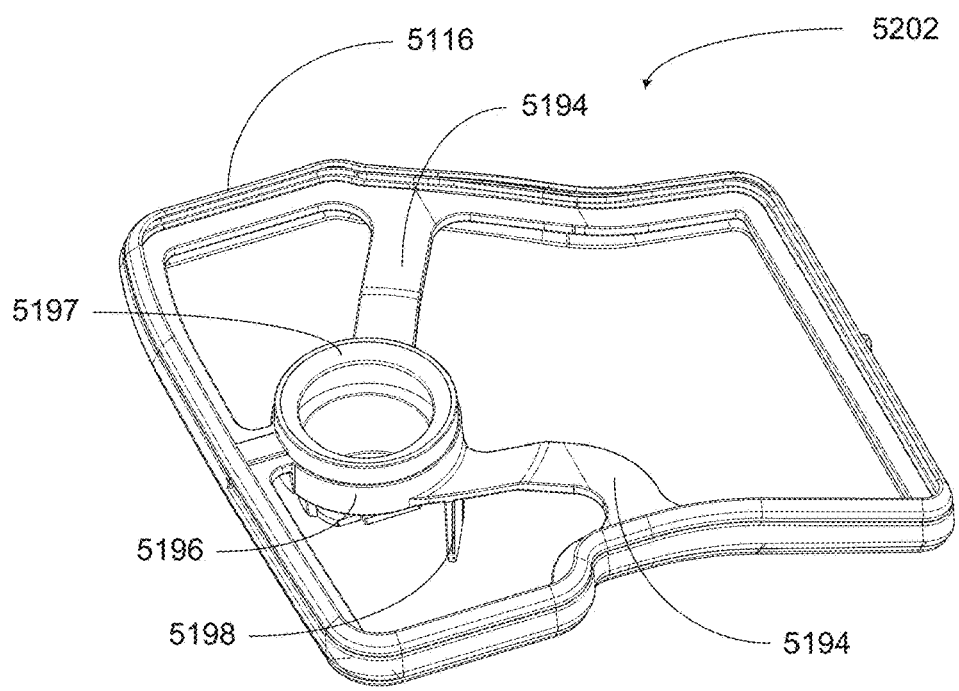

FIGS. 48a and 48b show the intermediate portion 5202 according to another example of the present technology, and in particular they aim to show the deflector portion 5198, the flow director 5195, the locating portion 5196 and the compliant portion 5116.

Figure 49:
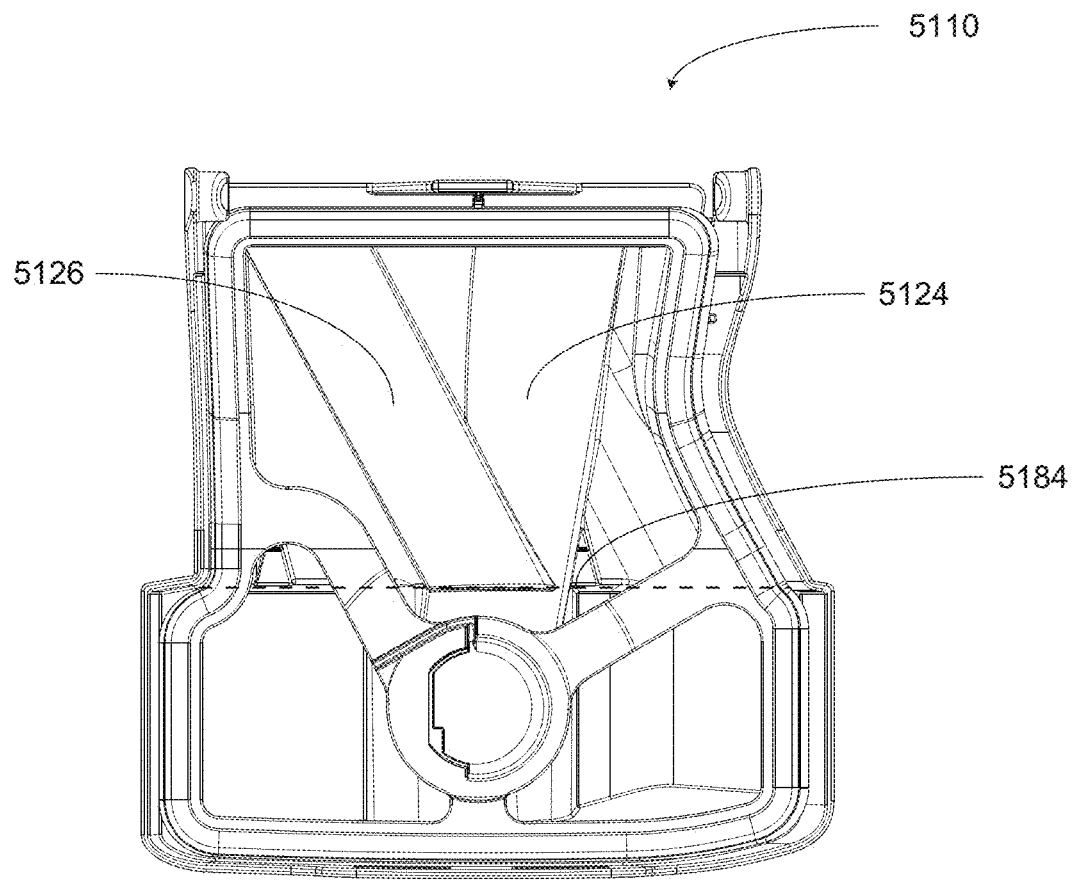

FIG. 49 shows a portion of the humidifier reservoir 5110 according to another example of the present technology. In particular, FIG. 49 shows a water level 5184 at which the air locks would be formed to prevent further ingress of liquid into the reservoir 5110 when the predetermined maximum volume of liquid is in the reservoir 5110.

Figure 50A:
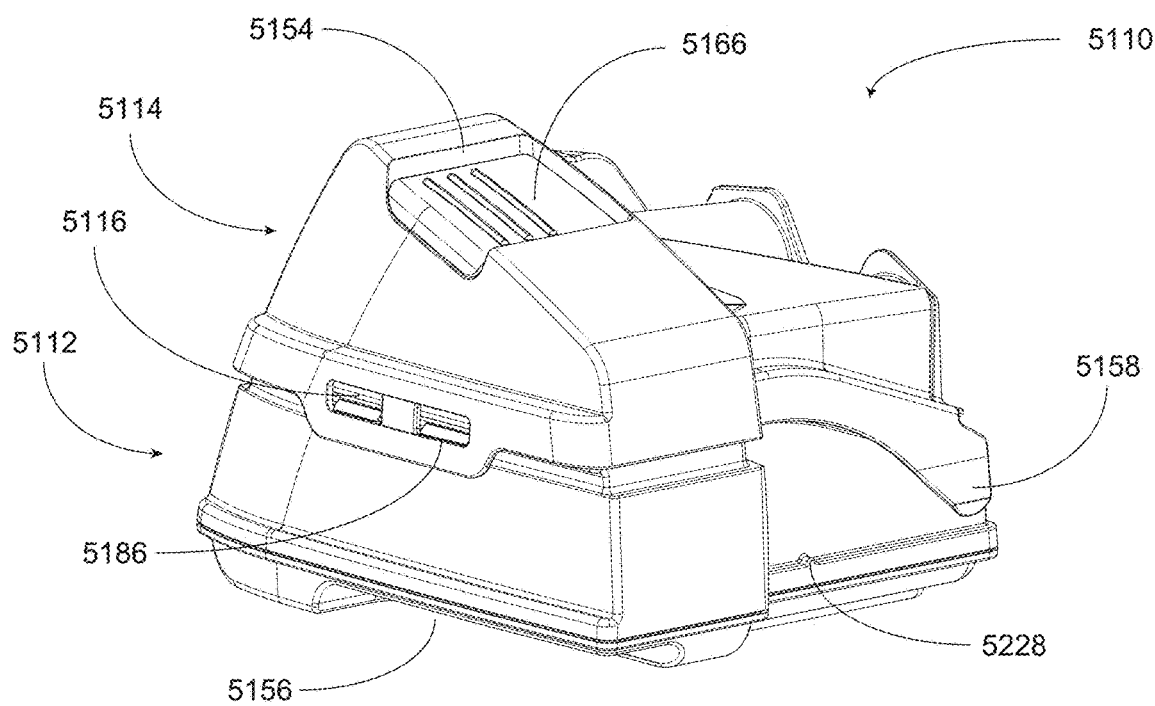
Figure 50B:
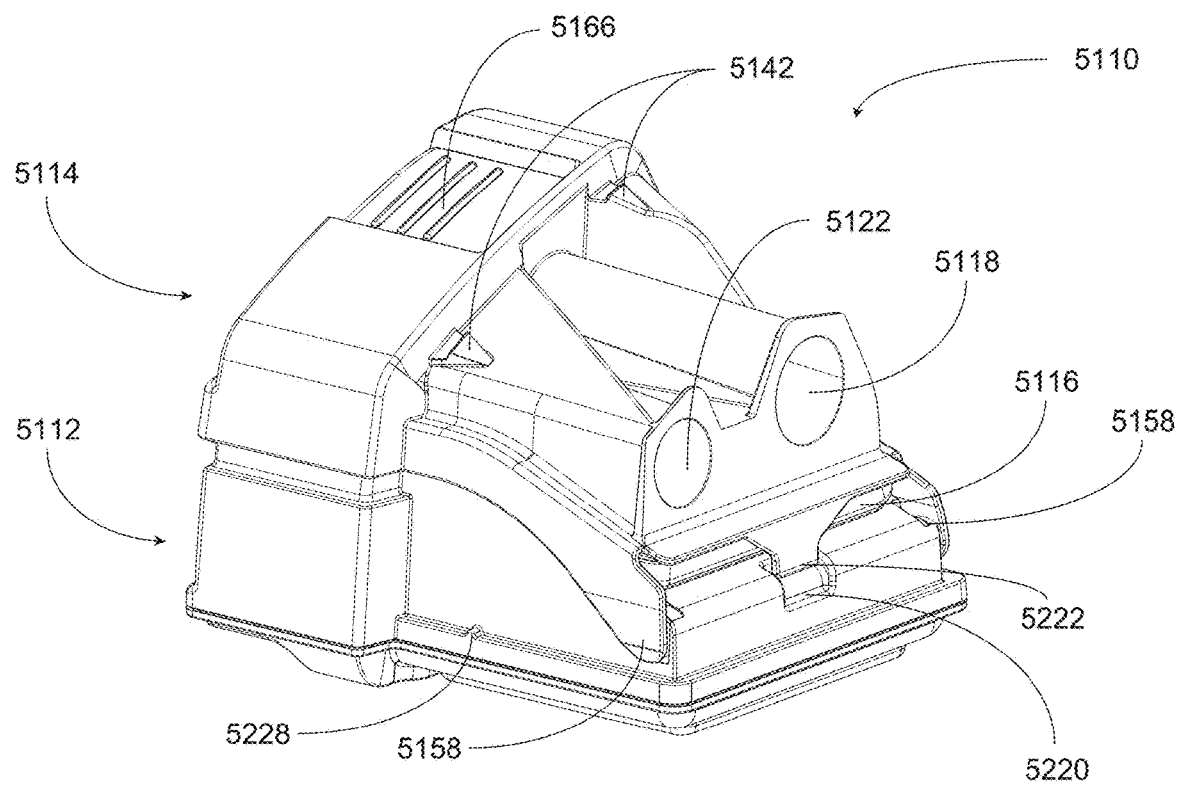
Figure 51A:
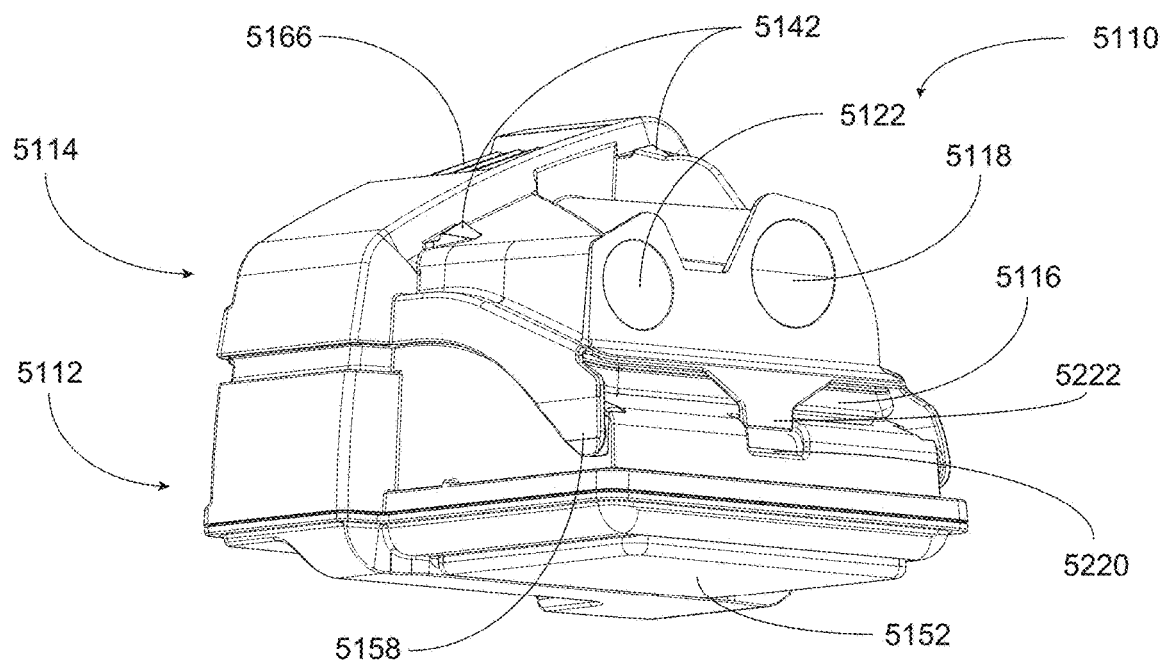
Figure 51B:
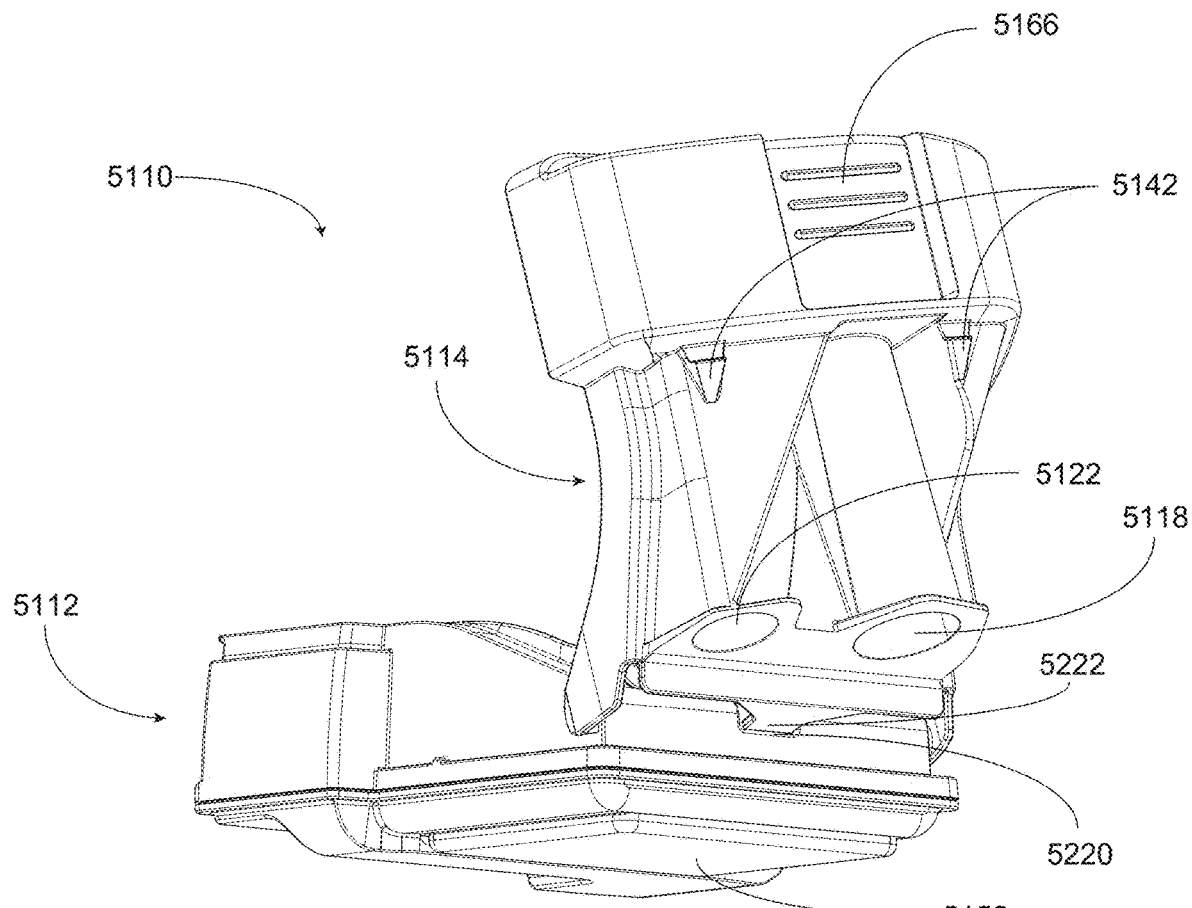

FIGS. 50a, 50b, 51a, and 51b show various views of a humidifier reservoir 5110 in accordance with an example of the present technology, wherein FIGS. 50a, 50b, and 51a show the humidifier reservoir 5110 in a 'closed' configuration, and FIG. 51b shows the humidifier reservoir 5110 in an 'open' configuration.

Figure 52A:
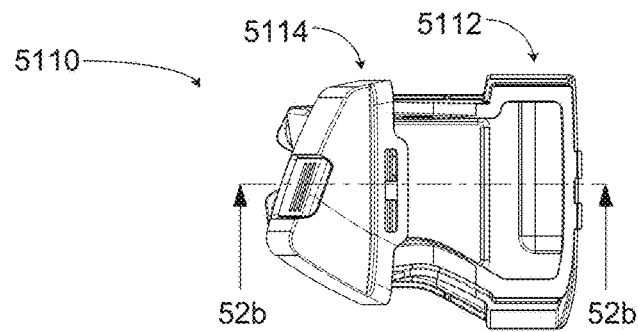
Figure 52B:
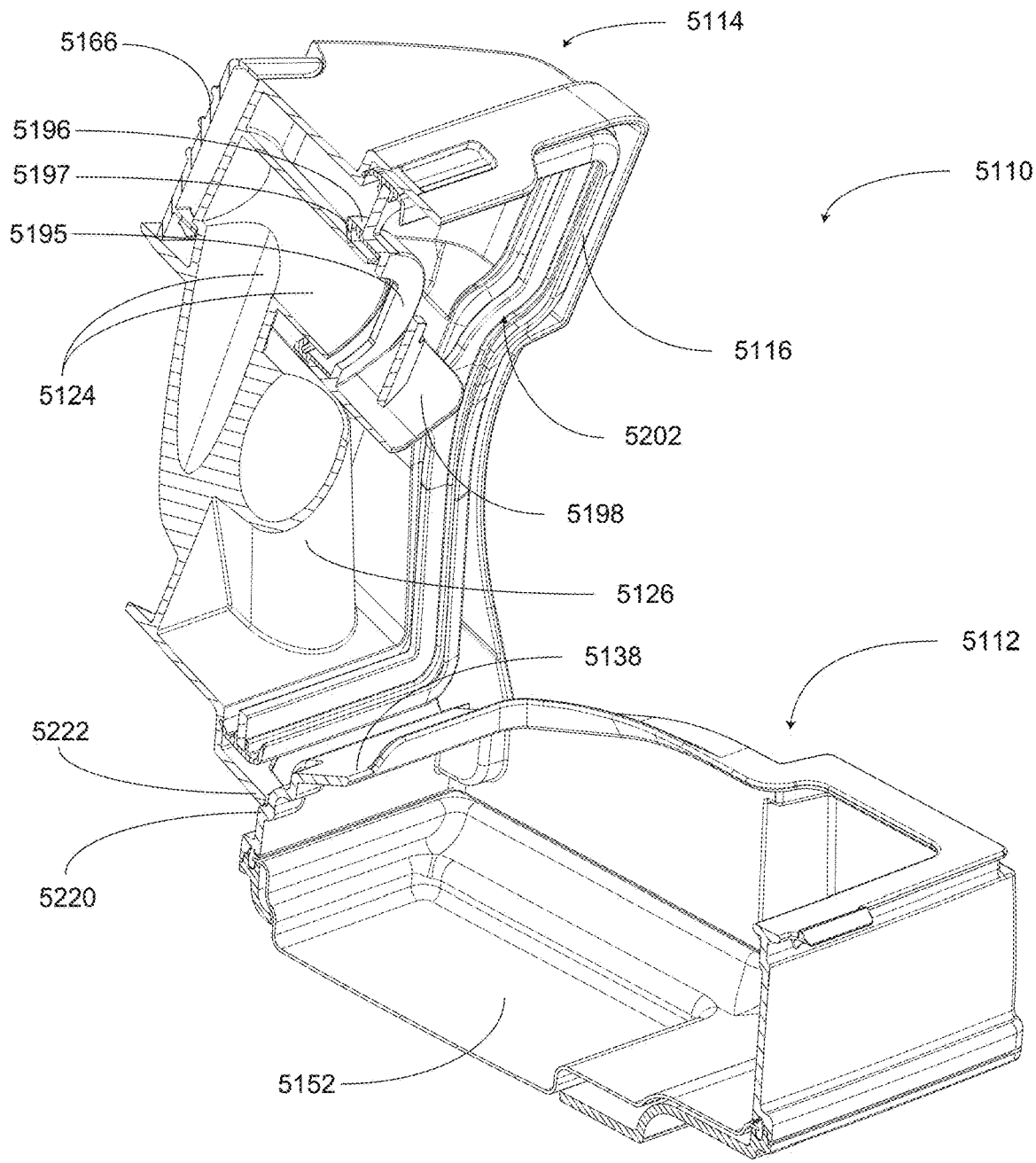

FIGS. 52a and 52b show various views of a humidifier reservoir 5110 in accordance with an example of the present technology. FIG. 52a shows a plan view of the humidifier reservoir 5110 in an 'open configuration', indicating a cross section to be shown in FIG. 52b, and FIG. 52b shows a cross section of the reservoir 5110 through line 52b-52b of FIG. 52a with the cross section visible.

Figure 53:
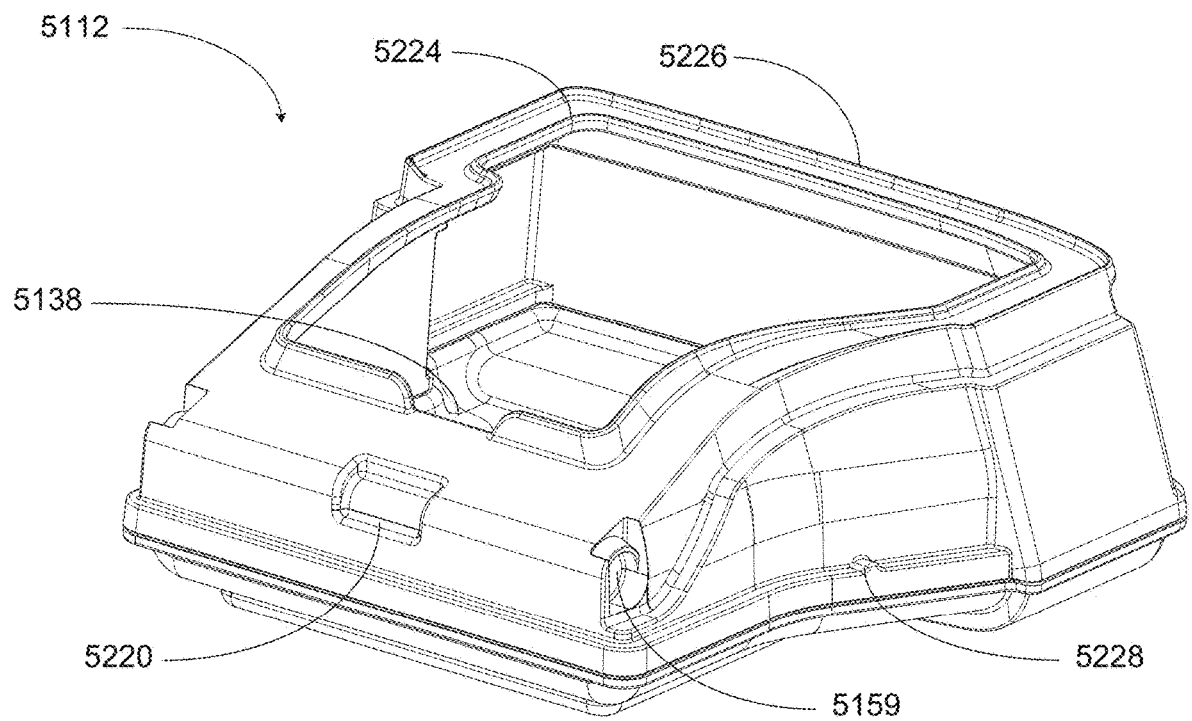
Figure 54:
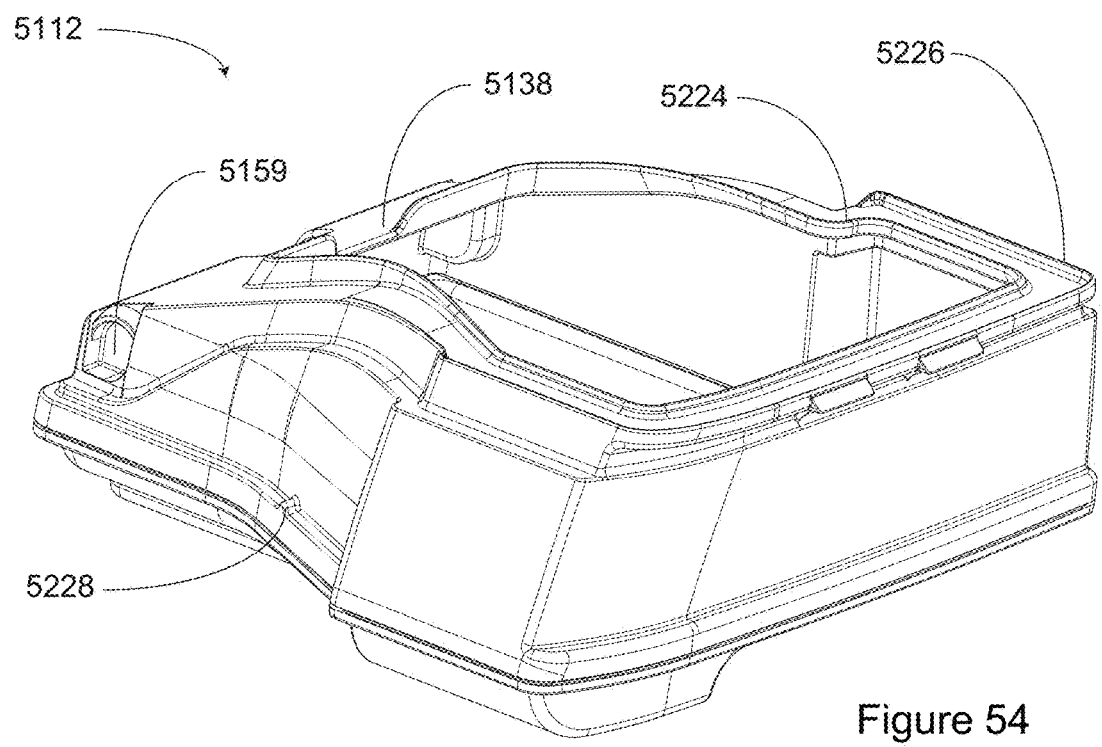

FIGS. 53 and 54 show various views of a reservoir base 5112 in accordance with an example of the present technology.

Figure 55A:
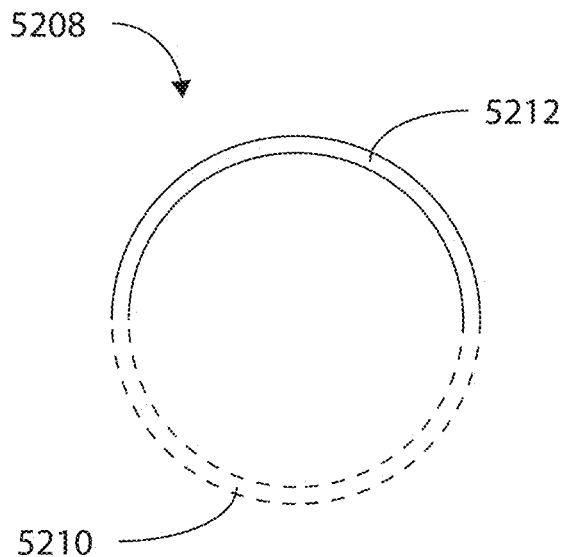
Figure 55B:
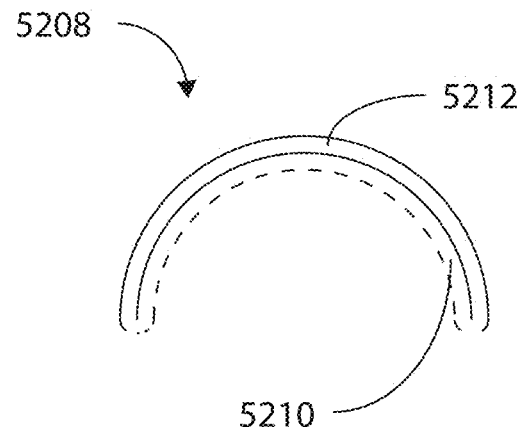

FIGS. 55a and 55b show a collapsible tube 5208 in accordance with an example of the present technology. FIG. 55a shows a collapsible tube 5208 in an 'open' configuration, and FIG. 55b shows a collapsible tube 5208 in a 'closed' configuration.

Figure 56:
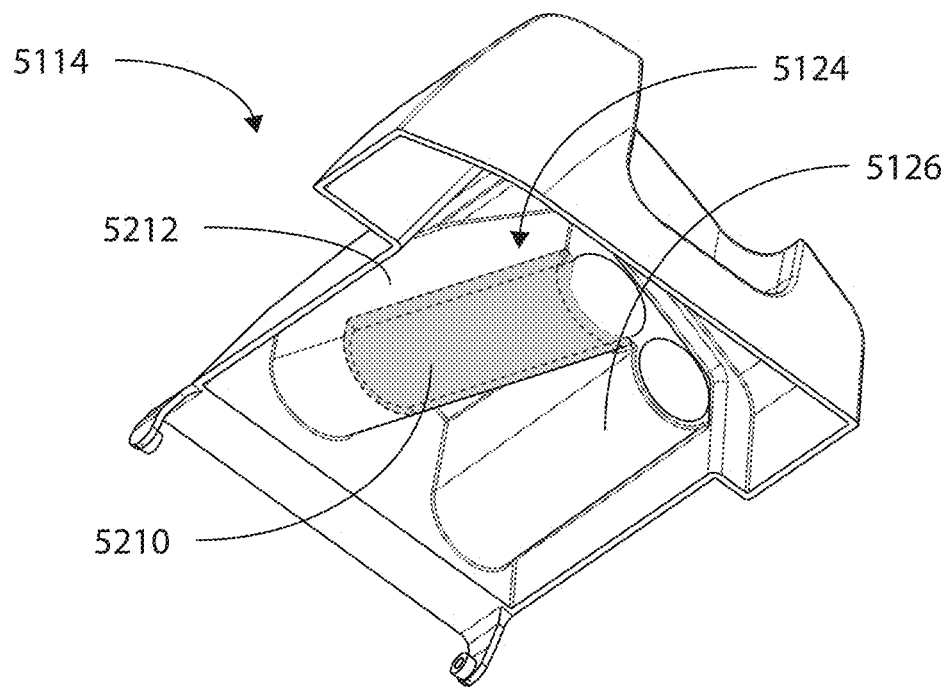

FIG. 56 shows a humidifier reservoir lid 5114 in accordance with an example of the present technology, wherein an inlet tube 5124 of the reservoir lid 5114 comprises a flexible portion 5210 and a rigid portion 5212.

Figure 57A:
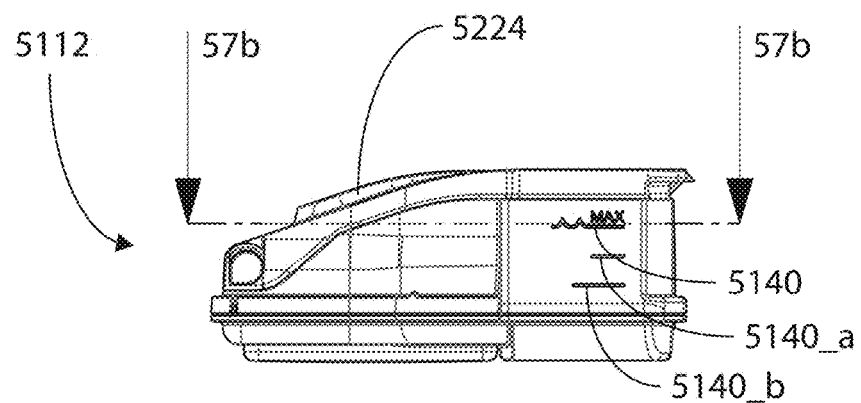
Figure 57B:
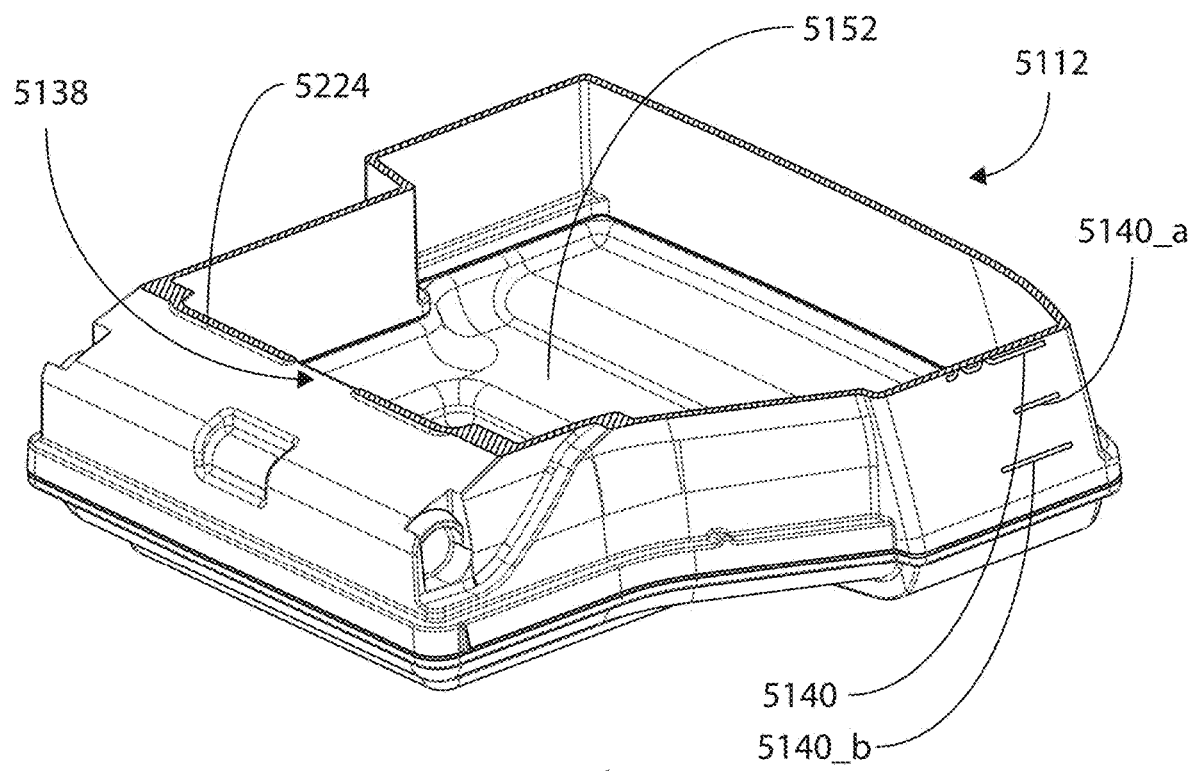

FIG. 57a shows a side view of the humidifier reservoir 5110 (showing the base 5112 only) in accordance with an example of the present technology, indicating a cross section 57b-57b which is shown on FIG. 57b.

FIG. 57b shows a perspective view of the humidifier reservoir 5110 (showing the base 5112 only), showing a cross section as indicated on FIG. 57a. In particular, FIG. 57b shows an orifice 5138 and a water filling indication mark 5140.

Figure 58A:
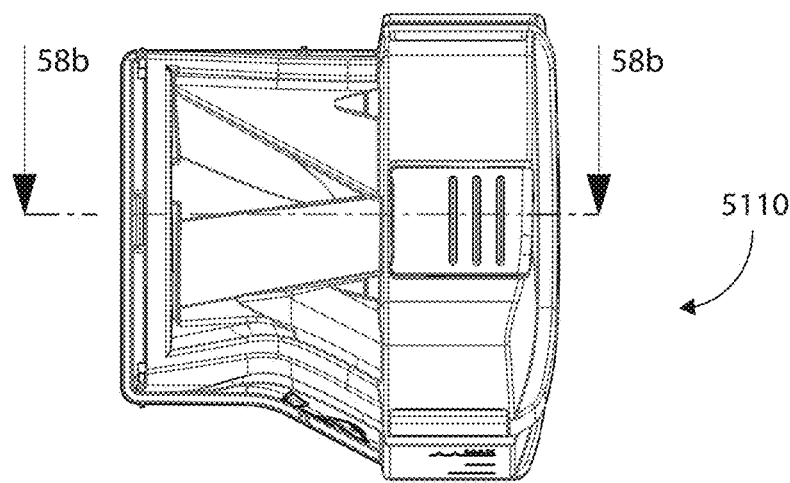
Figure 58B:
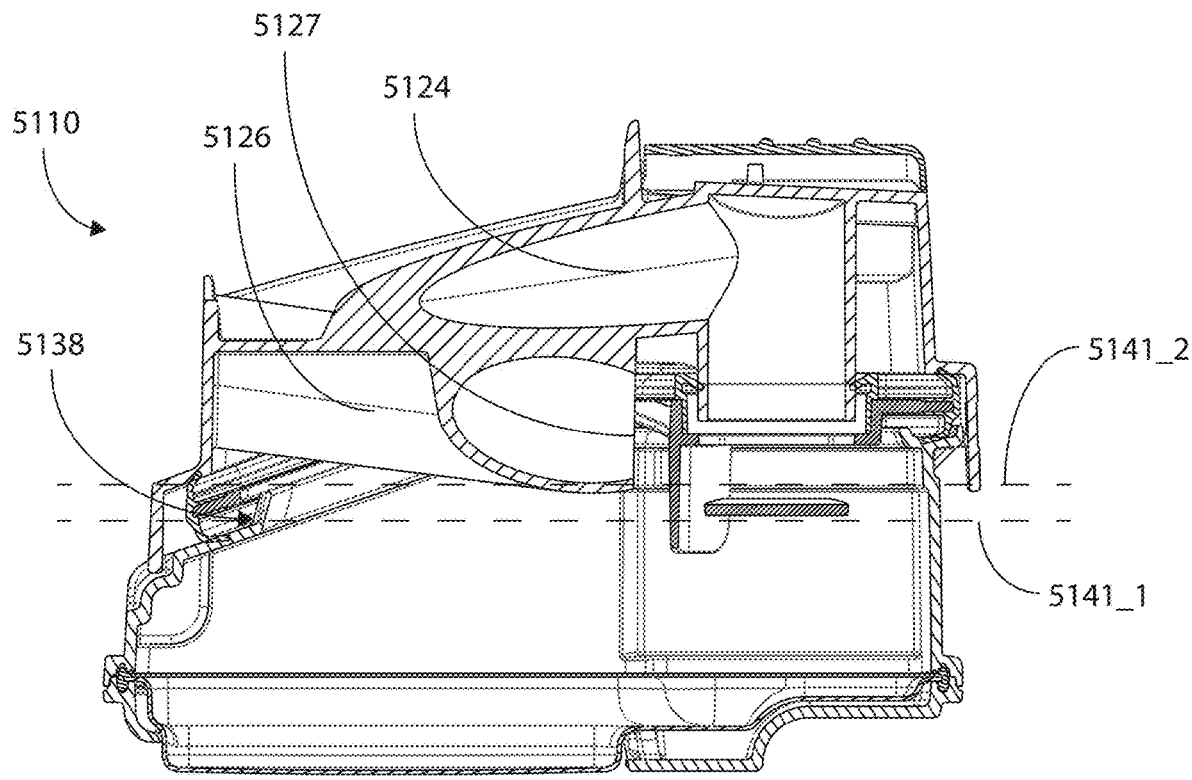

FIG. 58a shows a top view of the humidifier reservoir 5110 in accordance with an example of the present technology, indicating a cross section 58b-58b which is shown on FIG. 58b.

FIG. 58b shows a side view of the humidifier reservoir 5110, showing a cross section as indicated on FIG. 58a. In particular, FIG. 58b shows an orifice 5138, a water level at predetermined maximum volume of water 5141_1 and a water level at threshold volume of water 5141_2.

FIG. 59 shows an exploded perspective view of an RPT device 4000, an integrated humidifier 5000 and a humidifier end cap 5300 according to an example of the present technology.

FIG. 60 shows a perspective view of a humidifier end cap 5300 according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to several examples which may share common characteristics and features. It is to be understood that one or more features of any one example may be combinable with one or more features of the other examples. In addition, any single feature or combination of features in any of the examples may constitute additional examples.

5.1 Treatment Systems

In one form, the present technology comprises an apparatus for treating a respiratory disorder such as an RPT device. The apparatus or device may comprise a pressure generator or blower for supplying a flow of air, to the patient 1000 via an air circuit leading to a patient interface 3000.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

In certain examples of the present technology, a supply of air at positive pressure is provided to the nasal passages of the patient via one or both nares.

5.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 Respiratory Apparatus

An RPT device 4000 in accordance with one aspect of the present technology is shown in FIG. 4a, and comprises mechanical and pneumatic components 4100, electrical components 4200 and is programmed to execute one or more algorithms 4300. The RPT device may comprise an external housing 4010 which may be formed in two parts, an upper portion 4012 and a lower portion 4014. Furthermore, the external housing 4010 may include one or more panel(s) 4015. The RPT device 4000 may comprise a chassis 4016 that supports one or more internal components of the RPT device 4000. In one form a pneumatic block 4020 is supported by, or formed as part of the chassis 4016. The RPT device 4000 may include a handle 4018.

A schematic diagram of a pneumatic circuit of the RPT device 4000 according to an example of the present technology is shown in FIG. 4b. The pneumatic path of the RPT device 4000 may comprise an inlet air filter 4112, an inlet muffler 4122, a pressure generator 4140 capable of supplying air at positive pressure (preferably a blower 4142), a pneumatic block 4020 and an outlet muffler 4124. One or more transducers 4270, such as pressure sensors 4272 and flow sensors 4274 may be included in the pneumatic path.

The pneumatic block 4020 may comprise a portion of the pneumatic path that is located within the external housing 4010 and may house the pressure generator 4140.

The RPT device 4000 may include an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

FIG. 7 shows a prior art embodiment of a RPT device 4000, which is connectable to a humidifier 5000. The RPT device may also be integrated with a humidifier 5000 so that an external housing 4010 encases the components that perform the equivalent function of a RPT device 4000 as well as components that perform the equivalent function of a humidifier 5000.

FIG. 8 shows an embodiment of such an integrated device comprising a RPT device 4000 and a humidifier 5000 according to an example of the present technology. It should be understood that subsequent references to a humidifier 5000 refers to the integrated device, in particular the components that perform the equivalent function of a humidifier 5000.

5.4.1 RPT Device Mechanical & Pneumatic Components 4100

5.4.1.1 Air Filter(s) 4110

A RPT device in accordance with one form of the present technology may include one or more air filters 4110.

In one form, an inlet air filter 4112 is located at the beginning of the pneumatic path upstream of a blower 4142. See FIG. 4*b*.

In one form, an outlet air filter 4114, for example an antibacterial filter, is located between an outlet of the pneumatic block 4020 and a patient interface 3000. See FIG. 4*b*.

5.4.1.2 Muffler(s) 4120

In one form of the present technology, an inlet muffler 4122 is located in the pneumatic path upstream of a blower 4142. See FIG. 4*b*.

In one form of the present technology, an outlet muffler 4124 is located in the pneumatic path between the blower 4142 and a patient interface 3000. See FIG. 4*b*.

5.4.1.3 Pressure Generator 4140

In a preferred form of the present technology, a pressure generator 4140 for producing a flow of air at positive pressure is a blower 4142. For example the blower may include a brushless DC motor 4144 with one or more impellers housed in a volute. The blower may preferably be capable of delivering a supply of air, for example up to about 120 litres/minute, at a positive pressure in a range from about 4 cm $H_2O$ to about 20 cm $H_2O$, or in other forms up to about 30 cm $H_2O$. Examples of a suitable blower may include a blower as described in any one of the following patents or patent applications the contents of which are incorporated herein in their entirety: U.S. Pat. Nos. 7,866,944; 8,638,014; 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s) 4270

Transducers may be internal of the RPT device, or external of the RPT device. External transducers may be located for example on or form part of the air circuit, e.g. the patient interface. External transducers may be in the form of non-contact sensors such as a Doppler radar movement sensor that transmit or transfer data to the RPT device.

In one form of the present technology, one or more transducers 4270 are located in the pneumatic path, such as upstream and/or downstream of the pressure generator 4140. The one or more transducers 4270 are constructed and arranged to measure properties such as flow rate, a pressure, a temperature or a humidity of the flow of air at that point in the pneumatic path.

In one form of the present technology, one or more transducers 4270 are located proximate to the patient interface 3000, such as in the air circuit 4170.

In another form of the present technology, one or more transducer 4270 may be arranged to measure properties of the ambient air.

In one form, a signal from a transducer 4270 may be filtered, such as by low-pass, high-pass or band-pass filtering.

5.4.1.4.1 Flow Transducer 4274

A flow rate transducer 4274 in accordance with the present technology may be based on a differential pressure transducer, for example, an SDP600 Series differential pressure transducer from SENSIRION.

In one form, a signal representing a flow rate such as a total flow Qt from the flow transducer 4274 is received by the central controller 4230.

5.4.1.4.2 Pressure Transducer 4272

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

5.4.1.4.3 Motor Speed Transducer 4276

In one form of the present technology a motor speed transducer 4276 is used to determine a rotational velocity of the motor 4144 and/or the blower 4142. A motor speed signal from the motor speed transducer 4276 is preferably provided to the therapy device controller 4240. The motor speed transducer 4276 may, for example, be a speed sensor, such as a Hall effect sensor.

5.4.1.5 Anti-Spillback Valve 4160

In one form of the present technology, an anti-spillback valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit 4170

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

5.4.1.7 Supplemental Oxygen 4180

In one form of the present technology, supplemental oxygen 4180 is delivered to one or more points in the pneumatic path, such as upstream of the pneumatic block 4020, to the air circuit 4170 and/or to the patient interface 3000.

5.4.1.7.1 Power Supply 4210

A power supply (or PSU) 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.1.7.2 Input Devices 4220

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.1.7.3 Central Controller 4230

In one form of the present technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein such as the one or more algorithms 4300. In some forms of the present technology, the central controller 4230 may be integrated with a RPT device 4000. However, in some forms of the present technology, the central controller 4230 may be implemented discretely from the flow generation components of the RPT device 4000, such as for purpose of performing any of the methodologies described herein without directly controlling delivery of a respiratory treatment. For example, the central controller 4230 may perform any of the methodologies described herein for purposes of determining control settings for a ventilator or other respiratory related events by analysis of stored data such as from any of the transducers 4270 described herein.

5.4.1.7.4 Clock 4232

Preferably RPT device 4000 includes a clock 4232 that is connected to the central controller 4230.

5.4.1.7.5 Therapy Device Controller 4240

In one form of the present technology, therapy device controller 4240 is a control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.1.7.6 Protection Circuits 4250

The one or more protection circuits 4250 in accordance with the present technology may comprise an electrical protection circuit, a temperature and/or pressure safety circuit.

5.4.1.7.7 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.1.8 Data Communication Systems 4280

In one preferred form of the present technology, a data communication interface 4280 is provided, and is connected to the central controller 4230. Data communication interface 4280 is preferably connectable to remote external communication network 4282 and/or a local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.4.1.9 Output Devices 4290 (Including Optional Display, Alarms)

An output device 4290 in accordance with the present technology may take the form of one or more of a visual, audio and haptic unit. A visual display may be a Liquid Crystal Display (LCD) or Light Emitting Diode (LED) display.

5.4.1.9.1 Display Driver 4292

A display driver 4292 receives as an input the characters, symbols, or images intended for display on the display 4294, and converts them to commands that cause the display 4294 to display those characters, symbols, or images.

5.4.1.9.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.2 RPT Device Algorithms 4300

5.4.2.1 Pre-Processing Module 4310

A pre-processing module 4310 in accordance with one form of the present technology receives as an input a signal from a transducer 4270, for example a flow transducer 4274 or pressure transducer 4272, and preferably performs one or more process steps to calculate one or more output values that will be used as an input to another module, for example a therapy engine module 4320.

In one form of the present technology, the output values include the patient interface or mask pressure Pm, the respiratory flow Qr, and the unintentional leak flow Ql.

In various forms of the present technology, the pre-processing module 4310 comprises one or more of the following algorithms: pressure compensation algorithm 4312, vent flow algorithm 4314 (e.g. intentional leak), leak flow algorithm 4316 (e.g. unintentional leak) and respiratory flow algorithm 4318.

5.4.2.1.1 Pressure Compensation 4312

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.2.1.2 Vent Flow 4314

In one form of the present technology, a vent flow calculation algorithm 4314 receives as an input an estimated pressure, Pm, in the patient interface 3000 and estimates a vent flow of air, Qv, from a vent 3400 in a patient interface 3000.

5.4.2.1.3 Leak Flow 4316

In one form of the present technology, a leak flow algorithm 4316 receives as an input a total flow, Qt, and a vent flow Qv, and provides as an output an estimate of the unintentional leak, i.e. leak flow, Ql, by calculating an average of Qt-Qv over a period sufficiently long to include several breathing cycles, e.g. about 10 seconds.

In one form, the leak flow algorithm 4316 receives as an input a total flow Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt Qv, and low pass filtered square root of pressure Pm, where the low pass filter time constant has a value sufficiently long to include several breathing cycles, e.g. about 10 seconds.

5.4.2.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

5.4.2.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output, one or more therapy parameters.

In one form of the present technology, a therapy parameter is a CPAP treatment pressure Pt.

In one form of the present technology, a therapy parameter is one or more of a level of pressure support and a target ventilation.

In various forms of the present technology, the therapy engine module 4320 comprises one or more of the following algorithms: phase determination algorithm 4321, waveform determination algorithm 4322, ventilation determination algorithm 4323, flow limitation determination algorithm 4324, Apnea/hypopnea determination algorithm 4325, Snore determination algorithm 4326, Patency determination algorithm 4327 and Therapy parameter determination algorithm 4328.

5.4.2.2.1 Phase Determination 4321

In one form of the present technology, the RPT device 4000 does not determine phase.

In another form of the present technology, the RPT device 400 does determine phase using a phase determination algorithm 4321. The phase determination algorithm 4321 receives as an input a signal indicative of respiratory flow, Qr, and provides as an output a phase of a breathing cycle of a patient 1000.

In some forms the phase output may include a discrete variable with values of one or more of inhalation, mid-inspiratory pause, and exhalation. For example the phase output may be determined to have a discrete value of inhalation when a respiratory flow Qr has a positive value that exceeds a positive threshold and the phase may be determined to have a discrete value of exhalation when a respiratory flow Qr has a negative value that is more negative than a negative threshold.

In other forms, the phase output may include a continuous variable, for example varying from 0 to 1, or 0 to 2Pi.

5.4.2.2.2 Waveform Determination 4322

In one form of the present technology, a control module 4330 controls a pressure generator 4140 to provide an approximately constant positive airway pressure throughout a respiratory cycle of a patient.

In other forms of the present technology, a control module 4330 controls a pressure generator 4140 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In some forms of the present technology a waveform determination algorithm 4322 receives as an input a value indicative of current patient ventilation, Vent, and provides as an output a waveform of pressure vs. phase. For example a ventilation determination algorithm 4323 may receive as an input a respiratory flow Qr, and determine a measure indicative of patient ventilation, Vent. The current value of patient ventilation, Vent, may be determined as half the low-pass filtered absolute value of respiratory flow, Qr.

5.4.2.2.3 Ventilation Determination 4323

In one form of the present technology, a ventilation determination algorithm 4323 receives an input a respiratory flow Qr, and determines a measure indicative of patient ventilation, Vent.

In some forms of the present technology, ventilation determination algorithm 4323 determines a current value of patient ventilation, Vent, as half the low-pass filtered absolute value of respiratory flow, Qr.

5.4.2.2.4 Determination of Inspiratory Flow Limitation 4324

In one form of the present technology, the central controller executes one or more algorithms 4324 for the detection of inspiratory flow limitation.

In one form the algorithm 4324 receives as an input a respiratory flow signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6a. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g. three events. The moving average of continuously updated values of the (e.g. sixty five) points are hereinafter called the "scaled flow", designated as Qs(t). Alternatively, a single inspiratory event can be utilised rather than a moving average.

From the scaled flow, two shape factors relating to the determination of partial obstruction may be calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other values than those described.

5.4.2.2.5 Determination of Apneas and Hypopneas 4325

In one form of the present technology, the central controller 4230 executes one or more algorithms 4325 for the determination of the presence of apneas and/or hypopneas.

Preferably the one or more algorithms 4325 receive as an input a respiratory flow signal Qr and provide as an output a flag that indicates that an apnea or a hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

5.4.2.2.6 Determination of Snore 4326

In one form of the present technology, the central controller 4230 executes one or more snore algorithms 4326 for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

5.4.2.2.7 Determination of Airway Patency 4327

In one form of the present technology, the central controller 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 cmH20.

In one form, airway patency algorithm 4327 receives as an input a respiratory flow signal Qr, and determines the presence or absence of a cardiogenic signal. The absence of a cardiogenic signal is taken to be an indication of a closed airway.

5.4.2.2.8 Determination of Therapy Parameter Determination 4328

In one form of the present technology, the central controller 4230 executes one or more therapy parameter determination algorithms 4328 for the determination of a target treatment pressure Pt to be delivered by the RPT device 4000.

Preferably the therapy parameter determination algorithm 4328 receives as an input one of more of the following:
  A measure of respiratory phase;
  A waveform;
  A measure of ventilation;
  A measure of inspiratory flow limitation;
  A measure of the presence of apnea and/or hypopnea;

A measure of the presence of snore; and

A measure of the patency of the airway.

The therapy parameter determination algorithm 4328 determines the treatment pressure Pt as a function of indices or measures of one or more of flow limitation, apnea, hypopnea, patency, and snore. In one implementation, these measures are determined on a single breath basis, rather than on an aggregation of several previous breaths.

FIG. 4e is a flow chart illustrating a method 4500 carried out by the central controller 4230 as one implementation of the algorithm 4328. The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the treatment pressure Pt by a predetermined pressure increment ΔP, provided the increased treatment pressure Pt would not exceed an upper limit Pmax. In one implementation, the predetermined pressure increment ΔP and upper limit Pmax are 1 cmH20 and 20 cmH20 respectively. The method 4500 then returns to step 4520.

At step 4560, the central controller 4230 decreases the treatment pressure Pt by a decrement, provided the decreased treatment pressure Pt would not fall below a lower limit Pmin. The method 4500 then returns to step 4520. In one implementation, the decrement is proportional to the value of Pt-Pmin, so that the decrease in Pt to the lower limit Pmin in the absence of any detected events is exponential. Alternatively, the decrement in Pt could be predetermined, so the decrease in Pt to the lower limit Pmin in the absence of any detected events is linear.

5.4.2.3 Control Module 4330

A control module 4330 in accordance with one aspect of the present technology receives as an input a target treatment pressure Pt, and controls a pressure generator 4140 to deliver that pressure.

A control module 4330 in accordance with one aspect of the present technology receives as an input an EPAP pressure and an IPAP pressure, and controls a pressure generator 4140 to deliver those respective pressures.

5.4.2.4 Detection of Fault Conditions 4340

In one form of the present technology, the central controller 4230 executes one or more methods for the detection of fault conditions. Preferably the fault conditions detected by the one or more methods includes at least one of the following:

Power failure (no power, or insufficient power)

Transducer fault detection

Failure to detect the presence of a component

Operating parameters outside recommended ranges (e.g. pressure, flow, temperature, PaO2)

Failure of a test alarm to generate a detectable alarm signal.

Upon detection of the fault condition, the corresponding algorithm signals the presence of the fault by one or more of the following:

Initiation of an audible, visual &/or kinetic (e.g. vibrating) alarm

Sending a message to an external device

Logging of the incident

5.5 Humidifier 5000

5.5.1 Humidifier Overview

In one form of the present technology there is provided a humidifier 5000 to change the absolute humidity of air for delivery to a patient relative to ambient air. Typically, the humidifier 5000 is used to increase the absolute humidity and increase the temperature of the flow of air relative to ambient air before delivery to the patient's airways.

There are a number of performance requirements and/or design requirements that may be relevant to a humidifier. Some known performance requirements and/or design requirements in relation to humidifier design may include: reduction of a volume and/or a footprint of the humidifier (e.g. for bedside placement), ability to provide humidification for an entire therapy session, efficient use of the water supply, requirement to couple to the respiratory apparatus, minimisation of pressure drop for the flow of air through the humidifier, and/or requirement to maintain a positive pressure at the entrance of the patient's airways (e.g. therefore a requirement to maintain a positive pressure in the humidifier). It is one of the aims of the present technology to address, or improve, at least some of the above performance requirements and/or design requirements.

A simplified representation of a humidifier 5000 is shown in FIG. 5a. In one form, a humidifier 5000 may comprise a humidifier reservoir 5110, a heating element 5240 and one or more sensors 5270. The humidifier 5000 may be configured to receive a flow of air from a pressure generator 4140 via an air circuit 4170, and deliver a flow of humidified air to a patient interface 3000 (not shown in FIG. 5a), for example via a heated air circuit 4171.

A simplified schematic of a humidifier 5000 according to an example of the present technology is shown in FIG. 5b. The humidifier 5000 may comprise one or more controllers 5250 such as a heated air circuit controller 5254, a heating element controller 5252 or a central humidifier controller 5251, which may be discrete controllers or one controller performing multiple functions. The controller(s) 5250 may be in electrical communication with one or more of: one or more sensors 5270, input devices 4220, output devices 4290, heated air circuit 4171 and a heating element 5240 as shown in FIG. 5b.

5.5.2 Humidifier Mechanical Components 5.5.2.1 Water Reservoir Dock 5130

Figure 13:
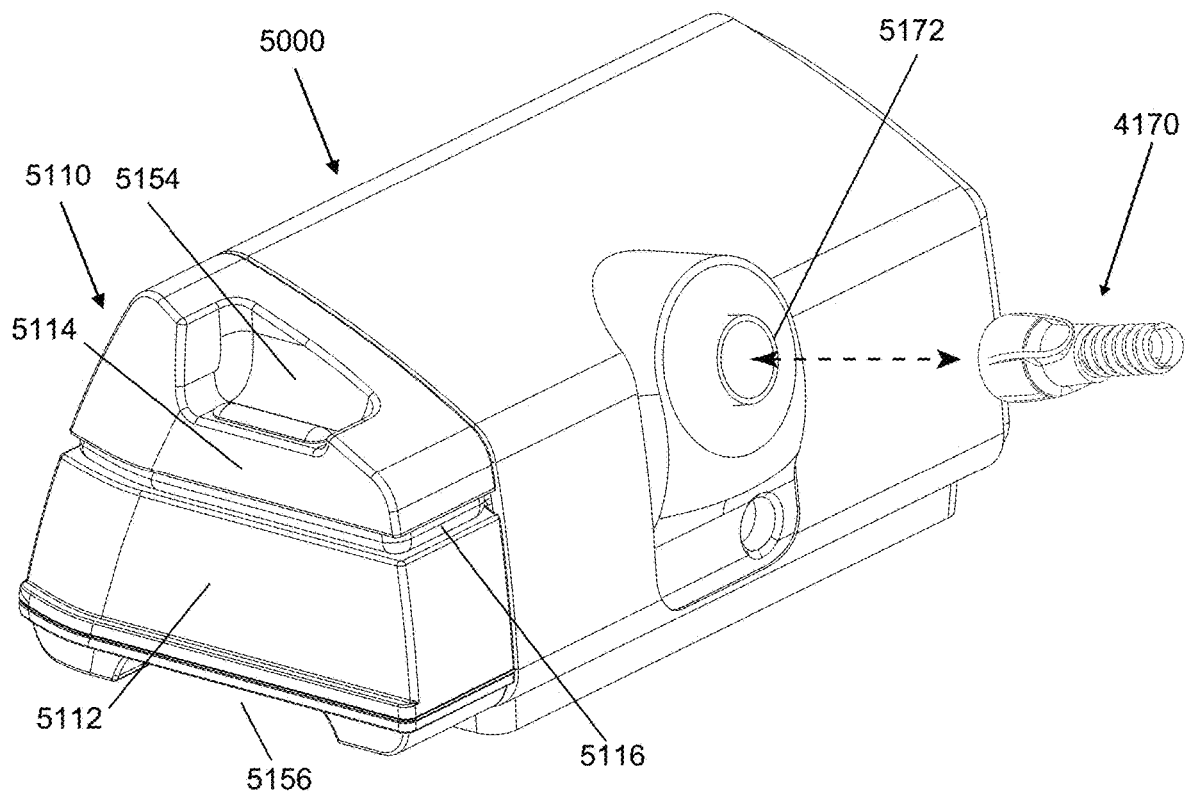
Figure 14:
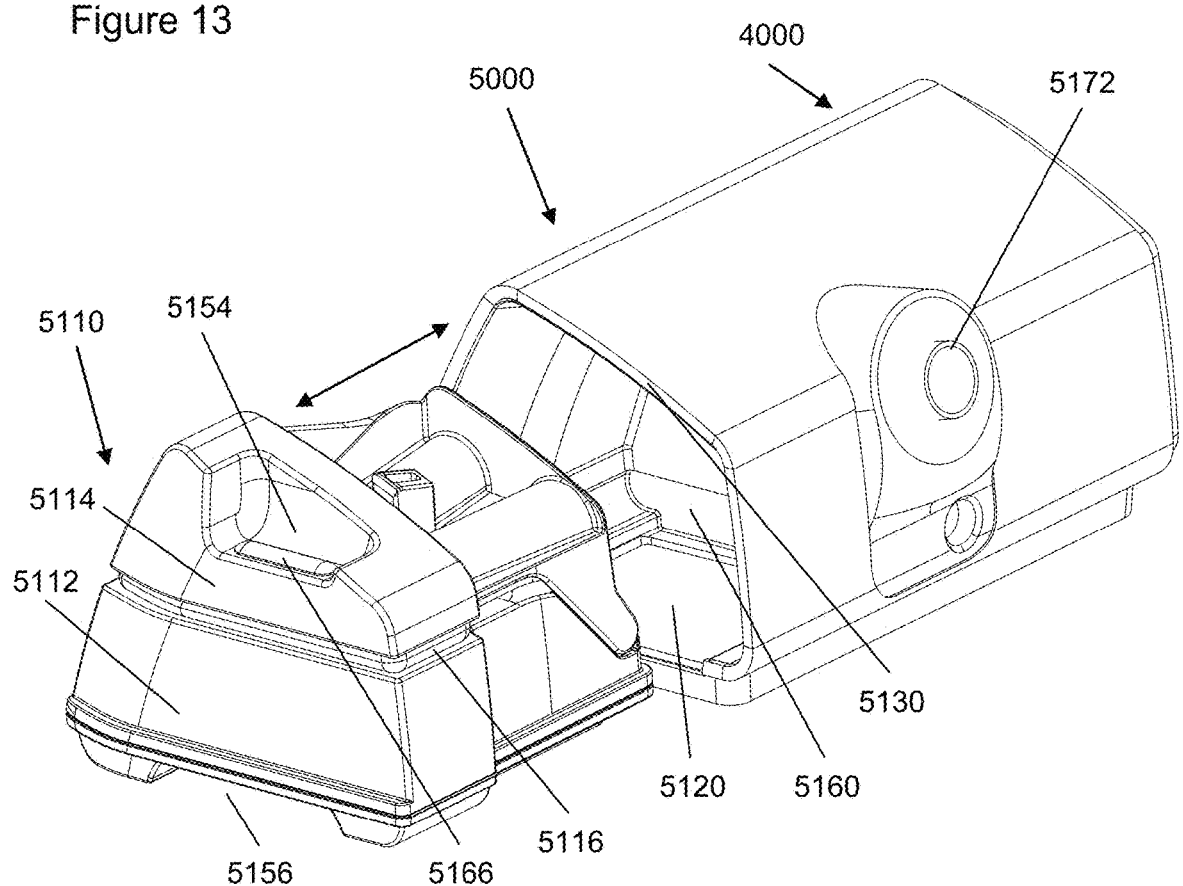

As shown in FIGS. 13 to 16, a humidifier 5000 may comprise a water reservoir dock 5130 to receive a water reservoir 5110. As shown in FIG. 14, the water reservoir dock 5130 may comprise a cavity 5160 formed therein to receive the water reservoir 5110. In one form, the water reservoir dock 5130 may be integrated with the humidifier 5000 as shown in FIGS. 13 to 16. The water reservoir dock 5130 may also connect the water reservoir 5110 to the pneumatic path. In this arrangement, the reservoir dock 5130 comprises a dock air outlet 5168 to deliver a flow of air to a water reservoir 5110, a dock air inlet 5170 to receive the flow of air that has been humidified in the water reservoir 5110, and a humidifier outlet 5172 to transfer the flow of humidified air to the air circuit 4170. The cavity 5160 may include a top portion configured to cover at least a portion of the lid of the reservoir 5110 and a bottom portion including the heater plate 5120.

It should be understood that the reservoir dock 5130 may be provided separately to a humidifier 5000 in an alternate arrangement. In such an arrangement, additional interfaces may be used to connect the reservoir dock 5130 to the humidifier 5000.

In another arrangement, a water reservoir dock 5130 may comprise an opening in a substantially horizontal plane, so that the water reservoir 5110 may be inserted from above or below the water reservoir dock 5130.

5.5.2.2 Water Reservoir 5110

FIGS. 9 to 12 show one form of a water reservoir 5110, which comprises a reservoir base 5112, a reservoir lid 5114, and an intermediate portion 5202 including a compliant portion 5116. The reservoir 5110 is configured to hold a given, maximum volume of liquid (e.g. water), typically several hundred millilitres, e.g. 300 millilitres (ml), 325 ml, 350 ml or 400 ml, although it is to be understood that other volumes of liquid may be utilised such as 100 ml, 200 ml, 250 ml, 500 ml or more or less. In one form, the reservoir 5110 may comprise a cavity formed by a plurality of walls to hold the given, maximum volume of liquid as shown in FIGS. 11 and 12.

According to one aspect, the water reservoir 5110 is configured to add humidity to a flow of air from the RPT device 4000. The water reservoir 5110 may be configured to do so by encouraging the flow of air to travel in a tortuous path through the reservoir 5110. The reservoir 5110 is also configured to discourage egress of liquid therefrom, such as when the reservoir 5110 is displaced and/or rotated from its normal, working orientation, liquid will not leak through any apertures and/or in between its sub-components. As the flow of air to be humidified by the humidifier 5000 is typically pressurised, the reservoir 5110 may also be configured to prevent losses in pneumatic pressure through leak and/or flow impedance.

The water reservoir 5110 may comprise an inlet 5118 for receiving the flow of air into the reservoir 5110, and an outlet 5122 for delivering a flow of air from the reservoir 5110. In one form, the reservoir 5110 may include to an inlet tube 5124 and/or an outlet tube 5126 (e.g., see FIGS. 10 and 12). In one configuration the inlet 5118 and inlet tube 5124 are integrally formed as one inlet component and the outlet 5122 and the outlet tube 5126 are integrally formed as one outlet component (see FIGS. 10-12, 22-29 and 47a-52b). In other configurations the inlet tube 5124 and/or the outlet tube 5126 may be separate tubes that are coupled to the inlet 5118 and/or the outlet 5122 respectively (see FIGS. 41a to 46). The water reservoir 5110 is configured to increase the humidity of the flow of air as it flows through the reservoir 5110.

5.5.2.2.1 Water Reservoir Lid 5114

In one form, the water reservoir lid 5114 is pivotably connected to the base 5112 by hinges 5158 to allow the reservoir 5110 to be converted between an open configuration, as shown in FIG. 11, and a closed configuration, as shown in FIG. 9 and FIG. 10. Reservoir base 5112 may include a pair of upright supports 5161 that support a rear edge of the hinge 5158, as seen, e.g., in FIGS. 10 and 11. When the water reservoir 5110 is in its closed configuration, the compliant portion 5116 is put into sealing engagement between the base 5112 and the lid 5114 to seal the base 5112 and the lid 5114 and prevent egress of water from the reservoir 5110. The hinges 5158 may couple to complementary hinge recess portions 5159 (see FIG. 12) located in the reservoir base 5112. In one form, the lid 5114 may be constructed from a bio-compatible material, such as a plastic or thermoplastic polymer, for example, acrylonitrile butadiene styrene (ABS) or polycarbonate material.

Another aspect of the present technology relates to the operation of the pivoting action in the lid 5114 in relation to the base 5112. As the lid 5114 rotates about the hinges 5158, a range of rotation may be defined as shown in FIG. 51a and FIG. 51b. In one form, two ends of the range of rotation may be defined by closure of the lid 5114 with respect to the base 5112, where one of the two ends may be a fully open position defined by a rotation guide 5220, which may interfere with a rotation stop 5222 at the fully open position.

According to another aspect, the lid 5114 may configured so that when a user attempts to open the lid 5114 further than the rotation stop 5222 and the rotation guide 5220, the lid 5114 would disconnect from the base 5112. As shown in FIG. 51b and FIG. 52b, at the fully open position the rotation guide 5220 may be in contact with the rotation stop 5222. In this form, attempts to further open the lid 5114 with respect to the base 5112 would cause the rotation stop 5222 to act as a pivot of a cantilever, and cause the lid 5114 to separate from the base 5112 at the hinges 5158, whereby damage to the reservoir 5110, for example from application of excessive force thereto, may be avoided. In one form, the hinges 5158 may be configured to allow disconnection more easily at one orientation of the lid 5114 with respect to the base 5112 (e.g. then the reservoir 5110 is in the fully open position) than at another orientation. This may be achieved by, for example, introduction of a taper to the hinges 5158 on the lid 5114 as shown in FIGS. 47a and 47b.

5.5.2.2.2 Compliant Portion 5116

In one form, when the water reservoir 5110 is in use, the compliant portion 5116 may act as a seal between the reservoir base 5112 and the reservoir lid 5114. The compliant portion 5116 may also perform other functions, such as to improve thermal contact between the reservoir 5110 and the heater plate 5120, as will be described in further detail below.

The compliant portion 5116 may be provided as part of the reservoir lid 5114 or as part of the reservoir base 5112, or independently of both, for example as part of an intermediate portion 5202. The compliant portion 5116 may be engaged with the reservoir lid 5114 or the reservoir base 5112 by any number of means including, and not limited to, ultrasonic welding, friction fitting, gluing or by using an intermediate component. The intermediate portion 5202 may include the compliant portion 5116 and a carrier 5117 (as shown in FIG. 12).

The compliant portion 5116 preferably includes a sufficiently resilient construction so as to be able to resist forces and/or pressures generated in the reservoir 5110, such as those generated by the user, the reservoir dock 5130 and/or the flow of air flowing through the reservoir 5110. The compliant portion 5116 is also preferably compliant to be able couple to the lid 5114 and/or the base 5112, and conform to its shape. In one form, the carrier 5117 of the intermediate portion may be constructed from a nylon material of approximately 2 mm thickness (such as 1 mm, 1.5 mm, 2.5 mm or 3 mm), and a silicone material may be used to overmould onto the carrier 5117 to form the compliant portion of the intermediate portion 5202.

In some arrangements, the compliant portion 5116 may couple to the lid 5114 and/or the base 5112, and the base 5112 and/or the lid 5114 may be formed as two separate parts that are able to be assembled with the compliant portion 5116 coupled therebetween.

In an alternative arrangement, the compliant portion 5116 may be located within a wall of the reservoir base 5112 and/or a wall of the reservoir lid 5114, for example integrally by overmoulding or as a separate component connected as a sub-assembly. In such an arrangement the compliant portion would not be located between the reservoir base 5112 and the reservoir lid 5114 but within the reservoir base 5112 and/or the reservoir lid 5114. There may be more than one compliant portion 5116 or the compliant portion may be formed in multiple parts to provide more compliance in movement of the reservoir 5110.

5.5.2.2.3 Water Reservoir Base 5112

According to one arrangement, the reservoir base 5112 comprises a conductive portion (such as the base conductor plate 5152, e.g., see FIG. 12) configured to thermally couple with a heater plate 5120 of the humidifier 5000. The conductive portion improves efficiency of heat transfer from the heater plate 5120 to the volume of liquid in the reservoir 5110. All or a part of the base conductor plate 5152 may be made of a heat conducting material such as aluminium (e.g. approximately 2 mm thick, such as 1 mm, 1.5 mm, 2.5 mm or 3 mm) or another heat conducting material such as metal. In some cases, suitable heat conductivity may be achieved with less conductive materials of suitable thickness.

The reservoir base 5112 may also be configured as a receptacle to retain the given, maximum volume of liquid that the reservoir 5110 is configured to hold. In one form, the base 5112 may comprise further features such as an overfill prevention feature as will be described in further detail below. In one form, the reservoir base 5112 may also comprise a base upper body 5146 and a base bottom plate 5148, which together with the base conductor plate 5152 may form a receptacle, e.g., see FIG. 12.

The base upper body 5146 and/or the base bottom plate 5148 may be constructed from a bio-compatible material suitable for retaining the volume of liquid, such as a plastic or thermoplastic polymer, for example, ABS or polycarbonate material. The base conductor plate 5152 may comprise of a sealing element 5150, e.g., see FIG. 12, which may be integrated to, and/or sealingly connected to both the base upper body 5146 and the base bottom plate 5148 to prevent egress of water from the water reservoir 5110, particularly from the base 5112. For example, the sealing element 5150 may be overmoulded onto the base conductor plate 5152, and the resulting component may be secured between the base upper body 5146 and the base bottom plate 5148.

In one form as shown in FIG. 12, the base 5112 may comprise a base upper body 5146, a base bottom plate 5148, and a base conductor plate 5152. However, it should be appreciated that the reservoir base 5112 may be constructed in any number of parts. The reservoir base 5112 may be constructed as a single part made of, for example, aluminium or another heat conducting material such as metal. In another arrangement, the reservoir base 5112 may be constructed in two parts, for example comprising a lower component and an upper component. In such an arrangement, the lower component may be constructed from a heat conducted material and perform the roles of the base conductor plate 5152, sealing element 5150 and base bottom plate 5148, and the upper component may be equivalent to the base upper body 5146, and be constructed of a polycarbonate material.

In one form, the reservoir base 5112 may further comprise an inner lip 5224 and/or an outer lip 5226, for example as shown in FIG. 53 and FIG. 54. According to one aspect, the inner lip 5224 and/or outer lip 5226 may prevent egress of liquid from the reservoir 5110 through the interface between an intermediate portion 5202 (e.g. the compliant portion 5116) and the base 5112, for example when the intermediate portion 5202 is compressed, or when the intermediate portion 5202 is under vibration.

5.5.2.2.4 Water Reservoir-to-Humidifier Connection

When in use, the water reservoir 5110 receives the flow of air for example output by the RPT device 4000. In one form, the water reservoir 5110 is removably coupled with the humidifier 5000 as shown in FIGS. 13 to 16 by inserting the water reservoir into the water reservoir dock 5130, for example by sliding. The inlet 5118 of the water reservoir 5110 is configured to receive the flow of air that is output by the RPT device 4000, and to direct the flow of air into the water reservoir 5110. Humidity (i.e. water vapour) is added to the flow of air as the air travels through the reservoir 5110, and the humidified flow of air exits the reservoir 5110 through the outlet tube 5126 and to the reservoir outlet 5122. The reservoir outlet 5122 is connectable to an air circuit 4170 to deliver the flow of humidified air to the patient 1000.

Figure 16:
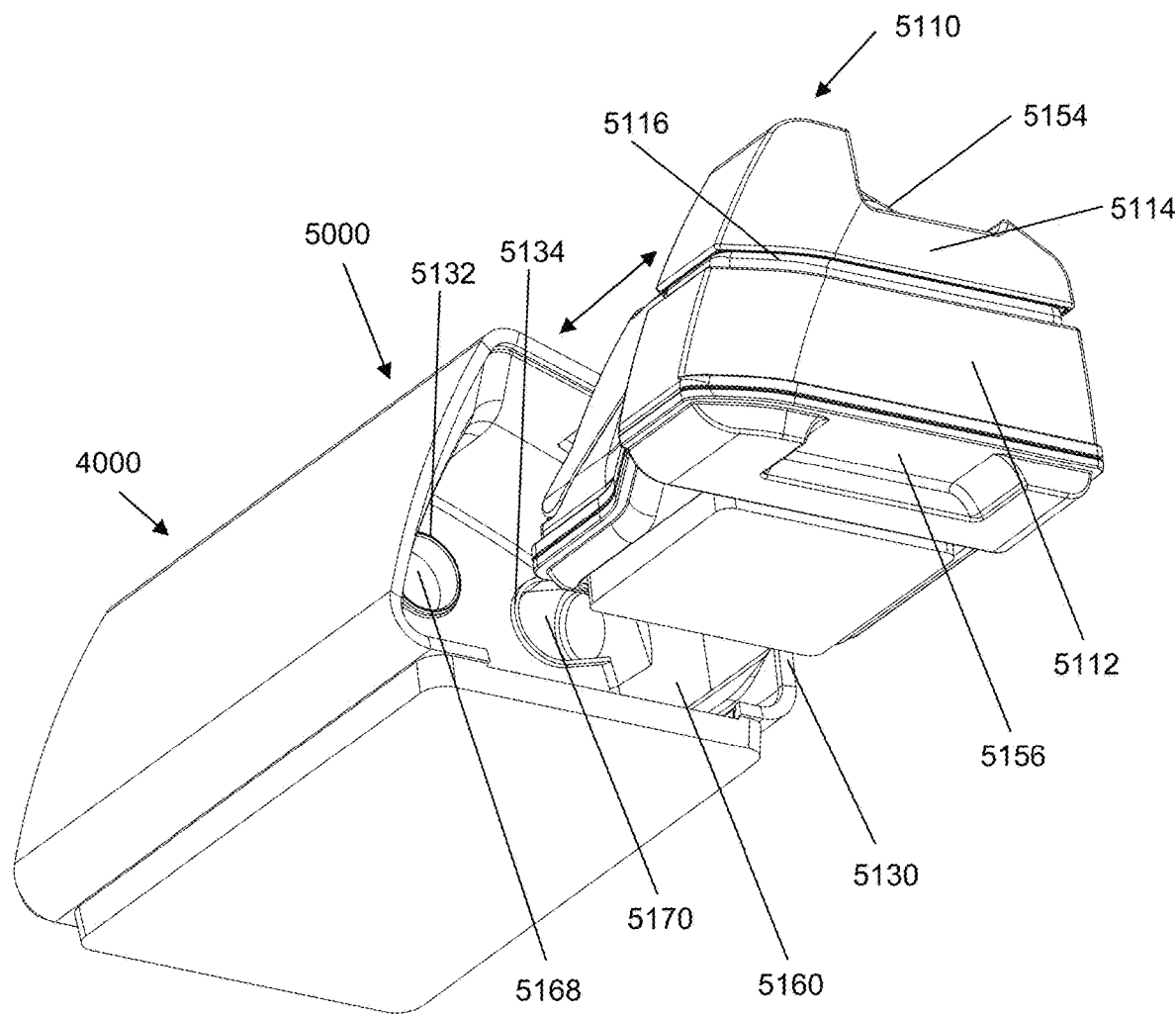
Figure 17B:
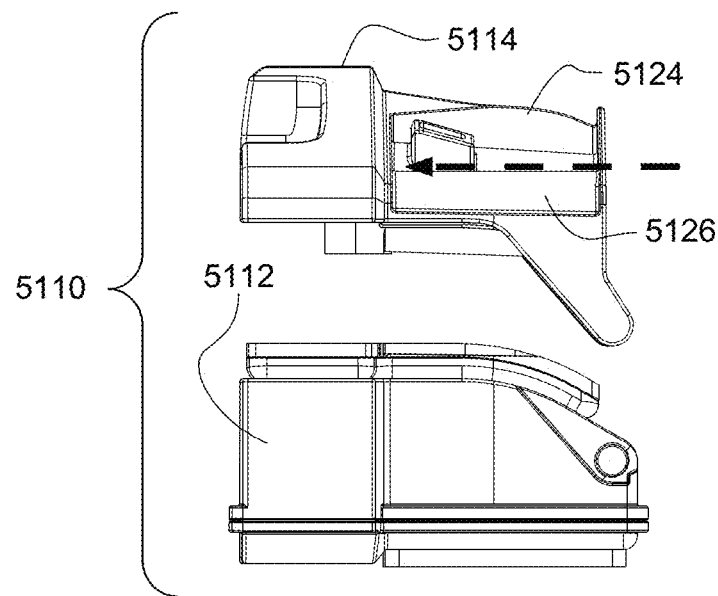
Figure 17A:
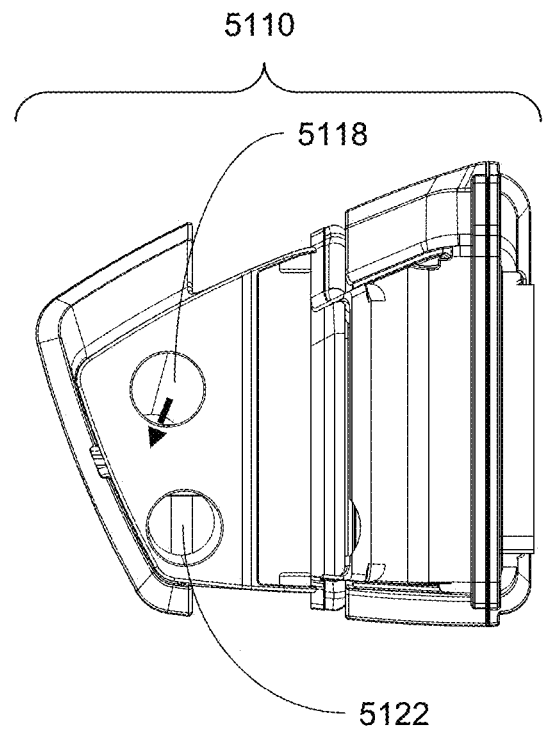
Figure 17C:
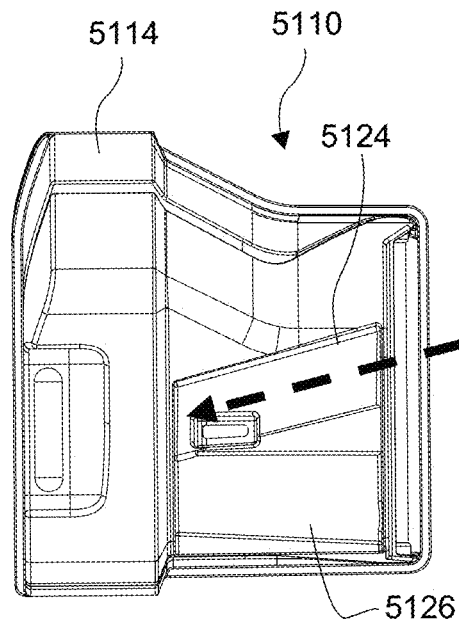

The double-ended arrows in FIG. 14 and FIG. 16 show the direction of relative motion, i.e. generally horizontal movement, between the humidifier 5000 and the water reservoir 5110 in connection and disconnection with each other in this arrangement. However, the water reservoir 5110 may be coupled to the humidifier 5000 by other methods such as insertion in a generally vertical direction, connection by one or more intermediate components (e.g. tubes) or being integrally formed with a humidifier.

In an alternative arrangement, not shown, the water reservoir 5110 may be inserted into the dock cavity 5160 from a vertical direction rather than using a sliding motion. In such an arrangement the dock cavity of the humidifier 5000 may comprise a moveable cover portion, such as a lid or top portion, which is at least partially opened to allow insertion of the water reservoir 5110 and closed following insertion to secure the water reservoir 5110 within the dock cavity 5160.

In the illustrated arrangement (see FIG. 16) the reservoir outlet 5122 is connectable to the reservoir dock air inlet 5170, through which the humidified flow of air travels to the humidifier outlet 5172. The humidifier outlet 5172 is connectable to the air circuit 4170 as indicated in FIG. 13 by the double-ended dotted arrow (see FIG. 13). An advantage of such an arrangement is that the humidifier reservoir 5110 can be removed from the dock cavity 5160 while the air circuit 4170 remains attached to the humidifier outlet 5172. Thus the insertion and removal of the humidifier reservoir 5110 is independent of the connection of the air circuit 4170. A further advantage is that the humidifier reservoir 5110 must be removed from the reservoir dock 5130 to fill the humidifier reservoir 5110 with liquid. In this form, neither of the inlet 5118 and the outlet 5122 of the reservoir 5110 are exposed while the reservoir 5110 is inserted in the humidifier 5000 in an operating configuration, while the reservoir 5110 itself remains accessible to the patient 1000, for example to allow easy removal from the humidifier 5000. This arrangement may reduce the likelihood of the user over-filling the water reservoir 5110 over the given, maximum volume of liquid, as the humidifier reservoir 5110 incorporates features to prevent over-filling as described further below. Still further, as the user is encouraged to remove the water reservoir 5110 to fill the reservoir 5110 with liquid, the likelihood of spillage of water onto, or into, the humidifier 5000 and/or the RPT device 4000 is reduced.

As shown in FIG. 16, first and second dock seals 5132, 5134 may be provided to help seal the connection between the reservoir inlet 5118 and the dock 5130 and the connection between the reservoir outlet 5122 and the dock 5130.

Figure 15:
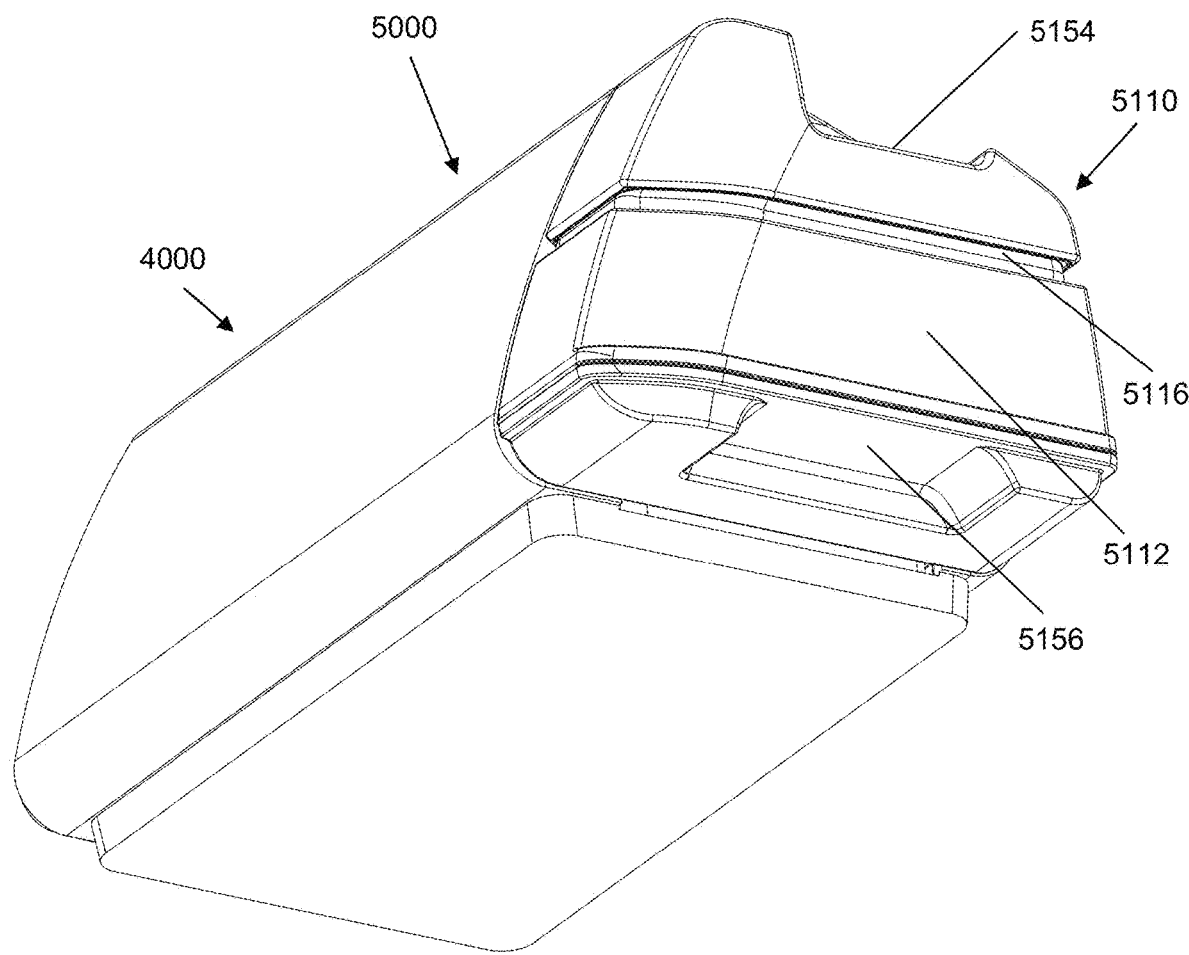

In the arrangement shown in FIGS. 15 and 16, the water reservoir 5110 is connected with the humidifier 5000 by placing the water reservoir 5110 in the water reservoir dock 5130. In this arrangement, the heights and shapes of the dock internal cavity 5160 and the water reservoir 5110 are such that to engage the water reservoir 5110 with the water reservoir dock 5130 the compliant portion 5116 is compressed, for example by between about 1 mm and about 5 mm, for example by about 2 mm, about 3 mm or about 4 mm. Thus, the shape of the portion of the water reservoir 5110 that is inserted into the dock 5130 is complementary to the shape of the dock cavity 5160 and the height of the water reservoir 5110 when compliant portion 5116 is compressed is slightly less than the height of the dock cavity 5160 to enable the insertion of the water reservoir 5110 into the dock cavity 5160.

The compliant portion 5116 may be constructed with a cross-section shape such as one shown in FIG. 39. A compressive force is required to sufficiently compress the compliant portion 5116 and allow relative movement (i.e. sliding) between the water reservoir 5110 and the water reservoir dock 5130. For example a compression force as measured at the handle recesses 5154, 5156 of between about 10 N and about 30 N, or about 20 N, or some other compression force is required to allow insertion of the water reservoir 5110 into the dock cavity 5160. The vertical gap achieved between the water reservoir 5110 and the dock internal cavity 5160 during insertion (or removal) may be between about 1 mm and about 5 mm, for example about 2 mm, 3 mm or 4 mm, when this compressive force is applied at the handle recesses and the water reservoir 5110 is inserted into the reservoir dock 5130. The water reservoir 5110 and the reservoir dock 5130 may be arranged so that the amount of compression in the compliant portion 5116 is reduced once the water reservoir 5110 is connected with the reservoir dock 5130 and the patient 1000 is no longer applying a compressive force. The reduction in compression may be between about 0.5 mm and about 2.5 mm, for example about 1 mm, 1.5 mm or 2 mm.

The compliant portion 5116 may be constructed from an elastomeric material such as silicone, thermoplastic elastomer (TPE), TPE polyester, TPE polyurethane or natural rubber. In choosing the material to be used for the compliant portion 5116 it may be advantageous to choose one that does not experience mechanical relaxation across the range of storage and operational temperatures that the compliant portion 5116 may be exposed to. One example of a material for the compliant portion 5116 which meets these requirements may be silicone.

A reservoir latch 5186 may be provided on the water reservoir 5110, as shown in FIG. 40, so that when the reservoir latch 5186 is engaged, it secures the reservoir lid 5114 and reservoir base 5112 together. The latch 5186 may prevent the reservoir lid 5114 and the reservoir base 5112 from separating and maintain the compliant portion 5116 in sealing engagement between the lid 5114 and the base 5112, for example by compression. In one form, the latch 5186 may be configured to restrict relative movement of the lid 5114 in relation to the base 5112 in one direction only, thus allow further compression of the compliant portion 5116 while preventing separation of the lid 5114 and the base 5112. This may allow insertion of the water reservoir 5110 into the reservoir dock 5130, and/or allow the compliant portion 5116 to assist thermal engagement between the reservoir 5110 and the heater plate 5120 as described elsewhere in this disclosure.

5.5.2.2.5 Reservoir Handles 5154, 5156

FIGS. 13 to 16 show an upper handle 5154 that is located on the reservoir lid 5114, and a lower handle 5156 that is located on the reservoir base 5112. These handles are intended to assist the patient (or user) 1000 to grip and hold the water reservoir 5110. In the shown arrangement, the handles 5154, 5156 are located away from the hinges 5158 such that, by holding the reservoir 5110 by the handles 5154, 5156, the patient 1000 imparts forces onto the reservoir 5110 compressing the compliant portion 5116, which pushes the lid 5114 and the base 5112 towards each other. A compression force may also help maintain the compliant portion 5116 in sealing engagement between the reservoir base 5112 and the reservoir lid 5114, such as during transport to/from re-filling the reservoir 5110 with liquid. It is to be understood that the handles 5154 and 5156 may be placed on other components or areas of the water reservoir 5110.

A handle grip 5166 may be provided on a surface of either or both of the handles 5154, 5156 as shown in FIG. 14. The handle grip 5166 may be constructed to assist the patient 1000 to hold the reservoir 5110, such as by being made from a higher friction material, made in a higher friction texture and/or made into an easier-to hold shape than the surrounding areas of the reservoir 5110. For example, the handle grip 5166 may be constructed from an elastomeric material such as silicone whereas the water reservoir 5110 may primarily be constructed from a polycarbonate material. Additionally, or alternatively, the handle grip 5166 may comprise geometric features such as ribs or ridges to reduce a chance of slippage between fingers and the handles 5154, 5156.

5.5.2.2.6 Air Flow Path

In one form of the present technology the flow of air is guided to travel through the reservoir 5110 in a tortuous path between the inlet 5118 and the outlet 5122. This prevents any 'short-circuiting' of the flow of air, which may lead to inadequate humidity in the flow of air which is delivered to the patient 1000.

Figure 18B:
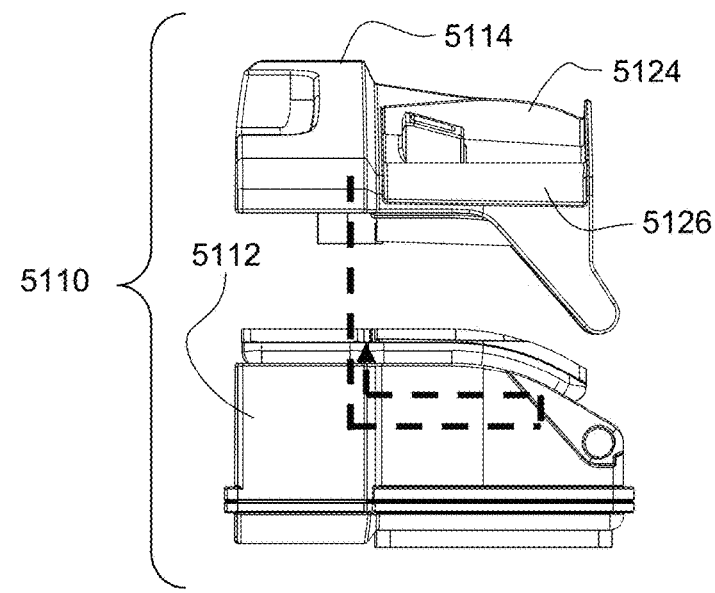
Figure 18A:
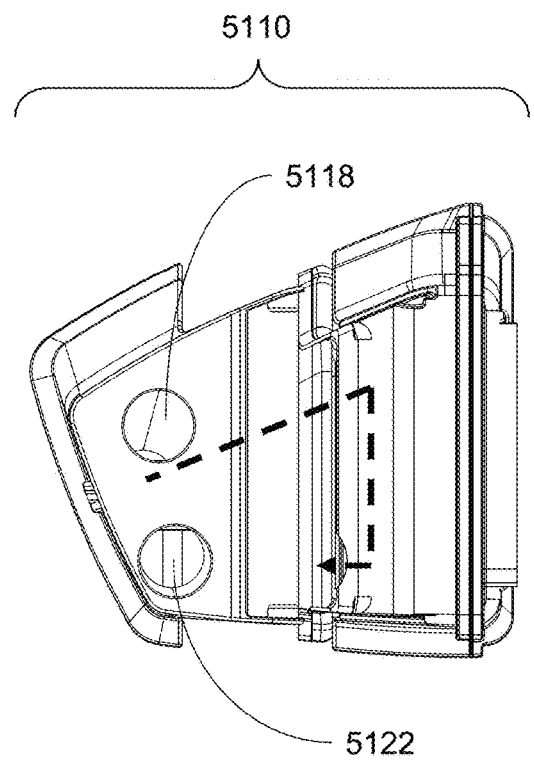
Figure 18C:
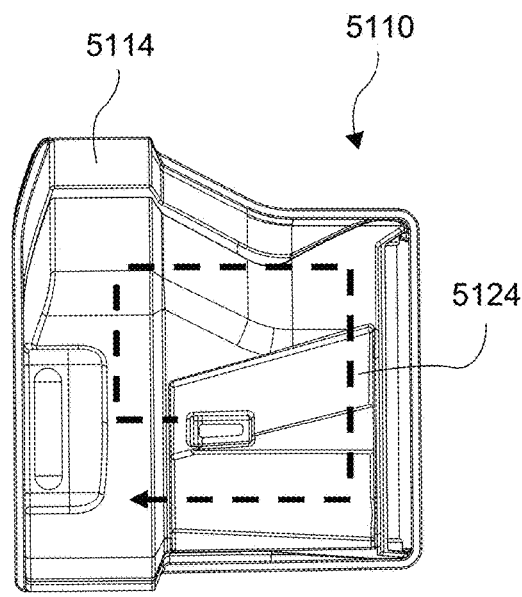
Figure 19B:
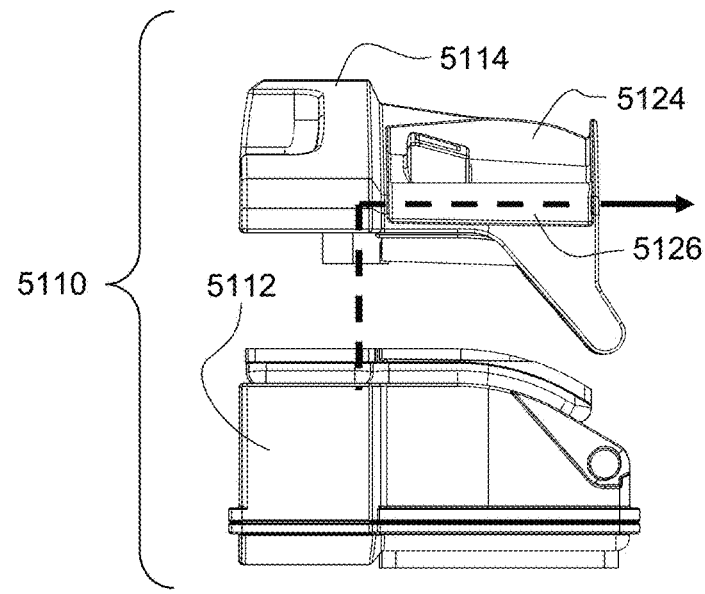
Figure 19A:
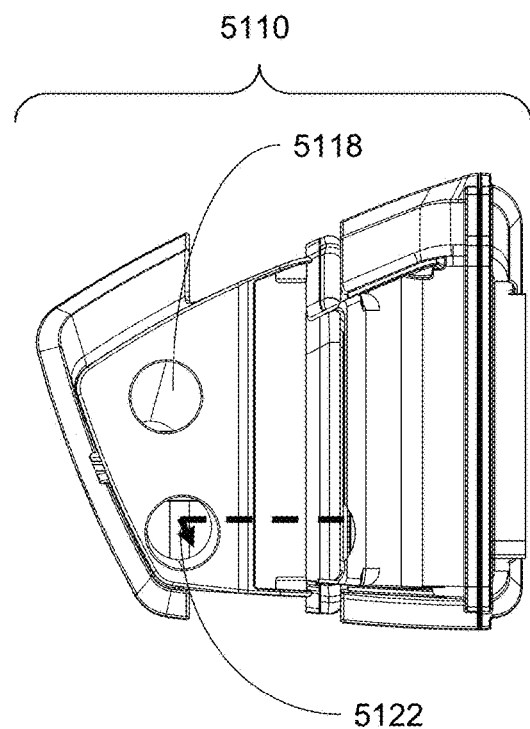
Figure 19C:
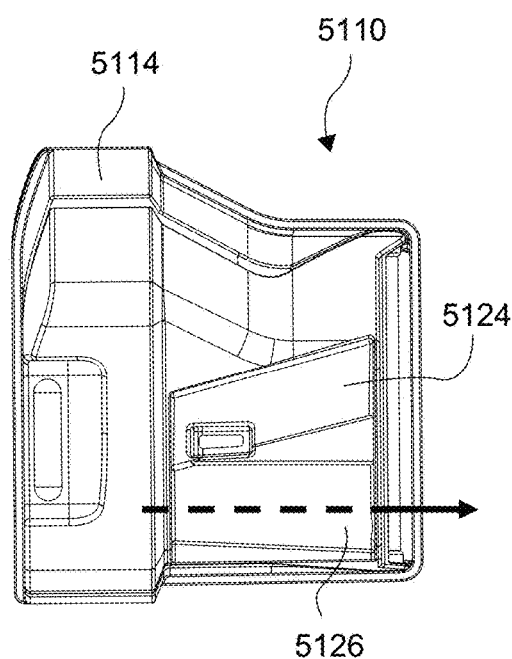

FIGS. 17a to 17c, 18a to 18c, and 19a to 19c show an exemplary path of the flow of air through the reservoir 5110 as it enters through the inlet 5118 and exits through the outlet 5122. The figures are arranged chronologically in three distinct orthogonal views per figure to visually demonstrate the exemplary flow path. In this arrangement the flow of air received through the inlet 5118 passes through the inlet tube 5124 (FIGS. 17a to 17c), into the internal volume of the water reservoir 5110 (FIGS. 18a to 18c). The flow of air then passes through the outlet tube 5126 to exit the water reservoir 5110 at the outlet 5122 (FIGS. 19a to 19c) as humidified air. FIGS. 17a to 17c, 18a to 18c, and 19a to 19c show the reservoir 5110 with the lid 5114 and the base 5112 in exploded view orientation for clarity, and any flow of air that occurs in the internal volume of the reservoir 5110 is shown in dotted lines. The dotted arrows shown indicate the general direction of the exemplary flow of air, although it is noted that the nature of air flow means that any air flow path includes swirling (e.g. turbulence) of the air rather than a straight and direct air flow path.

In some forms of the present technology, the reservoir 5110 may comprise flow elements, such as a baffle 5192 shown in FIG. 42, configured to increase the length of the tortuous flow path and/or to prevent ingress of water into the inlet tube 5124 and/or the outlet tube 5126. For instance, the reservoir 5110 may comprise a deflector portion 5198 as shown in FIGS. 41a, 41b, 42, 43a, 43b, and 44, or a deflector portion 5198 and a flow director 5195 as shown in FIGS. 47a and 47b. In some arrangements, the baffle 5192 may further comprise a locating portion 5196 as will be described in further detail below.

In the arrangement shown in FIGS. 41a, 41b, 42, 43a, 43b, and 44, the deflector portion 5198 is configured to prevent the flow of air from entering the outlet tube 5126 immediately after exiting the inlet tube 5124 through the inlet tube inner end (or inner tube outlet) 5125 (i.e. short-circuiting). In some of the arrangements (e.g., as illustrated in FIGS. 41a, 41b, 42, 43a, 43b and 44) the outlet tube 5126 may be formed as part of the intermediate portion 5202 and connect to the outlet 5122 of the reservoir when assembled with the lid portion 5114. When the intermediate portion 5202 and the lid portion 5114 are assembled together as seen in FIG. 41a, the deflector portion 5198 may be located close to the inlet tube inner end 5125, such as by abutting it. In this arrangement, the deflector portion 5198 forms a cover between the inlet tube inner end 5125 and a base of the outlet tube inner end 5127. This cover may be further advantageous in that it forces the flow of air to travel in a channel created by the cover and the volume of water in the reservoir 5110 for improved humidity pickup.

In the arrangement shown in FIGS. 47a and 47b, the reservoir 5110 includes a flow director 5195 as well as a deflector portion 5198. The deflector portion 5198 is configured to prevent short-circuiting of the flow of air, and the flow director 5195 is further configured to direct the flow of air that exits the inlet tube 5124 in a direction approximately parallel with the volume of liquid in the reservoir 5110. This may ameliorate occurrence of 'spitting', which can occur when the flow of air exits the inlet tube 5124 in a direction normal to the surface of the volume of liquid.

Figure 22:
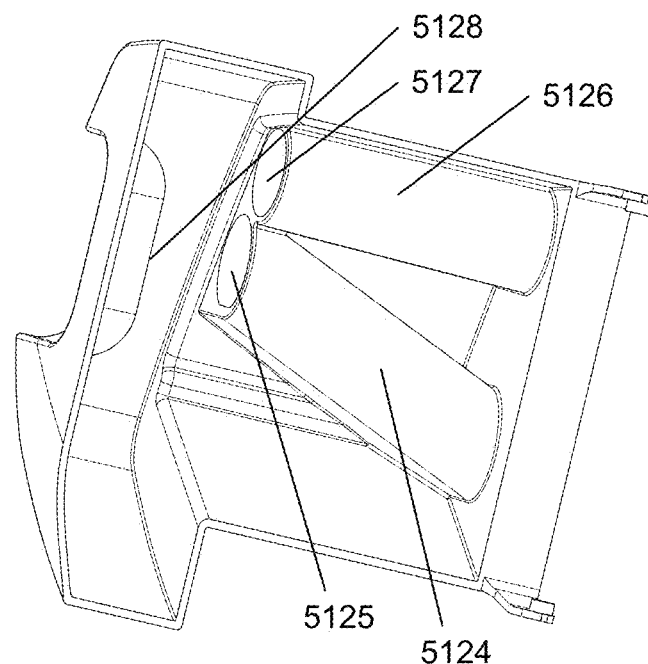
Figure 23:
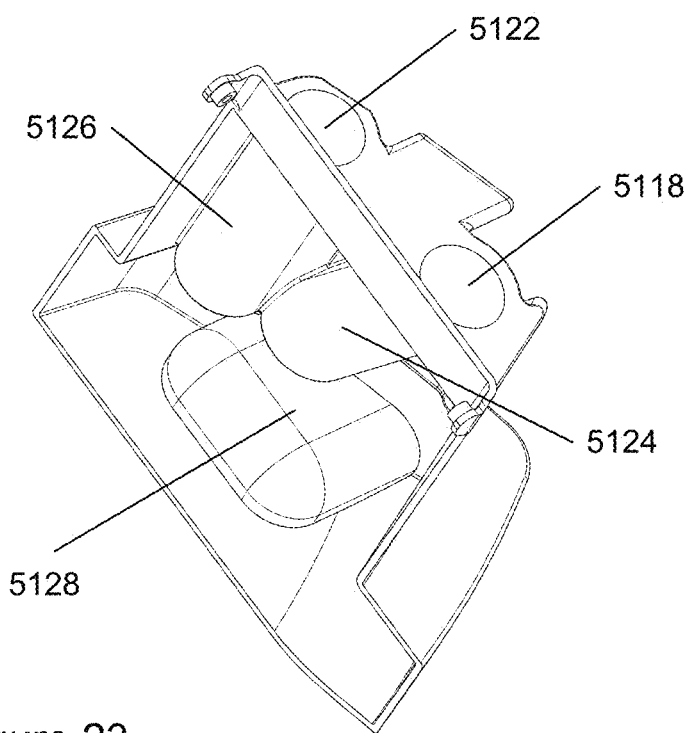
Figure 24:
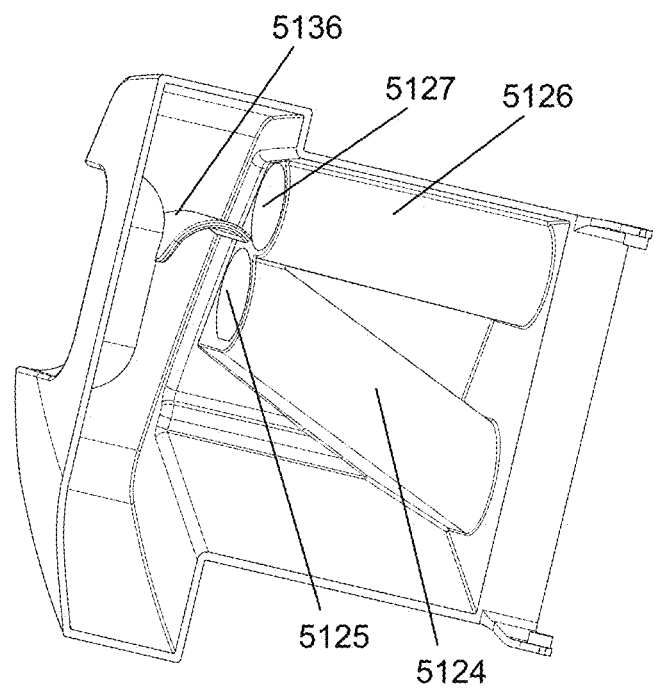
Figure 25:
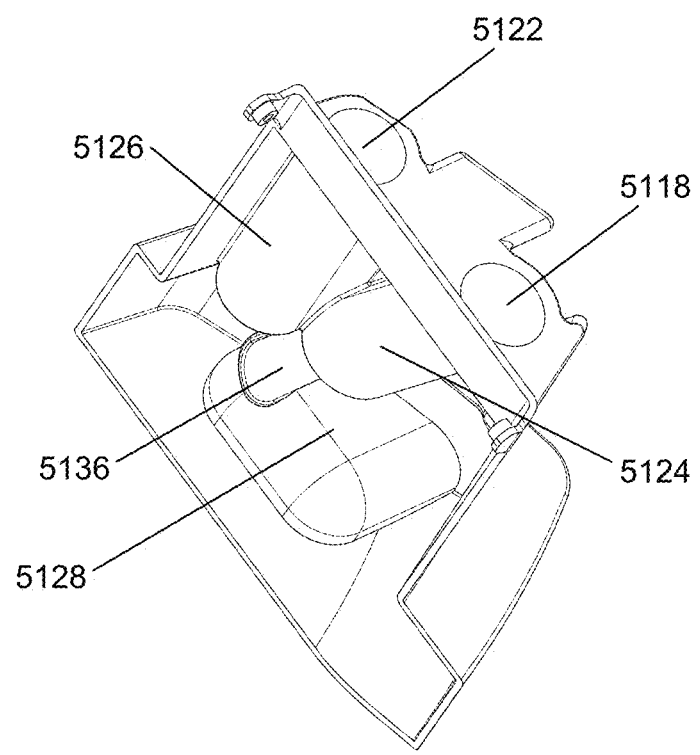
Figure 26:
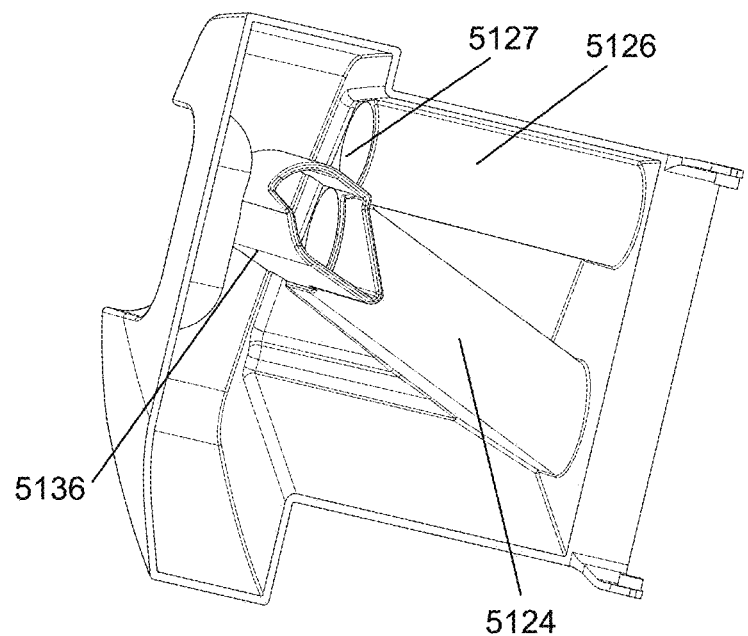
Figure 27:
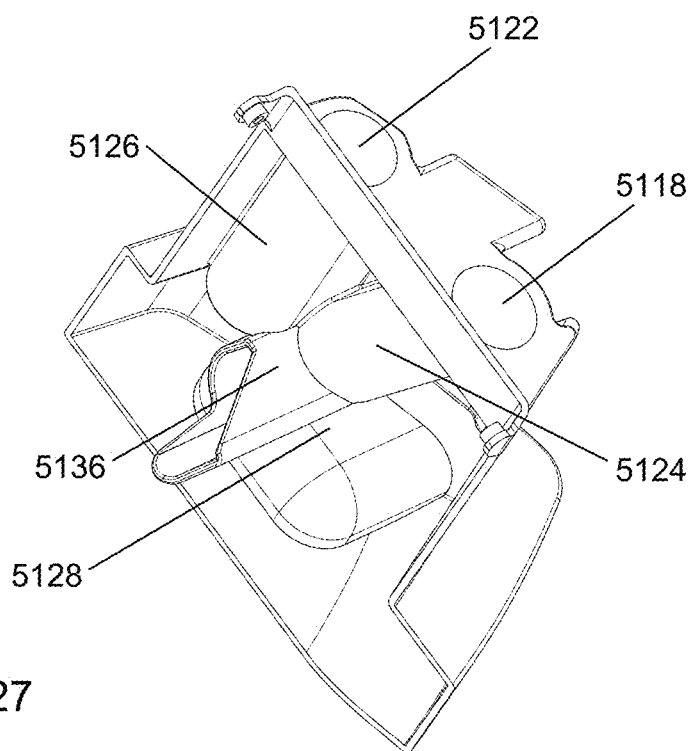

As shown in FIGS. 22 and 23, the reservoir 5110 may include an end wall 5128 that is near and opposed to the inlet tube inner end 5125. The inner end wall 5128 of the reservoir 5110 directs air exiting the inlet tube 5124 to flow across the water surface before it reaches an outlet tube inner end 5127 and flows out of the outlet 5122 through the outlet tube 5126. FIGS. 24 to 27 show examples of other arrangements of flow elements, wherein the reservoir 5110 may include a turning vane 5136 which is placed near the interior end 5125 of the inlet tube 5124. The turning vane 5136 may be integrally formed as an extension of the inlet tube 5124 as shown in FIGS. 26 and 27, or the turning vane 5136 may be a separate component located adjacent to or coupled with the inlet tube 5124. The turning vane 5136 may also be profiled as shown in FIGS. 26 and 27.

The path of the flow of air demonstrated in FIGS. 17a to 17c, 18a to 18c, and 19a to 19c is exemplary only, and is aimed to demonstrate one of many paths that the flow of air may traverse through the water reservoir 5110, namely that it enters the water reservoir 5110 through the inlet 5118 and exits through the outlet 5122 after experiencing some degree of swirling within the volume of the water reservoir 5110. A person skilled in the art would understand that the particles or molecules that form the flow of air may not follow a single path within the water reservoir 5110 due to a number of factors, including, for example, localised turbulence (eddies) or pressure gradients within the water reservoir 5110. As a result, the cumulative path of the flow of air may comprise any number of paths wherein it experiences various degrees of 'swirling' within the water reservoir 5110 prior to exiting via the outlet tube 5126 at the outlet 5122.

It is also possible that some small portion of the flow of air may escape the water reservoir 5110 as a leak.

5.5.2.2.7 Thermal Contact/Engagement

According to one aspect of this technology, the water reservoir 5110 and the heater plate 5120 of the humidifier are in thermal contact, or thermal engagement, as described above. A degree of thermal contact, for example measured in thermal conductivity or thermal contact resistance, between two components may vary according to a number of parameters.

In the prior art, additional components have been used to improve thermal contact between a water reservoir and a heater plate by increasing the contact pressure therebetween. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

5.5.2.2.7.1 Pre-Compression for Improved Thermal Contact

In the present technology, pre-compression of the water reservoir 5110, for example in engagement with the water reservoir dock 5130, may be used to help improve thermal contact between the reservoir 5110 and the heater plate 5120.

In one arrangement, the water reservoir 5110 may be configured so that in its operating configuration, such as when it is placed in the water reservoir dock 5130, the compliant portion 5116 is compressed as described above. The reservoir 5110 and the reservoir dock 5130 may be further configured so that a reaction force to the compression of the compliant portion 5116 pushes the base 5112 of the water reservoir 5110 against the heater plate 5120 to improve the thermal contact therebetween.

Thus, the compliant portion 5116 may act as a spring that is biased to push the reservoir base 5112 and/or the reservoir lid 5114 in a direction perpendicular to the heater plate 5120. As the reservoir 5110 is secured externally, such as confined within the reservoir dock 5130, the compression of the compliant portion 5116 is reacted by a force that encourages improved thermal engagement with the heater plate 5120. FIG. 20 illustrates this effect by indicating the distributed forces or pressures that are applied to the lid 5114, compliant portion 5116 and the base 5112 by the arrows shown.

The force required for compression of the compliant portion 5116 when the water reservoir 5110 is connected with the humidifier 5000 is preferably in the same direction as the normal to a surface of the conductive portion. The direction may be also preferably in the same direction as the direction of thermal engagement. This force is reacted by the water reservoir dock 5130 at its contacting points and/or surfaces, thereby pushing the base 5112 of the water reservoir 5110 and the heater plate 5120 together.

The magnitude of compression force may be between about 5 N and about 15 N when measured at the heater plate 5120 when the water reservoir 5110 is placed in the water reservoir dock 5130. However, it should be understood that different configurations of the water reservoir 5110 may require different magnitudes of compression force. The magnitude of this force may be altered by modifying the design of any or all of the compliant portion 5116, the lid 5114, the base 5112, or the reservoir dock 5130. For instance, if the compliant portion 5116 was constructed of a material with higher Young's modulus, it would correspondingly increase the magnitude of the force. It should be noted that FIG. 20 only shows forces and pressures in the vertical direction.

In some cases, the amount of compression of the compliant portion 5116 in the reservoir 5110 may be used to vary a level of thermal engagement between the conductive portion and the heater plate 5120.

5.5.2.2.7.2 Use of Pressurised Air for Improved Thermal Contact

According to another aspect, when the water reservoir 5110 is connected with the humidifier 5000, the flow of air received from the RPT device may pressurise a chamber such as the interior of the reservoir 5110. The pressurisation of the chamber may be used to increase a level of thermal engagement (i.e. thermal contact) between the reservoir 5110 and the heater plate 5120. The reservoir 5110 may be further configured so that by varying the level of pressure in the chamber may vary the level of thermal contact between the reservoir 5110 and the heater plate 5120.

In one form, the compliant portion 5116 may be configured to be expandable in the direction of thermal contact, and the reservoir 5110 may be confined by the reservoir dock 5130 in the same direction. In this form, the internal pressure pushes the base 5112 of the water reservoir 5110 against the heater plate 5120 to improve the level of thermal engagement between the heater plate 5120 and the base 5112.

FIG. 21 illustrates this effect by indicating the distributed forces or pressures that are applied to the lid 5114 and the base 5112 by the arrows shown. FIG. 21 shows forces and pressures in the vertical direction only, as in this form the thermal engagement occurs in the vertical direction. The presence of above-atmospheric pressure within the water reservoir 5110 results in forces in the direction of thermal engagement, and is reacted by the water reservoir dock 5130 at its contacting surfaces, thereby pushing the base 5112 of the water reservoir 5110 and the heater plate 5120 together in the direction of thermal engagement. The magnitude of this force may be between about 5 N and about 15 N when measured at the heater plate 5120 at 20 cm $H_2O$ of pressure.

It should be understood that different configurations of the water reservoir 5110 may require different magnitudes of force, which may be achieved by varying the surface area that the pressure acts on, or the effective pressure that acts on the surface. Such changes may be achieved, for example, by a pressure regulating valve.

In another arrangement, substantially the same effects as those described above may be achieved with a non-opening compliant portion of a water reservoir 5110. The water reservoir 5110 and the reservoir dock 5130 may be arranged so that elasticity or flexibility is provided by an elastomeric material or a joint that allows freedom of movement (e.g. a sliding connection, or a concertina section of pliable plastic or a flexible portion in the water reservoir) in the direction of the heat transfer. In this configuration the lid 5114 and the base 5112 may be unconstrained relative to each other in the direction of thermal contact. The reservoir 5110 may then be constrained in the direction of the heat transfer in another manner (e.g. by a water reservoir dock or a similar housing) to create a force that reacts to balance the pressure created in the interior of the reservoir 5110 by the pressurized flow of air, wherein some of the reaction force may occur at the heater plate 5120 to improve thermal contact. In such arrangements, another opening to re-fill the water reservoir 5110 may be introduced on the reservoir 5110, such as on the lid 5114, and it may comprise a separate seal around such opening.

FIG. 34 shows an example of such an arrangement, including a base 5174, a top 5176, a compliant portion 5178 and a re-filling cap 5180. The base, the top and the compliant portion may be affixed together in another arrangement, wherein re-filling of the reservoir would be accommodated by the re-filling cap 5180. The re-filling cap 5180 may be placed such that, when the humidifier reservoir 5110 is engaged with the reservoir dock 5130, the re-filling cap 5180 is not accessible. Such an arrangement may preserve the advantage described above, namely that the reservoir 5110 is not able to be re-filled while it is engaged with the reservoir dock 5130. Furthermore, the compliant portion 5178 may be replaced by any mechanism known in the art that is able to accommodate a change in vertical length within a reservoir.

In yet another alternate arrangement, the flow of air may be used to improve the level of thermal contact between the humidifier reservoir 5110 and the heater plate 5120 by pressurisation or inflation of a secondary component. The secondary component may be a chamber, body or surface that acts on the humidifier reservoir 5110, which in turn pushes the water reservoir 5110 and the heater plate 5120 together in the direction of thermal engagement. Similarly, the secondary component may act upon the heater plate 5120 to push the heater plate 5120 and water reservoir 5110 together in the direction of thermal engagement.

The secondary component may be arranged externally to the reservoir 5110 and/or the heater plate 5120. Furthermore, the secondary component may be configured to vary the area in contact with the reservoir 5110 and/or the heater plate 5120, to further profile the change to thermal contact as pressure of the flow of air changes.

In an alternate arrangement, the water reservoir dock 5130 may include a retaining mechanism (for example, a lid that closes around the water reservoir 5110) to hold the water reservoir 5110 in its intended position. In such an arrangement, a reservoir dock lid may be configured to compress and/or confine the compliant portion 5116 in order to improve the level of thermal contact.

The level of thermal contact may also be further improved using a spring loaded or sprung heater plate as is known in the prior art. The heater plate may be constructed with a convex or domed shape towards the humidifier reservoir 5110 so that when the humidifier 5110 is engaged with the reservoir dock 5130 the convex heater plate is flattened, which generates a clamping force pushing the heater plate 5120 to the water reservoir 5110. Similarly, the conductor plate 5152 of the water reservoir 5110 may be domed or convex shaped and be configured to be flattened towards to the heater plate when the water reservoir 5110 is engaged in the dock cavity 5160 of the humidifier 5000.

Any one of the above means of improving thermal contact may be used independently of each other, or in any combination thereof, including in combination with any prior art means of achieving or improving thermal engagement between the humidifier reservoir and the heater plate.

5.5.2.2.8 Reservoir Inlet/Outlet

As described above, the reservoir inlet 5118 is configured to receive the flow of air into the reservoir 5110, and the reservoir outlet 5122 is configured to output the humidified flow of air. The inlet 5118 and/or the outlet 5122 are preferably further configured to prevent egress of liquid from the reservoir 5110 when the reservoir 5110 is displaced and/or rotated from its normal, working orientation. Still further, the inlet 5118 and/or the outlet 5122 are preferably configured to prevent short-circuiting of the flow of air as described above. In one form, the inlet 5118 may be configured to prevent 'spitting', or splashing, of liquid which may be caused by a jet of air impinging on the volume of liquid in the reservoir 5110.

In one arrangement as shown in FIG. 22, the reservoir inlet 5118 includes an inlet tube 5124 to provide a flow path for the inlet flow of air into the reservoir 5110, and the reservoir outlet 5122 includes an outlet tube 5126 to provide a flow path for the outlet flow of humidified air from the reservoir 5110.

In one configuration as shown in FIGS. 26 and 27, it may be advantageous to configure the turning vane 5136 so that the lowest portion of the turning vane 5136 extends below the lowest portion of the outlet tube 5126. This may further prevent ingress of water into the inlet tube 5124 from any 'spitting' of water.

The water reservoir 5110 is preferably configured to provide tilt spillback protection from the water flowing back through the outlet tube 5126 or the inlet tube 5124. Water egress through the inlet tube 5124 may be particularly undesirable as it may introduce water into the RPT device 4000 and damage electronic components (such as an electric motor, a flow sensor or a printed circuit board) from exposure to water.

In one arrangement of the present technology, the reservoir 5110 achieves spillback protection by arranging the inlet tube inner end 5125 so that when the reservoir 5110 is rotated by 90 degrees in any direction from its working, horizontal orientation the given maximum volume of water is able to be stored in the reservoir 5110 without reaching the inlet tube inner end 5125.

Figure 28:
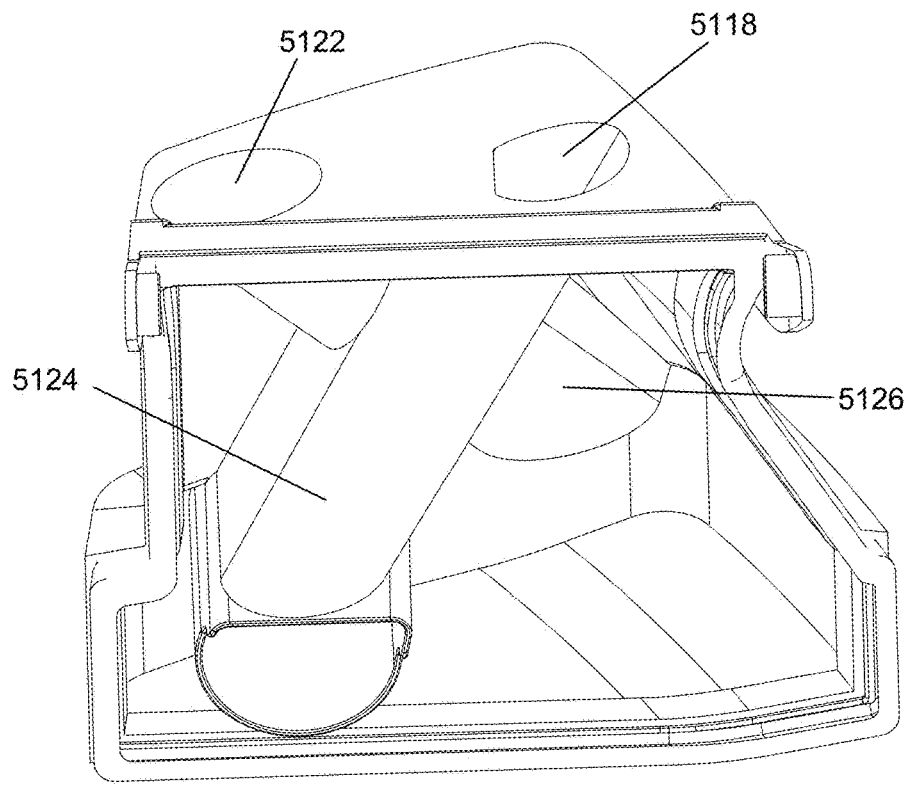
Figure 29:
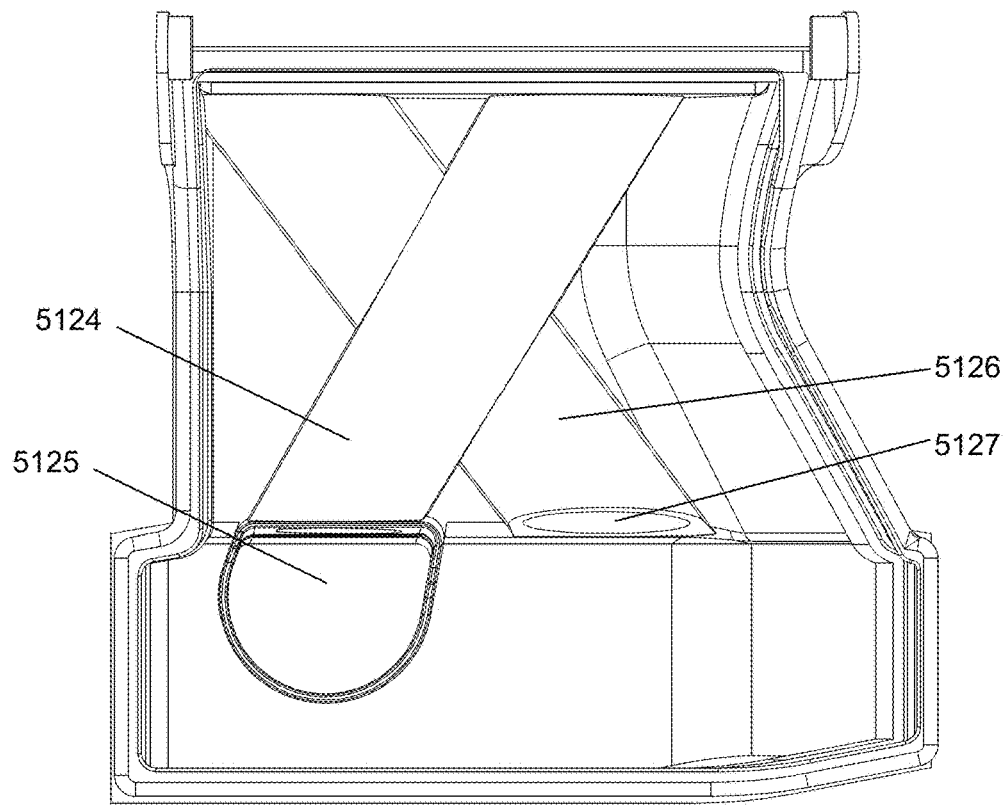

In another arrangement of the reservoir 5110, the axes of inlet tube 5124 and the outlet tube 5126 may intersect when viewed in a plane, such as from above as shown in FIGS. 28 and 29. The inlet tube 5124 and outlet tube 5126 may not be connected to each other as one of the tubes passes below the other tube, such as the inlet tube 5124 passes below the outlet tube 5126.

This configuration may improve the tilt spillback protection by arranging the inlet tube 5124 and the outlet tube 5126 such that when the reservoir 5110 is tilted away from its working orientation, water must reach the higher end of the inlet tube 5124 or the outlet tube 5126 to exit the reservoir 5110. For example, if the reservoir 5110 was tilted such that the water reaches the lower of the inlet tube inner end 5125, the water must still rise higher to reach the exterior end of the inlet tube 5124 or the inlet 5118 to exit the reservoir 5110 as shown in FIG. 29.

Figure 35:
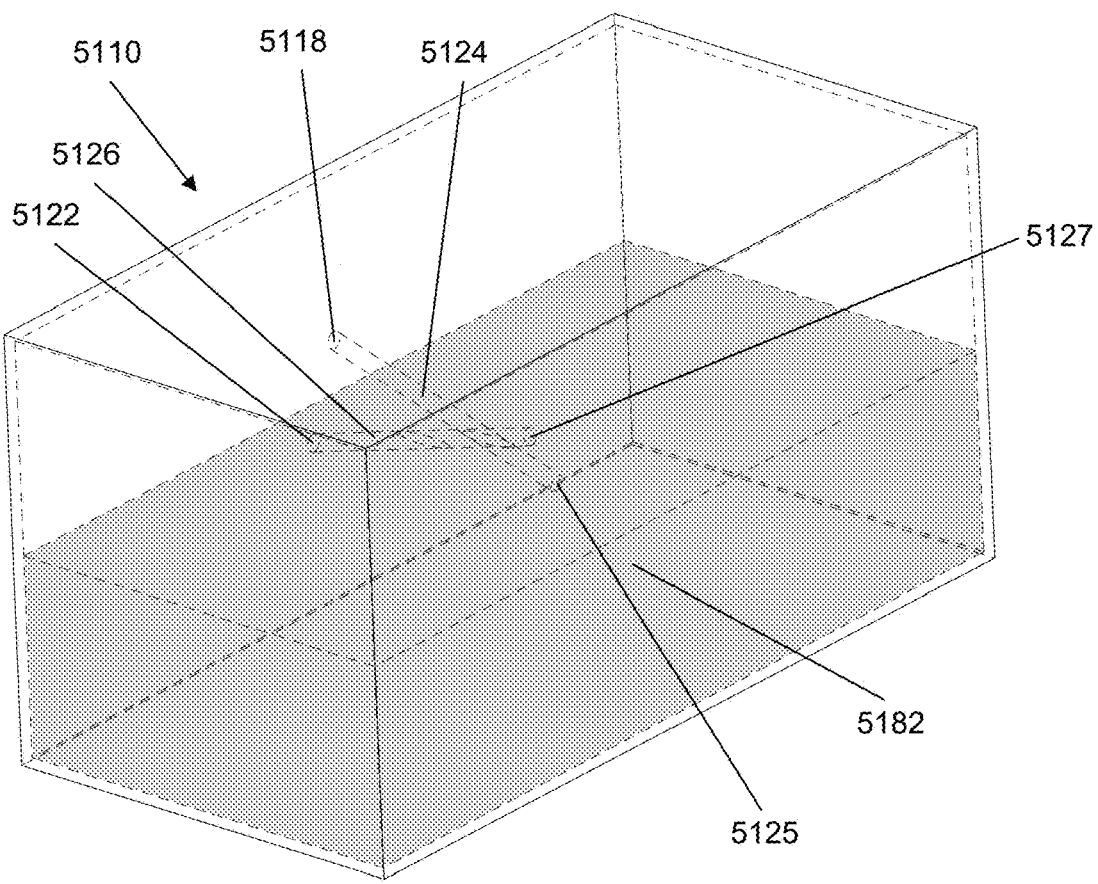
Figure 36:
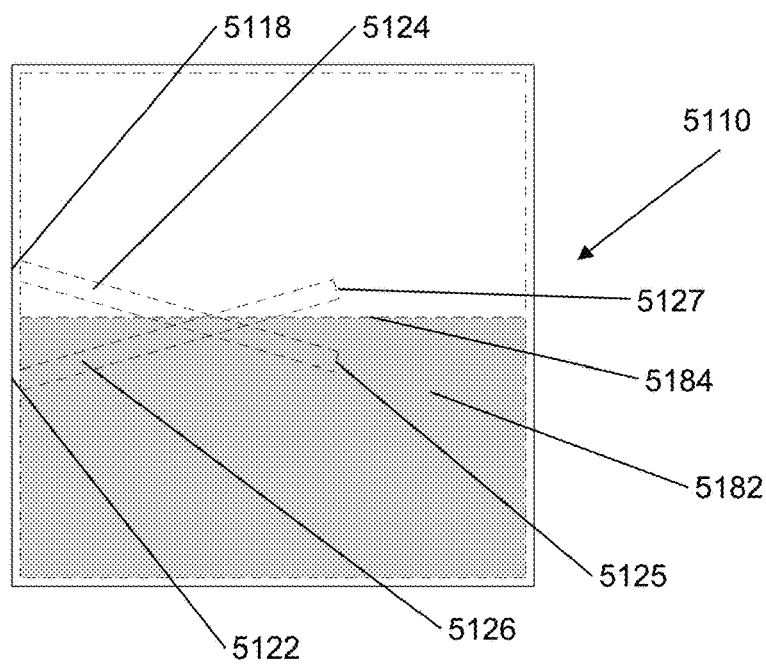
Figure 37:
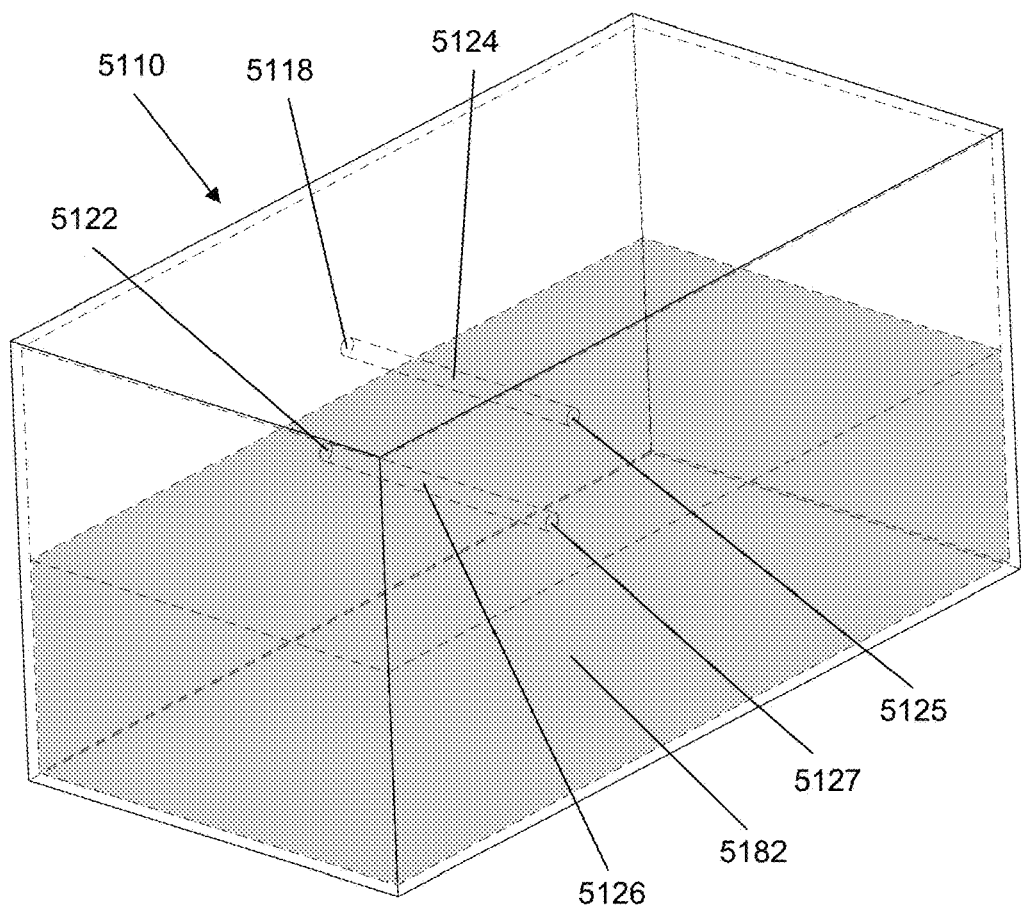
Figure 38:
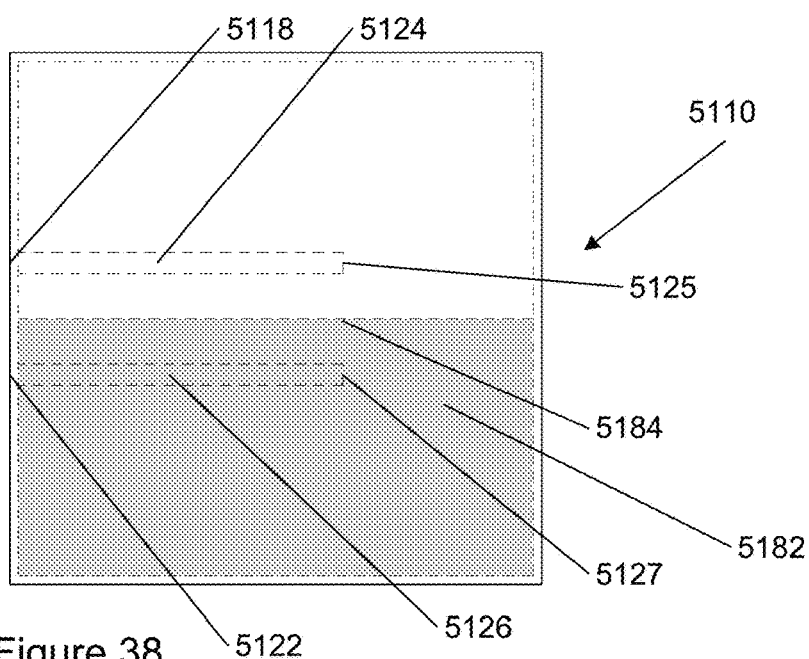

Simplified representations of the effects created by crossed inlet and outlet tubing are shown in FIGS. 35 to 38, wherein the internal surfaces are shown by dotted lines. These figures show alternate arrangements of a water reservoir 5110, with an inlet 5118 and an outlet 5122 that respectively include an inlet tube 5124 and an outlet tube 5126. FIGS. 35 and 36 show a configuration wherein the axes of the tubing intersect when viewed from the side (as shown in FIG. 36), and FIGS. 37 and 38 show an alternate configuration wherein the axes of the tubing are substantially parallel when viewed from the side (as shown in FIG. 38). In FIGS. 35 to 38, a volume of water 5182 is assumed to fill approximately half of the volume of the reservoir 5110, and the water level 5184 is indicated by the dotted lines extending horizontally.

When the water reservoir 5110 is oriented as shown in FIGS. 35 and 36, the arrangement of the inlet tube 5124 and the outlet tube 5126 requires the water level 5184 to rise above the higher end of the inlet tube 5124 or the higher end of the outlet tube 5126 if any water 5182 is to exit the water reservoir 5110. On the other hand, in the arrangement shown in FIGS. 37 and 38 the water level 5184 only needs to rise as high as a lower end of the inlet tube 5124 or the outlet tube 5126 in order to exit the water reservoir 5110.

As the water level 5184 will change as a function of the orientation of the water reservoir 5110, this effect of crossing the inlet tube 5124 and the outlet tube 5126 may be re-created at any orientation as required by re-orienting the inlet tube 5124 and the outlet tube 5126 to suit the shape of the water reservoir 5110. In some forms, the inlet tube 5124 and the outlet tube 5126 may be crossed when viewed from multiple angles orthogonal to each other.

In the forms shown in FIGS. 28 and 29 and FIGS. 35 to 38, inlet tube inner end 5125 and the outlet tube inner end 5127 are located within the cavity and the outer end of the inlet tube and the outer end of the outlet tube 5126 are located in one of the plurality of walls of the cavity at the inlet 5118 and outlet 5122 respectively. A first axis (inlet tube axis) is defined between the inlet tube inner end 5125 and the inlet 5118 and a second axis (outlet tube axis) is defined by the outlet tube inner end and the outlet 5122. When the reservoir is tilted (for example by approximately 90° to normal working orientation) the first axis is on a first angle such that the inlet tube inner end 5125 and the inlet 5118 are positioned at different heights, such that the predetermined maximum volume of water is below at least one of the inlet tube inner end 5125 or the inlet 5118 to prevent spillback of water through the inlet tube 5124. Furthermore, when the reservoir is tilted (for example by approximately 90° to normal working orientation) the second axis is on a second angle such that the outlet tube inner end 5127 and the outlet 5122 are positioned at different heights, such that the predetermined maximum volume of water is below at least one of the outlet tube inner end 5127 or the outlet 5122 to prevent spillback of water through the outlet tube 5126. This effect may be also created wherein the reservoir is tilted at any other angles, to suit the design and/or tilt conditions of the humidifier 5000 and/or reservoir 5110.

5.5.2.2.9 Reservoir Arrangement with Removable Inlet/Outlet Tubes

In a yet further example of the current technology, the reservoir 5110 may be configured as shown in FIGS. 41*a*, 41*b*, and 42. In this example, the reservoir 5110 comprises a lid portion 5114, an intermediate portion 5202 and a base portion 5112 (base portion not shown in FIGS. 41*a* and 41*b* for clarity). The lid portion 5114 and the intermediate portion 5202 may be configured to be releasably engaged to each other. They may be further configured to comprise a number of features when engaged to each other, such as an inlet 5118, an outlet 5122, an inlet tube 5124 and an outlet tube 5126, while being releasably engaged to each other. For example, the lid portion 5114 may comprise an inlet 5118, an outlet 5122 and an inlet tube 5124, and the intermediate portion 5202 may comprise an outlet tube 5126 as shown in FIG. 41*b*.

As shown, the intermediate portion 5202 may also comprise a carrier 5117, a baffle 5192 and at least one support spoke 5194. The support spokes 5194 may be provided for structural support and/or to position the outlet tube 5126 and/or the baffle 5192 on the intermediate portion. The baffle 5192 is arranged to block a direct air path (or short-circuiting as described above) between the inlet tube inner end 5125 and the outlet tube inner end 5127 to encourage movement of the airflow within the reservoir to improve humidity uptake by the airflow within the reservoir 5110. In addition a compliant portion 5116 may be either integrated with the intermediate portion 5202 as shown or may be formed as separate component to the intermediate portion.

An advantage of this arrangement may be improved cleanability of the reservoir 5110 by separating some of the components from the reservoir, such as the inlet tube 5124 and/or the outlet tube 5126. This arrangement may be particularly advantageous in such situations as when at least one of the inlet tube 5124 or the outlet tube 5126 extends into the internal volume of the reservoir 5110, as such features may hinder access to the interior of the reservoir 5110. It can be seen in FIGS. 41a and 41b that the intermediate portion 5202 is engaged with the lid portion 5114 in its normal working orientation. However, as the intermediate portion 5202 is separable from the lid portion 5114, the inlet tube 5124 and the outlet tube 5126 may be separated to improve access to the interior of the lid portion 5114.

By using two separable portions 5114, 5202 to construct the upper portion of the reservoir and/or configuring the inlet and/or outlet tubes 5124, 5126 to be releasably engaged to the reservoir 5110, the number of small, difficult-to-access areas may be reduced, which may improve cleanability of the reservoir 5110. Furthermore, the removable inlet tube 5124 and/or the removable outlet tube 5126 may be themselves more easily accessible for cleaning as well.

In another example of the current technology (not shown), the lid portion 5114 and the intermediate portion 5202 may each comprise parts of a feature, wherein they would combine to form a complete feature. For instance, the lid portion 5114 may comprise a part of the inlet tube 5124 and a part of the outlet tube 5126, and the intermediate portion 5202 may comprise another part of the inlet tube 5124 and another part of the outlet tube 5126. Those skilled in the art will understand that the reservoir may be further sub-divided into any number of separable portions, and separable features such as the inlet tube 5124 and/or the outlet tube 5126 may be located in any number of arrangements in relation to the separable portions.

Another advantage of the current arrangement may be to improve spillback performance (prevention of liquid egress through the inlet tube 5124 and/or outlet tube 5126) of the reservoir 5110. Spillback performance may be improved by increasing the internal volume of the reservoir 5110, which may be achieved by introduction of a void above the inlet tube 5124 and/or the outlet tube 5126.

Another method of improving spillback performance is to arrange the inlet tube inner end 5125 and/or the outlet tube inner end 5127 proximal to the center of the reservoir 5110, e.g., proximal to a centroid of the reservoir volume. In this configuration, the maximum water level that is able to be stored in the reservoir 5110 without reaching the inlet tube inner end 5125 and/or the outlet tube inner end 5127 is the same when the reservoir 5110 is rotated by 90 degrees in any direction from its working horizontal orientation. In example, such configuration of the inlet tube 5124 and/or outlet tube 5126 may be provided by a single molded component, e.g., by combining horizontal and vertical molding tools to form the inlet tube 5124 and/or outlet tube 5126 in the desired arrangement. As a reservoir 5110 is typically produced by injection molding, forming an inlet tube 5124 and/or an outlet tube 5126 as a part of the lid 5114 prohibits introduction of a void above the inlet tube 5124 and/or the outlet tube 5126. In such a configuration, a molding tool comprising the internal volume of the lid 5114 would be pinned in place by the inlet tube 5124 and/or the outlet tube 5126 and thus molding would not be possible, or require a complex and costly tooling arrangement. In such a case, the ability to separate the inlet tube 5124 and the outlet tube 5126 may be further advantageous.

It will be understood that the lid portion 5114, the intermediate portion 5202 and the base portion 5112 may be configured in any number of ways. For instance, the relative sizes of the lid portion 5114 and the base portion 5112 may vary, and the lid portion 5114 and/or the base portion 5112 may further comprise multiple materials or components in its construction. One or more of the inlet tube 5124 and the outlet tube 5126 may be removably or releasably coupled to the lid portion 5114 or the base portion 5112, for example as a part of the intermediate portion. The intermediate portion may also be configured to initially engage the lid portion 5114 and/or the base portion 5112, for example by being configured to be inserted into the lid portion 5114 or the base portion 5112.

Another feature of this arrangement is the use of support spokes 5194 in order to provide structural rigidity to the intermediate portion 5202. The spokes 5194, by themselves or in combination with the baffle 5192, may provide a handle for disassembly of the intermediate portion 5202 from the lid 5114 or the base portion 5112. This may improve usability as the user may grip the baffle 5192 and/or the spokes 5194 to separate the intermediate portion 5202 from the lid portion 5114 or base portion 5112. It should be understood that a number of other configurations may be possible wherein the support spokes 5194 are arranged alternatively to the exemplary arrangement as shown in FIGS. 43 and 44.

In an example of the current technology, the baffle 5192 may comprise a locating portion 5196 and a deflector portion 5198 as seen in FIGS. 43a, 43b, and 44. The locating portion 5196 may be in the form of a cylinder to assist in accurately locating the baffle 5192 in relation to the inlet tube 5124 by fitting around the outside of the vertical portion of the inlet tube 5124, i.e. at the inlet tube inner end 5125. In some forms, the baffle 5192 may further comprise a baffle seal 5197 to seal between the baffle 5192 and the inlet tube 5124, for example as shown in FIG. 48b. The baffle 5192 may also be configured in combination with the spokes 5194 so that at least some portions of the baffle 5192 may act as a spoke 5194 or vice versa.

An exemplary cross-section of the assembled lid 5114 is shown in FIGS. 45a and 45b. The diameter of the inlet tube 5124 or the locating portion 5196 may be varied along its length, for example in a frustro-conical arrangement, so as to progressively engage with each other. The inlet tube 5124, and the locating portion 5196 may also incorporate a complementary retaining mechanism such as a protrusion/slot combination 5205 as shown in FIGS. 45a and 45b.

It is also to be understood that the compliant portion 5116 may be located at an alternative location to the exemplary arrangements shown in FIGS. 41a, 41b, 42, 43a, 43b, and 44. For example, the compliant portion 5116 may be formed as a part of the lid portion 5114, as a part of the reservoir base portion 5112, or as a separate component by itself that is not integrally formed to any of the lid portion 5114, the intermediate portion 5202 and the base 5112. One exemplary method of forming the compliant portion 5116 with the lid portion 5114 or the base 5112 may be by overmoulding or use of a chemical adhesive.

FIG. 46 shows an exploded view of another example of the current technology. In this arrangement, the reservoir 5110 comprises a lid portion 5114, an intermediate portion 5202 and a base portion 5112 (not shown in FIG. 46 for clarity). The intermediate portion 5202 comprises the inlet tube 5124 and the outlet tube 5126 as well as a wall portion 5206 that is configured to be coupled with the lid portion 5114. Alternatively the intermediate portion 5202 may engage the base portion 5112, and may comprise one or both of the inlet tube 5124 and the outlet tube 5126. In some cases, the wall portion 5206 that is configured to couple with the lid portion 5114 may be connected with one or more of the inlet tube 5124 and the outlet tube 5126.

This configuration may allow removal of the inlet tube 5124 and/or the outlet tube 5126 for improved cleanability of the reservoir 5110. Furthermore, this configuration may improve spillback performance of the reservoir 5110 by increasing the internal volume of the reservoir 5110 as described above.

In some cases, the inlet tube 5124 and the outlet tube 5126 may be arranged so that removal of either or both of the tubes 5124, 5126 from the reservoir 5110 does not affect the predetermined maximum volume of water that the reservoir 5110 may retain. Such a configuration may allow cleaning of the tubes 5124, 5126 without removing any water from the reservoir 5110.

5.5.2.2.10 Overfill Prevention

In some prior art humidifier water reservoirs, overfilling of the water reservoir 5110, for example with a volume of liquid over and above a predetermined, maximum volume of liquid, may reduce effectiveness of a spill prevention feature. For example, if the reservoir 5110 was to be rotated away from its intended orientation while overfilled, the overfilled liquid in the reservoir 5110 may reach the inlet 5118 at a lower angle of tilt than if the reservoir 5110 had been only filled with the predetermined, maximum volume of liquid. As a result, some prior art humidifier water reservoirs have included a water filling indication mark to reduce occurrence of such overfilling, however this may only go some way towards ameliorating this risk as the user (e.g. patient 1000) may not be able to see, or be aware of the meaning of, the indication mark for example.

Some prior art humidifier water reservoirs comprise one or more tubes, which can act as egress paths for liquid (typically water) when the reservoir is filled with a volume of liquid which exceeds a threshold volume. One example of such prior art humidifier is described in PCT publication WO 2009/156921. However, one disadvantage of such an arrangement may be that if the reservoir is filled to this threshold volume, any movement of the reservoir may lead to egress of liquid from the reservoir (e.g. from movement of the volume of liquid). Consequently, transport of such a reservoir (e.g. from the patient's kitchen or bathroom) without spillage may be difficult, and the risk of spillage during usage (i.e. through the one or more tubes of the reservoir) may be high. Consequently, such prior art humidifier water reservoirs often comprise a water filling indication mark indicating the recommended predetermined maximum volume of water that the reservoir is to be filled with, where the recommended predetermined maximum volume of water is below (sometimes significantly below) the threshold volume at which water may begin to spill out of the one or more tubes in the reservoir. In some cases, such prior art humidifier water reservoirs may further comprise a secondary chamber configured to contain the water which has escaped the reservoir, for example before the water may enter the RPT device located upstream.

Another aspect of this technology is the inclusion of one or more overfill protection features configured to prevent filling the reservoir above the maximum volume of water when filling the humidifier reservoir, such as in its open configuration and/or the closed configuration.

In one arrangement as seen in FIGS. 30a and 30b, an overfill protection feature may include at least one orifice 5138 in the water reservoir 5110 to indicate over-filling. According to this aspect of the technology, when the water reservoir 5110 is being filled with the reservoir lid 5114 open, any water that is introduced into the reservoir 5110 beyond a predetermined maximum volume of the reservoir 5110 would spill out from the orifice 5138. This would indicate to the user that the reservoir 5110 is full, as well as preventing such overfilling. Advantageously water would spill out only through the at least one orifice 5138 rather than from all areas of the water reservoir resulting in less overflow spillage for the user to clean up. Thus, the at least one orifice defines egress path(s) of water when the predetermined maximum volume of water is exceeded. FIG. 30a shows the water reservoir 5110 in its open configuration, wherein an upper flange or lip 5224 of the base 5112 does not span the perimeter of the entire opening, creating an orifice 5138. FIG. 30b shows a portion of the base 5112 indicating the at least one orifice 5138. The at least one orifice 5138 may be in the form of one or more apertures, holes, slits or slots, or any other form that allows communication of fluid into and out of the water reservoir 5110. The at least one orifice 5138 may be formed in one or more positions around the upper flange or lip 5224 of the base 5112.

In an alternate arrangement, the overfill protection feature may include a sloped profile 5139. As shown in FIGS. 30c and 30d, the reservoir base 5112 may be arranged so that its side profile has a sloped profile 5139 in one or more directions. This arrangement may also indicate over-filling when the reservoir base 5112 is filled with water. In this arrangement, when the reservoir lid 5114 is in its open configuration, water may spill out at the base of the sloped profile 5139 rather than from all areas of the reservoir. Thus, the sloped profile defines an egress path of water when the predetermined maximum volume of water is exceeded. Advantages of the above methods may be that over-filling may become more difficult than has been in the prior art, and presents another advantage that in response to attempted over-filling, spillage may occur at more predictable locations.

In the examples of the at least one orifice 5138 and the sloped profile 5139 described above, the overfill protection feature is independent of the inlet tube 5124 and the outlet tube 5126. That is, the egress path of water is provided by the at least one orifice 5138 or the sloped profile 5139 rather than spilling out via the inlet tube 5124 and/or the outlet tube 5126.

In one form, when the water reservoir 5110 is in its closed configuration, a threshold volume of water which is required for the water to reach the inlet tube 5124 and/or the outlet tube 5126, and thus for the tubes 5124, 5126 to define an egress path of water, may be larger than the predetermined maximum volume of water. Such an arrangement may allow for a reduced risk of water egress from the reservoir 5110 during its transport or in use.

In some cases, the reservoir 5110 may comprise at least one water filling indication mark 5140 (e.g. on the base 5112 as shown in FIGS. 57a and 57b). The water filling indication mark 5140 may indicate to the user the predetermined maximum volume of water for the reservoir 5110 to contain, such as by indicating a water level which the reservoir 5110 is to be filled to. Further water filling indication marks 5140_a, 5140_b (e.g., as shown in FIGS. 57a and 57b) may indicate the level of fill of the reservoir 5110. In one arrangement (as shown in FIGS. 57a and 57b), the reservoir

5110 may be further configured so that the predetermined maximum volume of water is substantially identical to a maximum volume of water which will remain in the reservoir without causing egress via the at least one orifice 5138 as shown (or the sloped profile 5139—not shown). Thus, when the user (e.g. patient 1000) attempts to fill the reservoir 5110 beyond the water filling indication mark 5140, the user would cause water egress via the at least one orifice 5138 or the sloped profile 5139.

The reservoir 5110 may be further configured, for example as shown in FIGS. 58*a* and 58*b*, so that when the reservoir 5110 is in its closed configuration, a threshold volume of water required for the water (indicated by water line 5141_2) to reach the inlet tube 5124 and/or the outlet tube 5126 may be a greater volume than the predetermined maximum volume of water (indicated by water line 5141_1). As shown in FIG. 58*b*, the water line at the predetermined maximum volume of water 5141_1 may be substantially in line with a base or lower edge of the at least one orifice 5138 to allow egress of any excess water that is added above the water filling indication mark 5140. Such an arrangement may allow the patient 1000 to more easily transport the reservoir 5110 while it contains the predetermined maximum volume of water, as well as reduce a risk of water spillage/egress while the humidifier 5000 is in use.

In an alternative example, the base or lower edge of the at least one orifice 5138 or sloped profile 5139 may be above the predetermined maximum volume of water (indicated by water line 5141_1) but below the threshold volume of water (indicated by water line 5141_2). Preferably, the base or lower edge of the at least one orifice 5138 or sloped profile 5139 may be closer to the predetermined maximum volume of water (indicated by water line 5141_1) than the threshold volume of water (indicated by water line 5141_2).

Another aspect of this technology is that when the water reservoir 5110 is in its closed configuration, a compliant portion 5116 sealingly engages the base 5112 and the reservoir lid 5114 and blocks or seals the orifice 5138 or sloped profile 5139 preventing fluid communication into and out of the water reservoir 5110. One arrangement of this feature is shown in FIG. 31*a*, which shows that when the reservoir lid 5114 is closed (lid not shown in this image), the compliant portion 5116 sealingly engages with the base 5112 on the outside of the orifice 5138 and no longer allows communication of liquid or air into and out of the water reservoir 5110 through the orifice 5138. Similarly the compliant portion 5116 would engage with the base 5112 to surround the edges of the sloped profile preventing communication of liquid or air into and out of the water reservoir 5110 through the sloped profile 5139 as shown in FIG. 31*b*.

According to another aspect of the present technology, an overfill prevention feature may be configured to prevent overfilling when a user is attempting to fill the reservoir 5110 while in its closed configuration, for example via the inlet 5118 or outlet 5122.

In one form (shown in FIG. 49 without the reservoir base 5112), the overfill prevention feature may form one or more air locks to prevent further ingress of liquid into the reservoir 5110 when the predetermined maximum volume of liquid is in the reservoir 5110. In this form, when filling the reservoir 5110 in its closed configuration via the inlet 5118 or outlet 5122, one or more air locks would form an enclosure of air in the reservoir 5110 that is not displaced by the volume of liquid in the reservoir 5110. In an example shown in FIG. 49, the reservoir 5110 is in an orientation such that the normal to the inlet 5118 and the outlet 5122 are oriented vertically, as a user would orient the reservoir 5110 while filling it with water. The water level 5184 would rise, and reach the level shown on FIG. 49, whereupon the remaining volume of air in the reservoir 5110 is no longer able to access the inlet tube 5124 or the outlet tube 5126, therefore would no longer be able to escape from the reservoir 5110. The reservoir 5110 would thus not be able to receive any further volume of water into its interior volume. Adding further water would fill the inlet tube 5124 or the outlet tube 5126 depending upon whether the reservoir was being refilled through the inlet 5118 or the outlet 5122 respectively and then overflow out of the inlet 5118 or outlet 5122 respectively. This would indicate to the user that the reservoir 5110 was being overfilled.

Preferably, the volume of water in the reservoir 5110 when any further ingress of water into the reservoir 5110 is prevented by formation of the one or more air locks is substantially equal to the predetermined maximum volume of liquid to be retained in the reservoir 5110. In some cases, the reservoir 5110 may allow further filling of the inlet tube 5124 and/or the outlet tube 5126 although further ingress of water into the interior volume is prevented by the air locks. In such cases, the volume of liquid in the reservoir 5110 when the air locks are formed, as well as the volume of the inlet tube 5124 and/or the outlet tube 5126 may be configured so that when added together, they are substantially equal to the predetermined maximum volume of liquid to be retained in the reservoir 5110.

In some cases, for example where the normal to the inlet 5118 and the outlet 5122 may not be parallel, a user may fill the reservoir 5110 in one of a multiple orientations while closed. In such cases, the reservoir 5110 may be configured such that the appropriate air locks are formable at one of, or a plurality of the multiple orientations. The air locks need not be formed solely by occlusion of the inlet tube 5124 and/or the outlet tube 5126. In some forms (not shown), one or more air locks may be formed by occlusion of any cavities or ports which may allow fluid communication between the interior and the exterior of the reservoir 5110. Furthermore, the occlusion need not be performed by the volume of liquid in the reservoir 5110. In some forms, the volume of liquid, as it is increased, may deform or move another component to form a seal (and thus an air lock) in the reservoir.

5.5.2.2.11 Collapsible Inlet/Outlet Tube

As described above, any spillage of water from the reservoir 5110, especially through the inlet tube may be undesirable. One scenario where spillage of water may occur is when the reservoir 5110 and/or the humidifier 5000 is tilted away from its normal, working orientation, for example by its user (e.g., patient 1000). Tilting of the reservoir 5110 and/or the humidifier 5000 may occur while the patient 1000 is not receiving therapy, for example as the humidifier 5000 is picked up to be moved and/or packed away.

The humidifier 5000 may comprise one or more collapsible tubes, such a collapsible inlet tube and/or a collapsible outlet tube. A collapsible tube 5208 may be able to assume one of a plurality of configurations such as an open state (shown in FIG. 55*a*), and a closed state (shown in FIG. 55*b*). In some cases, the collapsible tube may be able to assume various degrees of 'openness' therebetween, such as 20%, 40%, 60% or 80% (e.g. as measured by a percentage of a 'fully open' cross section area).

The collapsible tube may comprise a flexible portion 5210, which may be configurable between a plurality of states to close or open the collapsible tube 5208 as shown in FIG. 55*a* and FIG. 55*b* (flexible portion 5210 marked by dotted boundaries). Alternatively, or additionally, the collapsible tube 5208 may comprise a rigid portion 5212 to locate and/or support the flexible portion 5210. In some forms, the rigid portion 5212 may comprise approximately half (50%) of the collapsible tube 5208 (e.g., in cross section), however other portions such as 30%, 40%, 60%, 70% may be also suitable according to the specific configuration of the collapsible tube 5208.

In one form, the collapsible tube may be biased towards one state, such as an open state, and may assume another state, such as a closed state, upon occurrence of an event, such as impingement of water onto the collapsible tube, orientation of the reservoir 5110 (and thus orientation of the collapsible tube). In another form, the collapsible tube may be biased towards a closed state, and further configured to assume an open state when acted upon by a flow of pressurised air, for example when the RPT device 4000 is switched on. In some forms, the collapsible tube may be biased towards that latest state that the collapsible tube had assumed. That is, if a flow of pressurised gas forced the collapsible tube into the open state, it may remain that way until it is forced into the closed state.

The collapsible tube 5208 may be constructed in any one of a number of suitable arrangements, one of which may be by overmoulding the flexible portion 5210 onto the rigid portion 5212. In other arrangements, the flexible portion 5210 and the right portion 5212 may be constructed separately and fastened together such as by a snap fit, or a one-way permanent latch, or by use of adhesives. In one form, the flexible portion 5210 of the collapsible tube 5208 may extend over an entire length of the collapsible tube 5208, in which case the flexible portion 5210 and the rigid portion 5212 may be joined at or around the circumference of the collapsible tube 5208. In another form, the flexible portion 5210 may only extend over a part of the entire length of the collapsible tube 5208, so that the flexible portion 5210 and the rigid portion 5212 may be joined at or around the circumference of the collapsible tube 5208, as well as to abut each other. Any number of other arrangements of a collapsible tube (e.g., in geometry, construction, composition) may be suitable to achieve the same effects as those described in the present disclosure.

In an example of the present technology which is shown in FIG. 56, a humidifier lid 5114 is shown comprising an inlet tube 5124 and an outlet tube 5126. In this example, the inlet tube 5124 comprises a rigid portion 5212 towards a top of the inlet tube 5124, and a flexible portion 5210 (shaded portion in FIG. 56) towards the bottom of the inlet tube 5124. Thus, in one arrangement, the flexible portion 5210 may be biased towards an open configuration and collapse only as a pressure from the volume of water acts upon an exterior of the flexible portion 5210 (e.g., from within the reservoir 5110). In another arrangement, the flexible portion 5210 may be biased towards a closed configuration and open only when a flow of pressurised air is delivered into the reservoir 5110 from the reservoir inlet 5118.

Use of a collapsible tube may be advantageous in that the volume of the collapsed tube may be effectively added to the interior of the reservoir, thereby lowering a depth of the volume of water in the reservoir. This may have two outcomes, one of reducing a likelihood of the volume of water in the reservoir reaching an opening of the inlet tube and/or an outlet tube, and another of allowing a size of the reservoir to be smaller than would be otherwise possible. Another advantage of a collapsible tube may be that it may be able to act as a one-way valve, by either closing when reached by water and/or opening when a flow of pressurised air reaches it.

5.5.2.2.12 Retaining Clip

The reservoir lid 5114 may include a feature by which the water reservoir 5110 is to be retained in the water reservoir dock 5130 once the two members are engaged with each other. In one arrangement a retaining feature may be a protrusion, or a clip, 5142 on the reservoir lid 5114 as shown in FIGS. 32 to 33. FIGS. 32 to 33 show a water reservoir 5110 and the reservoir dock 5130. Here, a protrusion, or a clip, 5142 on the reservoir lid 5114 removably engages with a corresponding dock locking recess 5144 in the water reservoir dock 5130 when the water reservoir 5110 is inserted into the water reservoir dock 5130. This connection secures the water reservoir 5110 relative to the water reservoir dock 5130.

As described above the compliant portion 5116 of the reservoir is compressed to enable insertion of the reservoir into the dock 5130. The compression of the compliant portion 5116 allows a portion of the reservoir 5110 to slide into the dock 5130 and allows the protrusion (or clip 5142 to slide initially under the outer edge surface of the dock 5130 to reach the dock locking recess 5144. The compression force applied to the reservoir for insertion may then be released to allow the protrusion (or clip) 5142 to engage with the dock locking recess 5144 and securing of the reservoir 5110 within the dock 5130. When the reservoir 5110 is secured within the dock 5130 the compliant portion 5116 is no longer in or in a reduced compressed state. Similarly, in order to be able to remove the water reservoir 5110 from the water reservoir dock 5130, the compliant portion 5116 must be compressed as to disengage the lid protrusion 5142 from the dock locking recess 5144.

The lid protrusion 5142 may be further configured with a taper as shown in FIG. 33. The taper may be directed to increase in height away from the direction of insertion, to increase the amount of interference between the protrusion 5142 and the dock 5130 progressively during insertion. It would be clear to those skilled in the art that in an alternative arrangement the lid protrusion 5142 may be a recess, and the dock locking recess 5144 may be a corresponding protrusion. Alternatively one of any number of retaining features that are known in the art may be used to achieve the same outcomes as described above.

5.5.2.3 Heater Plate 5120

A heater plate 5120 is used to transfer heat to the water reservoir 5110. The heater plate 5120 may form a part of the reservoir dock 5130, and may be located on or near the base of the humidifier 5000 as shown in FIG. 14. The heater plate 5120 may be formed, for example, of a nickel chrome alloy, stainless steel or anodised aluminium. The heater plate 5120 may comprise a heating element 5240, for example a layered heating element such as one described in the PCT Patent Application Publication Number WO 2012/171072, the entire document of which is incorporated herewithin by reference.

5.5.2.4 Humidifier End Cap 5300

In one example of the present technology as shown in FIG. 59, the humidifier 5000 may comprise a humidifier end cap 5300 configured to direct the flow of air from the RPT device 4000 to the humidifier outlet 5172. In some arrangements when humidification is not required and the humidifier 5000 is integrated with the RPT device 4000, the humidifier 5000 may comprise an end cap in lieu of a humidifier reservoir 5110. As shown in FIG. 59, the humidifier end cap 5300 may be configured to be received in the water reservoir dock 5130 interchangeably with the reservoir 5110.

In one form, as shown in FIGS. 59 and 60, the humidifier end cap 5300 may comprise an end cap inlet 5310 for receiving the flow of air (e.g. from the dock outlet 5168), an end cap outlet 5320 for delivering the flow of air (e.g. to the dock air inlet 5170) and an end cap latch 5330 for locking and/or releasing the end cap 5300 to/from the water reservoir dock 5130.

The end cap 5300 may comprise an identification element, to allow a controller, such as the central controller 4230 or the humidifier controller 5250, to detect its presence (or absence), for example in the reservoir dock 5130. The reservoir dock 5130 may comprise a complementary detection element, to detect the presence (or absence) of the end cap 5300. In one form, detection of the presence or absence of the humidifier controller 5250 may cause the controller to perform one more of: switch off/on the heater plate 5120, adjust the power output of the heater plate 5120, switch off/on the heated air circuit 4171, adjust the power output of the heated air circuit 4171, adjust the pressure drop estimation between the pressure generator 4140 and the patient interface 3000, disable/enable user interface elements relating to operation of the humidifier 5000, or disable/enable data logging/data reporting relating to operation of the humidifier 5000. In one form, as shown in FIG. 59 and FIG. 60, the humidifier end cap 5300 may comprise an identification element (shown in the form of a magnet 5340) disposed on the end cap 5300, such as in an end cap magnet holder 5345. The identification element may be used for detection of the humidifier end cap 5300 by the controller via the detection element, for example the detection element may include a Hall Effect sensor located in or near the reservoir dock 5130 (not shown) such as on a printed circuit board (PCB) in the RPT device 4000.

One advantage of an end cap 5300 comprising an identification element, may be to allow reduced power consumption or customised operation of the humidifier 5000 where an end cap 5300 is used. A further advantage of having the heater plate on by default and turned off by engagement of the end cap 5300 is in a single step of installing the end cap both the heater plate 5120 is deactivated and access to the heater plate is prevented.

Yet further, where a manufacturer may produce more systems that include humidifiers 5000 with a reservoir 5110 than systems that include an end cap 5300, it may be advantageous for the manufacturer (e.g., costs) to place the identification element on the end cap 5300, as the identification element, may incur additional cost (or time) to whichever component (i.e., reservoir 5110 or the end cap 5300) that it may be coupled to.

5.5.3 Humidifier Electrical & Thermal Components

A humidifier 5000 may comprise a number of electrical and/or thermal components such as those listed below.

5.5.3.1 Sensor 5270

A humidifier 5000 may comprise one or more sensors 5270, such as an air pressure sensor(s), an air flow sensor(s), a temperature sensor(s) and/or a relative humidity sensor(s). A sensor may produce an output signal indicating the property that it measures, and the output signal may be communicated to a controller such as the central controller 4230 and/or the humidifier controller 5250. In some forms, a sensor may be located externally to the humidifier 5000 (such as in the air circuit 4170 or in an external module) while communicating the output signal to the controller.

5.5.3.1.1 Flow Sensor

A flow sensor may be provided to a humidifier 5000 in addition to, or instead of, a flow sensor 4274 provided in the RPT device 4000.

5.5.3.1.2 Temperature Sensor(s)

A humidifier 5000 may comprise a temperature sensor which may be configured to measure a temperature of the heating element 5240 and/or a temperature of the flow of air in the reservoir 5110. In some forms, the humidifier 5000 may further comprise a temperature sensor to detect the temperature of the ambient air.

5.5.3.1.3 Humidity Sensor(s)

In one form, the humidifier 5000 may comprise a humidity sensor to detect a relative humidity of the ambient air. The humidity sensor may be an absolute humidity sensor or a relative humidity sensor. When a relative humidity sensor is used, a value of absolute humidity may be determined based on measured values of relative humidity and temperature of the flow of the air.

5.5.3.2 Heating Element(s) 5240

The heating element 5240 may be a heat generating component such as an electrically resistive heating track. One suitable example of a heating element 5240 is a layered heating element such as one described in the PCT Patent Application Publication Number WO 2012/171072, the entire document of which is incorporated herewithin by reference.

5.5.3.3 Heated Air Circuit 4171

A heated air circuit 4171 may be used in addition to, or instead of, the air circuit 4170. Temperature of the flow of air that is output from the humidifier 5000 may be higher than ambient temperature. As a result, heat loss may occur from the flow of air to the ambient air, thereby increasing the relative humidity of the humidified flow of air. In some cases, condensation may occur where the relative humidity increases to at or near 100% RH.

In one form, the humidifier 5000 may comprise, or be connected to, a heated air circuit 4171. Use of a heated air circuit 4171 may prevent or reduce condensation of water from the flow of air as it travels from the humidifier 5000 to the patient interface 3000. For instance the heated air circuit 4171 may provide heat to the flow of air to compensate for heat loss to the ambient air.

The heated air circuit 4171 may comprise one or more sensors, such as a temperature sensor and/or a humidity sensor. Use of a temperature sensor and/or a humidity sensor may help determine the temperature and/or humidity (absolute and/or relative) in the heated air circuit 4171, for example at its outlet. In some cases, the heated air circuit 4171 may comprise a heating element 5240, such as a heated coil, configured to provide a heat input to the heated air circuit 4171.

5.5.3.4 Humidifier Controller 5250

According to one arrangement of the present technology, a humidifier 5000 may comprise a humidifier controller 5250 as shown in FIG. 5b. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs (e.g. from sensors 5270) measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5b, the humidifier controller may comprise a plurality of controllers, such as a central humidifier controller 5251, a heated air circuit controller 5254 configured to control the temperature of a heated air circuit 4171 and/or a heating element controller 5252 configured to control the temperature of a hot plate. The heated air circuit controller 5254 may receive an input from one or more sensors to control operation of the heated air circuit 4171. As an example, the heated air circuit controller 5254 may receive from sensors 5270 the temperature and the relative humidity of the humidified flow of air to adjust the heat output by the heated air circuit 4171.

5.6 Glossary

For the purposes of the present technology disclosure, in certain forms of the present technology, one or more of the following definitions may apply. In other forms of the present technology, alternative definitions may apply.

5.6.1 General

Air: Air will be taken to include breathable gases, for example atmospheric air with supplemental oxygen.

Continuous Positive Airway Pressure (CPAP): CPAP treatment will be taken to mean the application of a supply of air to the entrance to the airways at a pressure that is continuously positive with respect to atmosphere.

5.6.2 Aspects of RPT Devices

Air circuit: A conduit or tube constructed and arranged in use to deliver a supply of air between an upstream component (such as a RPT device) and a downstream component (such as a patient interface). In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

5.6.3 Humidifiers

Water reservoir: A water reservoir (also commonly referred to as a water tub, humidifier tub or a humidifier reservoir) is a chamber configured to contain a body/volume of liquid (e.g., water) used to add humidity to the flow of air.

5.6.4 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240

Polycarbonate: a typically transparent thermoplastic polymer of Bisphenol-A Carbonate.

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

While the present technology has been described in connection with what are presently considered to be the most practical and preferred examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., aspects of one example may be combined with aspects of another example to realize yet other examples. Further, each independent feature or component of any given assembly may constitute an additional example.

5.8 Additional Technology Examples

Example 1. The apparatus for humidifying a flow of air, comprising:
a heater plate;
a chamber in fluid communication with the flow of air; and
a reservoir comprising a conductive portion in thermal engagement with the heater plate,
the apparatus configured so that varying a first pressure of the flow of air in the chamber varies a level of thermal engagement between the conductive portion and the heater plate.

Example 2. The apparatus as described in example 1, wherein the reservoir further comprises an inlet and an outlet.

Example 3. The apparatus as described in example 2, wherein the thermal engagement is in a first direction that is substantially normal to a surface of the conductive portion.

Example 4. The apparatus as described in any one of examples 1-3, further configured to vary a magnitude of a force between the conductive portion and the heater plate in the first direction as the first pressure is varied.

Example 5. The apparatus as described in any one of examples 1-4, wherein the chamber is part of the reservoir.

Example 6. The apparatus as described in any one of examples 1-5, wherein the chamber further comprises a compliant portion.

Example 7. The apparatus as described in any one of examples 1-6, wherein the apparatus further comprises a dock configured to receive the reservoir, and the dock comprises the heater plate.

Example 8. The apparatus as described in example 7, wherein the dock further comprises a cavity having a top portion and a bottom portion, the bottom portion having the heater plate located thereon, the cavity configured to retain at least a portion of the reservoir therein.

Example 9. The apparatus as described in example 8, wherein the compliant portion is compressed to enable insertion of the reservoir into the cavity of the dock.

Example 10. The apparatus as described in any one of examples 8 or 9, wherein the top portion of the cavity is moveable between an open and closed configuration to facilitate insertion of the reservoir into the cavity.

Example 11. The apparatus as described in any one of examples 6-10, wherein the compliant portion is configured to adjust in size as the first pressure is varied to vary the level of thermal engagement between the heater plate and the conductive portion.

Example 12. The apparatus according to any one of examples 1-11, wherein the reservoir further includes a base and a lid, the base structured to hold a volume of liquid and including the conductive portion.

Example 13. The apparatus according to example 12, wherein the base and lid are pivotably coupled together.

Example 14. The apparatus according to any one of examples 12-13, wherein the compliant portion forms a seal between the base and lid.

Example 15. The apparatus according to any one of examples 12-14, wherein the reservoir further includes a latch to secure the base and lid together.

Example 16. The apparatus according to any one of examples 7-15, wherein the reservoir further comprises at least one handle to facilitate coupling of the reservoir to the dock.

Example 17. The apparatus according to any one of examples 8-16 wherein the reservoir further includes a retaining clip adapted to engage with a recess on the dock to retain the reservoir in the cavity of the dock.

Example 18. The apparatus according to any one of examples 7 to 17, wherein the reservoir is structured to prevent refilling of the reservoir when the reservoir is coupled to the dock.

Example 19. The apparatus according to example 18, wherein at least a portion of the reservoir is prevented from being opened when the reservoir is coupled to the dock.

Example 20. The apparatus according to any one of examples 18 or 19, wherein the reservoir includes a re-filling cap.

Example 21. The apparatus according to any one of examples 1-20, further comprising an overfill protection element configured to prevent filling the reservoir above a predetermined maximum volume of water.

Example 22. The apparatus according to example 21, wherein the overfill protection element comprises at least one orifice formed in a wall of the reservoir, the at least one orifice defines an egress path of water when the predetermined maximum volume of water is exceeded.

Example 23. The apparatus according to example 21, wherein the overfill protection element comprises a sloped profile in the side profile of a wall of the reservoir, the sloped profile defines an egress path of water when the predetermined maximum volume of water is exceeded.

Example 24. A method for varying thermal contact between a heater plate and a reservoir in a humidification system for humidifying a flow of air, the method comprising:
varying a pressure of the flow of air in the reservoir that is in fluid communication with the flow of air to vary a force between the heater plate and the reservoir.

Example 25. An apparatus for humidifying a flow of air, comprising:
a heater plate; and
a reservoir comprising:
an inlet to receive the flow of air;
an outlet; and
a conductive portion in thermal contact with the heater plate,
and wherein the apparatus is configured so that varying a pressure of the flow of air in the reservoir varies a force between the heater plate and the conductive portion in a direction of thermal contact.

Example 26. The apparatus as described in example 25, further comprising a dock connectable with the reservoir.

Example 27. The apparatus as described in example 26, wherein the dock is configured to constrain the reservoir from opening in the direction of thermal contact.

Example 28. A reservoir configured to contain a volume of liquid for humidifying a pressurised flow of air, comprising:
- a base portion comprising a conductive portion;
- a lid portion comprising an inlet and an outlet; and
- a compliant portion
  - wherein the base portion and the lid portion are pivotably engaged and configurable in an open configuration and a closed configuration while pivotably engaged, and the seal sealingly engages the base portion and the lid portion when the reservoir is in the closed configuration.

Example 29. The reservoir as described in example 28, wherein the compliant portion comprises an outlet tube, and a baffle, the baffle being configured to connect to the inlet tube.

Example 30. An apparatus for humidifying a flow of air, comprising:
- a heater plate; and
- a reservoir comprising:
- an inlet;
- an outlet;
- a compliant portion; and
- a conductive portion in thermal contact with the heater plate,
  - wherein the apparatus is configured so that varying a height of the compliant portion varies a level of thermal engagement between the conductive portion and the heater plate.

Example 31. The apparatus as described in example 30, wherein the apparatus is configured so that the thermal engagement is in a first direction that is substantially normal to a surface of the conductive portion.

Example 32. A method of varying a level of thermal engagement in a humidifier apparatus, the method comprising:
- (i) thermally engaging a heater plate with a conductive portion of a reservoir; and
- (ii) varying a height of a compliant portion of the reservoir to vary a level of thermal engagement between the conductive portion and the heater plate.

Example 33. A water reservoir for a humidifier apparatus, the reservoir comprising:
- a plurality of walls forming a cavity to hold the a predetermined maximum volume of water;
- an inlet tube for receiving a supply of air into the reservoir, the inlet tube comprising an inner end and an outer end; and
- an outlet tube for delivering a supply of air from the reservoir, the outlet tube comprising an inner end and an outer end;
- wherein the inlet tube and the outlet tube are configured that when the reservoir contains the predetermined maximum volume of water, at least one of the inner end or the outer end of the inlet tube, and at least one of the inner end or the outer end of the outlet tube are above the predetermined maximum volume of water regardless of an orientation of the reservoir.

Example 34. A water reservoir for a humidifier apparatus, the reservoir comprising:
- an inlet tube for receiving a supply of air into the reservoir;
- an outlet tube for delivering a supply of air from the reservoir;
- wherein at least one of the inlet tube or the outlet tube is able to assume at least two configurations.

Example 35. The water reservoir as described in example 34, wherein the at least two configurations comprises an open configuration and a closed configuration.

Example 36. The water reservoir as described in example 35, wherein the at least one or the inlet tube or the outlet tube is collapsible to form the closed configuration.

5.9 Reference Signs List

Number Feature Item
1000 patient
3000 patient interface
3100 seal-forming structure
3200 plenum chamber
3300 stabilising structure
3400 vent
3600 connection port
4000 RPT device
4010 external housing
4012 upper portion
4014 lower portion
4015 panel
4016 chassis
4020 pneumatic block
4100 pneumatic components
4110 air filter
4112 inlet air filter
4114 outlet air filter
4120 muffler
4122 inlet muffler
4124 outlet muffler
4140 pressure generator
4142 blower
4144 motor
4160 anti-spillback valve
4170 air circuit
4171 heated air circuit
4180 supplemental oxygen
4200 electrical components
4202 printed circuit board assembly (PCBA)
4210 electrical power supply
4220 input devices
4230 central controller
4232 clock
4240 therapy device controller
4250 protection circuits
4260 memory
4270 transducer
4272 pressure transducer
4274 flow transducer
4276 motor speed transducer
4280 data communication interface
4282 remote external communication network
4282 local external communication network
4286 remote external device
4288 local external device
4290 output devices
4292 display driver
4294 display
4300 algorithms
4310 pre-processing module
4312 pressure compensation algorithm
4314 vent flow algorithm 4316 leak flow algorithm
4318 respiratory flow algorithm
4320 therapy engine module
4321 phase determination algorithm
4322 waveform determination algorithm
4323 ventilation determination algorithm
4324 flow limitation determination algorithm
4325 apnea/hypopnea determination algorithm
4326 snore determination algorithm
4327 patency determination algorithm
4328 therapy parameter determination algorithm
4330 control module
4340 fault conditions
4500 method
4520 method step
4530 method step
4540 method step
4550 method step
4560 method step
5000 humidifier
5110 water reservoir
5112 reservoir base
5114 reservoir lid
5116 compliant portion
5117 carrier
5118 reservoir inlet
5120 heater plate
5122 reservoir outlet
5124 inlet tube
5125 inlet tube inner end
5126 outlet tube
5127 outlet tube inner end
5128 inner end wall
5130 water reservoir dock
5132 first dock seal
5134 second dock seal
5136 turning vane
5138 orifice
5139 sloped profile
5140 water filling indication mark
5140_a water filling indication mark
5140_b water filling indication mark
5141_1 water level at predetermined maximum volume of water
5141_2 water level at threshold volume of water
5142 retention protrusion
5144 dock locking recess
5146 base upper body
5148 base bottom plate
5150 sealing element
5152 conductor plate
5154 handle recess
5156 handle recess
5158 hinge
5159 hinge recess
5160 dock cavity
5166 handle grip
5168 dock air outlet
5170 dock air inlet
5172 humidifier outlet
5174 base
5176 top
5178 compliant portion
5180 cap
5182 water
5184 water level
5186 reservoir latch
5192 baffle
5194 support spoke
5195 flow director
5196 locating portion
5197 seal
5198 deflector portion
5202 intermediate portion
5205 protrusion/slot combination
5206 wall portion
5208 collapsible tube
5210 flexible portion
5212 rigid portion
5220 rotation guide
5222 rotation stop
5224 inner lip
5226 outer lip
5240 heating element
5250 humidifier controller
5251 central humidifier controller
5252 heating element controller
5254 heated air circuit controller
5270 sensors
5300 humidifier end cap
5310 end cap inlet
5320 end cap outlet
5330 end cap latch
5340 magnet
5345 end cap magnet holder

The invention claimed is:

1. A water reservoir for an apparatus for generating a humidified flow of air for delivery to an entrance of the airways of a patient for respiratory therapy, the water reservoir comprising:
   a reservoir base configured to hold a volume of water;
   a disconnectable reservoir lid comprising an inlet and an outlet;
   a hinge joint to pivotally couple the reservoir lid to the reservoir base for pivotal movement between an open position and a closed position,
   wherein the reservoir lid and the reservoir base cooperate to form a sealed internal volume at the closed position; and
   a supporting arrangement configured and arranged to support the reservoir lid at the open position,
   wherein the supporting arrangement comprises a portion of the reservoir lid configured and arranged to abuttingly engage a portion of the reservoir base at the open position, and
   wherein the supporting arrangement is configured and arranged to disconnect the reservoir lid from the reservoir base at the hinge joint when the reservoir lid is over-pivoted beyond the open position.

2. The water reservoir according to claim 1, wherein the hinge joint includes a pair of hinges each configured to engage with a respective one of a pair of recess portions to provide said pivotal movement.

3. The water reservoir according to claim 2, wherein the pair of hinges are provided to the reservoir lid and the pair of recess portions are provided to the reservoir base.

4. The water reservoir according to claim 3, wherein each side of the reservoir lid includes a hinge arm and a respective one of the pair of hinges extends inwardly from the hinge arm.

5. The water reservoir according to claim 2, wherein at least one of the pair of hinges includes a tapered surface configured and arranged to facilitate disconnection from a respective one of the pair of recess portions when the reservoir lid is over-pivoted beyond the open position.

6. The water reservoir according to claim 5, wherein the tapered surface is provided to a face of the free end of the at least one of the pair of hinges.

7. The water reservoir according to claim 2, wherein each of the pair of hinges includes a cylindrical shape.

8. The water reservoir according to claim 1, wherein the portion of the reservoir base includes a rotation guide configured and arranged to guide and provide engagement with the portion of the reservoir lid at the open position.

9. The water reservoir according to claim 1, further comprising a compliant portion configured to sealingly engage the reservoir lid and the reservoir base when the water reservoir is in the closed position.

10. The water reservoir according to claim 1, further comprising a latch to secure the reservoir base and the reservoir lid together.

11. The water reservoir according to claim 10, wherein the hinge joint is one side of the water reservoir and the latch is positioned on an opposite side of the water reservoir.

12. The water reservoir according to claim 10, further comprising a compliant portion configured to sealingly engage the reservoir lid and the reservoir base when the water reservoir is in the closed position, and the latch is configured to allow the reservoir lid and the reservoir base to move relative to one another while the compliant portion maintains sealing between the reservoir lid and the reservoir base.

13. The water reservoir according to claim 1, wherein the hinge joint includes a pair of hinges each configured to engage with a respective one of a pair of recess portions to provide said pivotal movement, wherein the reservoir lid includes an arm having a support edge, and wherein the reservoir base includes an abutment support surface to engage the support edge at the open position of the reservoir lid.

14. The water reservoir according to claim 1, wherein the portion of the reservoir lid is configured and arranged to act as a pivot of a cantilever when the reservoir lid is over-pivoted beyond the open position.

15. The water reservoir according to claim 1, wherein the hinge joint includes a pair of hinges each configured to engage with a respective one of a pair of recess portions to provide said pivotal movement,
wherein at least one of the pair of hinges includes a cylindrical shape with a tapered surface configured and arranged to facilitate disconnection from a respective one of the pair of recess portions when the reservoir lid is over-pivoted beyond the open position,
wherein the tapered surface is provided to a face of the free end of the at least one of the pair of hinges,
wherein the reservoir lid comprises an inlet and an outlet,
further comprising a compliant portion configured to sealingly engage the reservoir lid and the reservoir base when the water reservoir is in the closed position,
further comprising a latch to secure the reservoir base and the reservoir lid together, and
wherein the hinge joint is one side of the water reservoir and the latch is positioned on an opposite side of the water reservoir.

16. An apparatus for generating a humidified flow of air, comprising:
a water reservoir dock; and
the water reservoir according to claim 1 provided to the water reservoir dock.

17. The apparatus according to claim 16, wherein the water reservoir dock forms a cavity to at least partially receive the water reservoir.

18. The apparatus according to claim 16, wherein the water reservoir dock includes a heater plate adapted to thermally engage a conductive portion provided to the water reservoir.

19. A water reservoir for an apparatus for generating a humidified flow of air for delivery to an entrance of the airways of a patient for respiratory therapy, the water reservoir comprising:
a reservoir base configured to hold a volume of water;
a reservoir lid comprising an inlet and an outlet; and
a hinge joint to pivotally and removably couple the reservoir lid to the reservoir base for pivotal movement between an open position and a closed position,
wherein the reservoir lid and the reservoir base cooperate to form a sealed internal volume at the closed position,
wherein the hinge joint comprises a hinge configured to engage with a recess portion to provide said pivotal movement, and
wherein the hinge includes a tapered surface configured and arranged to facilitate disconnection from the recess portion when the reservoir lid is over-pivoted beyond the open position.

20. The water reservoir according to claim 19, wherein the hinge joint comprises a pair of said hinge and a pair of said recess portion, each hinge configured to engage with a respective one said recess portion to provide said pivotal movement, and each hinge includes the tapered surface.

21. The water reservoir according to claim 20, wherein the pair of hinges are provided to the reservoir lid and the pair of recess portions are provided to the reservoir base.

22. The water reservoir according to claim 19, wherein the tapered surface is provided to a face of the free end of the hinge, and wherein the tapered surface includes an orientation with respect to the recess portion at the open position to allow said disconnection more easily when compared to another orientation of the tapered surface with respect to the recess portion.

23. The water reservoir according to claim 19, further comprising a latch to secure the reservoir base and the reservoir lid together, wherein the hinge joint is one side of the water reservoir and the latch is positioned on an opposite side of the water reservoir.

24. The water reservoir according to claim 23, further comprising a compliant portion configured to sealingly engage the reservoir lid and the reservoir base when the water reservoir is in the closed position, and the latch is configured to allow the reservoir lid and the reservoir base to move relative to one another while the compliant portion maintains sealing between the reservoir lid and the reservoir base.

25. The water reservoir according to claim 19, wherein the reservoir lid includes a pair of support edges, and wherein the reservoir base includes a pair of abutment support surfaces to engage the respective support edges at the open position of the reservoir lid.

26. The water reservoir according to claim 25, wherein the pair of support edges and the pair of abutment support surfaces are configured and arranged to hold the reservoir lid at the open position in which the reservoir lid is arranged upright relative to the reservoir base.

27. The water reservoir according to claim 19,
wherein the tapered surface is provided to a face of the free end the hinge, wherein each of the pair of hinges includes a cylindrical shape, further comprising a latch to secure the reservoir base and the reservoir lid together, wherein the hinge joint is one side of the water reservoir and the latch is positioned on an opposite side of the water reservoir, further comprising a compliant portion configured to sealingly engage the reservoir lid and the reservoir base when the water reservoir is in the closed position, and the latch is configured to allow the reservoir lid and the reservoir base to move relative to one another while the compliant portion maintains sealing between the reservoir lid and the reservoir base.

28. An apparatus for generating a humidified flow of air, comprising:
   a water reservoir dock; and
   the water reservoir according to claim 19 provided to the water reservoir dock.

29. The apparatus according to claim 28, wherein the water reservoir dock forms a cavity to at least partially receive the water reservoir.

30. The apparatus according to claim 28, wherein the water reservoir dock includes a heater plate adapted to thermally engage a conductive portion provided to the water reservoir.

* * * * *